(12) United States Patent
Chinea Santiago et al.

(10) Patent No.: US 9,896,482 B2
(45) Date of Patent: Feb. 20, 2018

(54) BETA HAIRPIN PEPTIDES HAVING ANTIVIRAL PROPERTIES AGAINST DENGUE VIRUS

(71) Applicant: CENTRO DE INGENIERÍA GENÉTICA Y BIOTECNOLOGÍA, Playa la Habana (CU)

(72) Inventors: Glay Chinea Santiago, Playa la Habana (CU); Vivian Huerta Galindo, Playa la Habana (CU); Alejandro Miguel Martín Dunn, Playa la Habana (CU); Hilda Elisa Garay Pérez, Playa la Habana (CU); Osvaldo Reyes Acosta, Playa la Habana (CU); Viviana Falcón Cama, Playa la Habana (CU); Dianne Pupo Gómez, Havana (CU); Alexis Yero Díaz, Havana (CU); Gabriel Jesús Márquez Perera, Playa la Habana (CU); Mónica Sarría Núñez, Havana (CU); Osmany Guirola Cruz, Havana (CU); Rocío Garateix Suárez, Havana (CU); Karen Alvarez Pérez, Havana (CU); Sonia González Blanco, Playa la Habana (CU); Mariela Vázquez Castillo, Playa la Habana (CU); Luis Javier González López, Playa la Habana (CU)

(73) Assignee: Centro de Ingenieria Genética y Biotechnologia, La Habana (CU)

(*) Notice: Subject to any disclaimer, the term of this patent is extended or adjusted under 35 U.S.C. 154(b) by 0 days.

(21) Appl. No.: 15/119,058

(22) PCT Filed: Feb. 26, 2015

(86) PCT No.: PCT/CU2015/000002
§ 371 (c)(1),
(2) Date: Aug. 15, 2016

(87) PCT Pub. No.: WO2015/131858
PCT Pub. Date: Sep. 11, 2015

(65) Prior Publication Data
US 2017/0152290 A1    Jun. 1, 2017

(30) Foreign Application Priority Data
Mar. 3, 2014  (CU) .................................. 2014-0026

(51) Int. Cl.
| | |
|---|---|
| *A61K 38/10* | (2006.01) |
| *C07K 7/08* | (2006.01) |
| *C07K 14/00* | (2006.01) |
| *A61K 38/16* | (2006.01) |
| *A61K 47/42* | (2017.01) |
| *A61K 47/69* | (2017.01) |
| *A61K 38/00* | (2006.01) |

(52) U.S. Cl.
CPC ................ *C07K 7/08* (2013.01); *A61K 38/10* (2013.01); *A61K 38/16* (2013.01); *A61K 47/42* (2013.01); *A61K 47/6929* (2017.08); *C07K 14/00* (2013.01); *A61K 38/00* (2013.01); *C07K 2319/21* (2013.01)

(58) Field of Classification Search
None
See application file for complete search history.

(56) References Cited

FOREIGN PATENT DOCUMENTS

WO    WO-2007124698 A2 * 11/2007  ........... C07K 14/005

OTHER PUBLICATIONS

Xie et al Anal. Bioanal. Chem. (2013) 405 p. 9739-9746.*
Agarwal et al., "Total synthesis of the Gene for an Alanine Transfer Ribonucleic Acid from Yeast," Nature vol. 227, Jul. 4, 1970, pp. 27-34.
Beaucage et al., "Deoxynucleoside Phosphoramidites—A New Class of Key Intermediates for Deoxypolynucleotide Synthesis," Tetrahedron Letters, vol. 22, No. 20, pp. 1859-1862, 1981.
Chambers et al., "Flavivirus Genome Organization, Expression, and Replication," Annu. Rev. Microbiol. 1990, 44:649-88.
Chu et al., "Genetic Relatedness among Structural Protein Genes of Dengue 1 Virus Strains," J. gen. Virol. (1989), 70, pp. 1701-1712.
Goncalvez et al. "Diversity and Evolution of the Envelope Gene of Dengue Virus Type 1," Virology 303, pp. 110-119 (2002).
Gorodkin et al., "Displaying the information contents of structural RNA alignments: the structure logos," Cabios, vol. 13 No. 6 1997, pp. 583-586.
Gubler, Duane, "Dengue and Dengue Hemorrhagic Fever," Clinical Microbiology Reviews, Jul. 1998, vol. 11, No. 3, pp. 480-496.
Halstead, Scott, "Neutralization and Antibody-Dependent Enhancement of Dengue Viruses," Advances in Virus Research, vol. 60, pp. 421-467 (2003).
Halstead, Scott, "Pathogenesis of Dengue: Challenges to Molecular Biology," Science, vol. 239, Jan. 29, 1988, pp. 476-481.
Halstead et al., "Dengue virus: molecular basis of cell entry and pathogenesis, Jun. 25-27, 2003, Vienna, Austria," Vaccine 23 (2005) pp. 849-856.
Henchal et al., "The Dengue Viruses," Clinical Microbiology Reviews, Oct. 1990, vol. 3, No. 4, pp. 376-396.
Hung et al., "An External Loop Region of Domain III of Dengue Virus Type 2 Envelope Protein Is Involved in Serotype-Specific Binding to Mosquito but Not Mammalian Cells," Journal of Virology, Jan. 2004, vol. 78, No. 1, pp. 378-388.
Juarez et al., "Existence of Different Structrual Intermediates on the Fibrillation Pathway of Human Serum Albumin," Biophysical Journal, vol. 96, Mar. 2009, pp. 2353-2370.

(Continued)

*Primary Examiner* — Fred H Reynolds
(74) *Attorney, Agent, or Firm* — Hoffmann & Baron, LLP

(57) ABSTRACT

The present invention discloses structurally constrained synthetic peptides that have been optimized for the formation of a beta hairpin structure. Said peptides are able to inhibit or attenuate Dengue virus (DENV) infections. The invention also discloses pharmaceutical compositions containing these synthetic peptides, which are useful for the prevention and/or treatment of DENV-caused infections. Likewise, the invention disclosed a method for treating infections caused by this virus.

6 Claims, 11 Drawing Sheets

(56) References Cited

OTHER PUBLICATIONS

Kaiser et al., "Color Test for Detection of Free Terminal Amino Groups in the Solid-Phase Synthesis of Peptides," Analytical Biochemistry, vol. 34, Issue 2, Apr. 1970, pp. 595-598.
Kouri et al., "Why dengue haemorrhagic fever in Cuba?" Transactions of the Royal Society of Tropical Medicine and Hygiene (1987), 81, pp. 821-823.
Kuhn et al., "Structure of Dengue Virus: Implications for Flavivirus Organization, Maturation, and Fusion," Cell. Mar. 8, 2002, 108(5): 717-725.
Laemmli, U.K., "Cleavage of Structural Proteins during the Assembly of the Head of Bacteriophage T4," Nature vol. 227 Aug. 15, 1970 pp. 680-685.
Modis et al., "A ligand-binding pocket in the dengue virus envelope glycoprotein," PNAS, Jun. 10, 2003, vol. 100, No. 12, pp. 6986-6991.
Monath, Thomas, "Dengue: The risk to developed and developing countries," Proc. Natl. Acad. Sci. USA, vol. 91, pp. 2395-2400, Mar. 1994.
Morens et al., "Simplified Plaque Reduction Neutralization Assay for Dengue Viruses by Semimicro Methods in BHK-21 Cells: Comparison of the BHK Suspension Test with Standard Plaque Reduction Neutralization," Journal of Clinical Microbiology, Aug. 1985, vol. 22, No. 2, pp. 250-254.
Mosmann, Tim, "Rapid Calorimetric Assay for Cellular Growth and Survival: Application to Proliferation and Cytotaxicity Assays," Journal of Immunological Methods, 65 (1983), pp. 55-63.
Mukhopadhyay et al., "A Structural Perspective of the Flavivirus Life Cycle," Nature Reviews, Microbiology, vol. 3, Jan. 2005, pp. 13-22.
Neels et al., "The Second and Fourth Cluster of Class A Cysteine-rich Repeats of the Low Density Lipoprotein Receptor-related Protein Share Ligand-binding Properties," The Journal of Biological Chemistry, vol. 274, No. 44, Issue of Oct. 29, pp. 31305-31311, 1999.
Pantoja-Uceda et al., "De novo Design of Monomeric Beta-Hairpin and Beta-Sheet Peptides," Methods in Molecular Biology, vol. 340: Protein Design: Methods and Applications, pp. 27-51, 2006.
Reyes Barcelo et al., "Soluble aggregates of the amyloid-beta peptide are trapped by serum albumin to enhance amyloid-beta activation of endothelial cells," Journal of Biological Engineering Apr. 27, 2009, 3:5.
Rey et al., "The envelope glycoprotein from tick-borne encephalitis virus at 2 Angstrom resolution," Nature, vol. 375, May 25, 1995, pp. 291-298.
Sabate et al., "Native Structure Protects SUMO Proteins from Aggregation into Amyloid Fibrils," Biomacromolecules May 4, 2012, 13, pp. 1916-1926.
Sagis et al., "Mesoscopic Properties of Semiflexible Amyloid Fibrils," Langmuir 2004, 20, pp. 924-927.
Santiveri et al., "Context-Dependence of the Contribution of Disulfide Bonds to Beta-Hairpin Stability," Chem. Eur. J. 2008, 14, pp. 488-499.
Schneider et al., "Sequence logos: a new way to display consensus sequences," Nucleic Acids Research, vol. 18, No. 20, pp. 6097-6100, 1990.
Schymkowitz et al., "The FoldX web server: an online force field," Nucleic Acids Research, 2005, vol. 33, Web Server Issue pp. W382-W388.
Stanger et al., "Length-dependent stability and strand length limits in antiparallel beta-sheet secondary structure," PNAS, Oct. 9, 2001, vol. 98, No. 21, pp. 12015-12020.
Studier et al., "Use of Bacteriophage T7 RNA Polymerase to Direct Selective High-level Expression of Cloned Genes," J. Mol. Biol. (1986) 189, pp. 113-130.
Studier, William, "Protein production by auto-induction in high-density shaking cultures," Protein Expression and Purification 41 (2005) pp. 207-234.
Sukupolvi-Petty et al., "Type- and Subcomplex-Specific Neutralizing Antibodies against Domain III of Dengue Virus Type 2 Envelope Protein Recognize Adjacent Epitopes," Journal of Virology, Dec. 2007, vol. 81, No. 23, pp. 12816-12826.
Swindells et al., "Intrinsic phi, psi propensities of amino acids, derived from the coil regions of known structures," Nature Structural Biology, vol. 2, No. 7, Jul. 1995, pp. 596-603.
Thullier et al., "Mapping of a dengue virus neutralizing epitope critical for the infectivity of all serotypes: insight into the neutralization mechanism," Journal of General Virology (2001), 82, pp. 1885-1892.
Vriend, G., "What If: A molecular modeling and drug design program," J. Mol. Graphics, 1990, vol. 8 March pp. 52-56.
Modis et al., "Structure of the dengue virus envelope protein after membrane fusion," Nature, vol. 427, Jan. 22, 2004, pp. 313-319.
Modis et al., "Variable Surface Epitopes in the Crystal Structure of Dengue Virus Type 3 Envelope Glycoprotein," Journal of Virology, vol. 79, No. 2, Jan. 2005, pp. 1223-1231.
Matsui et al., "Characterization of dengue complex-reactive epitopes on dengue 3 virus envelope protein domain III," Virology 384 (2009) pp. 16-20.
Lin et al., "Infection of Five Human Liver Cell Lines by Dengue-2 Virus," Journal of Medical Virology 60:425-431 (2000).
Lillis et al., "The low density lipoprotein receptor-related protein 1: Unique tissue-specific functions revealed by selective gene knockout studies," Physiol Rev. Jul. 2008, 88(3), pp. 887-918.
Smith et al., "Measurement of Protein Using Bicinchoninic Acid," Analytical Biochemistry 150, pp. 76-85, (1985).

* cited by examiner

Stock of peptide in water at 580 uM

↓

Dilution of peptide in water to:
- 100 uM
- 50 uM
- 20 uM
- 2 uM

↓

Incubation 2h at 37 °C

↓

Determination of Antiviral Activity

BETA HAIRPIN PEPTIDES HAVING ANTIVIRAL PROPERTIES AGAINST DENGUE VIRUS

This application is the U.S. National Phase of, and Applicants claim priority from, International Patent Application Number PCT/CU2015/000002 filed Feb. 26, 2015, which claims priority from CU-2014-0026 filed Mar. 3, 2014, each of which is incorporated herein by reference.

FIELD OF THE INVENTION

The present invention is related to medicine and the pharmaceutical industry, and in particular to the design and obtainment of synthetic peptides exhibiting antiviral activity against Dengue virus (DENV). The primary structure of these peptides was designed to facilitate the efficient formation of a beta hairpin structure and to mimic functional patches of domain III of the envelope protein (DIIIE) of DENV. The invention is also related to pharmaceutical compositions containing these synthetic peptides, used for the prevention and/or treatment of DENV infections.

STATE OF THE ART

DENV is a member of the Flaviviridae family, composed of enveloped viruses whose genome contains a positive-sense, single-stranded ribonucleic acid (RNA) molecule. There are three different genera in the Flaviviridae family: Flavivirus, Hepacivirus and Pestivirus. Flavivirus encompasses over 70 known viruses of which many cause clinically important diseases, such as Yellow Fever Virus (YFV) and Dengue Virus (DENV). The viruses of the Flavivirus genus that cause human disease are usually arthropod-borne (ticks and mosquitoes), and therefore eradicating these diseases is an extremely difficult task (Monath, T. P., F. X. Heinz. 1996. *Flaviviruses*, p. 961-1034. In: B. N. Fields, D. M. Knipe, P. M. Howley (ed.), *Fields virology*, 3rd ed., vol. 1. Lippincott-Raven Publishers, Philadelphia, Pa.).

DENV infections have reached pandemic proportions in tropical areas of the world, and their recent re-emergence has become an increasingly difficult challenge for the public health systems of affected countries. About 100 million DENV infections are estimated to take place annually, and 2.5 billion persons live in areas where DENV is endemic (Gubler, D. J. (1998). *Clin. Microbiol. Rev.* 11, 480-496; Monath, T. P. (1994) *Proc. Natl. Acad. Sci USA* 91, 2395-2400). During the 1990-1998 period, an average of 514,139 cases and 15,000 deaths due to DENV hemorrhagic fever (DHF) were reported every year to the World Health Organization (WHO), although the actual incidence of DHF is estimated to be several fold higher. No vaccines against DENV are commercially available, and no specific antiviral treatment against this virus exists.

The term DENV actually refers to a complex composed of four antigenically and genetically related viruses or serotypes, denominated DENV1 to DENV4. DENV is transmitted to humans through the bite of a handful of mosquito species, mainly *Aedes aegypti*. The clinical manifestations of the resulting infection may vary from an asymptomatic disease or a mild febrile state to the more severe DHF and the potentially fatal Dengue shock syndrome (DSS). The most severe clinical manifestations are associated with secondary infections where the virus belongs to a serotype different from that of the primary infection (Kouri G P et al. (1987) *Trans Roy Soc Trop Med Hyg;* 72: 821-823; Halstead, S. B (2003). *Adv. Virus Res.* 60:421-67). This observation has been explained through the theory of antibody-dependent enhancement, which states that viral infectivity may be actually enhanced through the formation of non-neutralizing virus-antibody complexes, which would afford the infecting virus an additional port of entry to the target cells via Fc receptors (Halstead S B. (1988). *Science;* 239: 476-481).

The first step of the viral replication cycle is the binding of virions to the surface of their host cell. It has been shown that DENV virions bind cell surface glycosaminoglycans, and these have been proposed as molecules mediating an initial interaction of infecting viruses with the target cell. Another molecule DENV has also been shown to bind is DC-SIGN (dendritic cell-specific intercellular adhesion molecule-3-grabbing non-integrin), a dendritic cell-specific type C lectin. However, it is thought that both molecules play a passive role, accumulating viruses in the cell surface or propitiating their dissemination in vivo to secondary sites of infection. A productive virus entry requires receptor-mediated endocytosis via subsequent interactions with additional high-affinity receptors or co-receptors, resulting in the internalization of the infecting virions. Once the latter reach the endocytic compartment, the consequent drop in pH triggers the process of fusion of the viral envelope and endosomal membrane, which is mediated by structural changes in the viral fusion protein. The final outcome of this fusion is the release of viral capsids into the cytoplasm, followed by the release of their genomic RNA. Naked cytoplasmic viral RNA then interacts through its 5' untranslated region (5'UTR) with ribosomes, and the single open reading frame (ORF) it contains gets translated into a precursor viral polyprotein. In the Flavivirus genus, this polyprotein precursor contains three structural proteins (capsid (C) membrane (prM) and envelope (E)) and five non-structural proteins (NS1-5) which are obtained by co- and post-translational modification by viral and host cell proteases. The viral RNA-dependent RNA polymerase produces single-stranded antisense RNA copies, which then function as templates for the synthesis of positive-sense single-stranded genomic RNA. It has been shown that the viral proteins involved in the process of replication of its RNA are physically associated to membrane structures, probably related to the endoplasmic reticulum (ER).

After replication, DENV genomic RNA associates with the capsid protein and, through the membrane of the rough ER or in virus-induced membrane structures, the resulting capsids bud into the ER lumen, already covered with the lipid membrane envelope containing viral proteins. These immature virions then enter the secretory pathway, and are eventually released to the extracellular space as mature virions. As mentioned above, the DENV genome is an approximately 11 kb long single-stranded positive sense RNA molecule (Hencha, E. A. & Putnak, J. R. (1990). *Clin. Microbiol. Rev.* 3, 376-396) containing an ORF whose exact length varies between different viral serotypes and even between strains of the same serotype (Yabar V, C. (2003). Rev. Perú. *Med. Exp. Salud Publica* 20, 51-57). The 5' proximal quarter of this ORF codes for structural proteins, and the remainder codes for non-structural polypeptides (Lindenbach, B. D. & Rice, C. M. (1999). *J. Virol.* 73, 4611-4621). Protein E of DENV and every other flavivirus plays a fundamental role in the binding of mature virions to cellular receptors, membrane fusion during viral entry and virion assembly. Hence, it influences a number of fundamental virus characteristics, such as host range, virulence and the induction of protective immunity (Modis, Y., et al. (2005). *J. Virol.* 79, 1223-1231).

Protein E has a molecular weight ranging from 53 to 54 kDa. It is the most conserved of all DENV structural polypeptides, exhibiting an inter-serotype similarity of 60-70%. It has been shown through X-ray crystallography (Modis, Y., (2003). *Proc. Natl. Acad. Sci. U.S.A* 100, 6986-6991) as well as electron cryo-microscopy studies (Kuhn, R. J., et al. (2002). *Cell* 108, 717-725) that in DENV, as in other flaviviruses, protein E forms dimers in the surface of mature virions.

Exposing DENV virions to a slightly acid pH (i.e. lower than 6.5) induces an irreversible conformational shift in protein E that dissociates these dimers and leads to the re-association of the resulting monomers into trimers. This conformational change is necessary for the fusion of viral and endosomal membranes that takes place after the internalization of DENV virions by receptor-mediated endocytosis in mammalian cells (Modis, Y., et al. (2004). *Nature* 427, 313-319).

Out of the approximately 500 amino acid residues of each protein E monomer, 80% form part of its N-terminal ectodomain and the remainder form a transmembrane domain that anchors E to the lipid envelope (Chambers, T. J., et al. (1990). *Annu. Rev. Microbiol.* 44, 649-688). This transmembrane domain is linked to the ectodomain through a stem of approximately 53 residues (Modis, Y., et al. (2004). *Nature* 427, 313-319). The E ectodomain in turn folds into three separate structural domains: a central beta-sheet domain (domain I), an elongated dimerization domain (domain II) and a third domain with an immunoglobulin-like fold, domain III (DIIIE) (Modis, Y., et al. (2003). *Proc. Natl. Acad. Sci. U.S.A* 100, 6986-6991).

DIIIE is the only protein E domain formed by a continuous, uninterrupted segment of its polypeptide chain. DIIIE is found at the C-terminal end of the protein E ectodomain, between residues 294 and 392. Its structure is very similar to that of the globular domains of immunoglobulin constant regions (Modis, Y., et al. (2005). *J. Virol.* 79, 1223-1231). The tertiary structure of DIIIE includes a disulphide bond between two Cys residues at positions 302 and 333 that are strictly conserved among all flaviviruses.

DIIIE connects to domain I through an extended, flexible 10-residue linker (Modis, Y., et al. (2004). *Nature* 427, 313-319) that lets DIIIE adopt different orientations relative to the remaining domains (Rey, F. A., et al. (1995). *Nature* 375, 291-298). During the dimer-to-trimer transition, DIIIE is the domain exhibiting the most drastic structural shifts, as it rotates approximately 70° and its center of mass moves 36 Å towards domain II. In DENV and other flaviviruses, a large portion of the residues determining virulence, cell tropism and viral host range are located in DIIIE (Rey, F. A., et al. (1995). *Nature* 375, 291-298). Likewise, many neutralization escape mutations map to this domain (Modis, Y., et al. (2005). *J. Virol.* 79, 1223-1231).

There is plenty of evidence, obtained both from the analysis of the structure of protein E and DENV virions and from experimental work, supporting the notion that DIIIE is part of the region of protein E that interacts with the putative DENV cell receptor. Some of the structural characteristics of this domain consistent with such a role are the fact that DIIIE is the most protruding domain in the virion surface, and therefore the most accessible for interaction with receptor sites (Mukhopadhyay, S., et al. (2005). *Nat. Rev. Microbiol.* 3, 13-22). Also, the very fact that it adopts an immunoglobulin-like fold suggests that it may engage the putative DENV cell receptor, as similar domains have long been known to be found in a wide variety of cell adhesion proteins. Yet another structural feature of this domain consistent with a possible involvement in receptor binding is the presence of positively charged hydrophilic surface patches, formed by residues 284-310 and 386-411, which might participate in binding of this domain to negatively charged heparin sulfate molecules (Modis, Y., et al. (2005). *J. Virol.* 79, 1223-1231).

Studies with DIIIE, obtained through recombinant deoxyribonucleic acid (DNA) technology, showed that they bound directly to the surface of cells of the C6/36 and BHK21 lines, where they were able to block viral infection (Hung, J. J., et al. (2004). *J. Virol.* 78, 378-388).

Previous studies have demonstrated that DIIIE exhibits specific binding to host cells with an apparent dissociation constant ($K_D$) of 30 μM or less, depending on the flaviviral species from which DIIIE is obtained (Halstead, S. B., et al. (2005). *Vaccine* 23, 849-856). On the other hand, it is known that the monoclonal antibodies (mAb) most efficiently blocking the binding of DENV to its target cells are those whose epitope is located in DIIIE, providing indirect evidence for the involvement of this domain in the interaction of protein E with viral cell receptors (Thullier, P., et al. (2001). *J. Gen. Virol.* 82, 1885-1892.).

The entry of DENV into its host cells depends on its previous interaction with specific receptor molecules on the cell surface. However, according to the evidence gathered during the study of DENV-host cell interactions, which exact receptor gets used for viral entry may vary, depending on cell type and even virus serotype. The existing data suggest that DENV entry involves an interaction with a multi-molecular complex, where some molecules perform the role of primary receptors, binding and concentrating the virions on the cell surface for later interaction with the putative endocytic receptor.

Blocking viral entry into the cells is an attractive strategy for developing an antiviral treatment, as it would target the very first stage of the viral lifecycle and would, if successful, block all other downstream events of the viral infection. Analysis by X-ray crystallography and nuclear magnetic resonance spectroscopy has provided structural information at atomic resolution on the three structural proteins of the Flavivirus genus (protein C, protein prM and protein E). These studies have suggested alternative approaches to inhibit the viral replication cycle like the inhibition of structural transitions of the envelope protein. Similarly, some structural studies have provided data concerning specific regions of the envelope protein involved in interaction with receptor molecules and neutralizing antibodies, which constitute potential binding sites as targets for rational design of antiviral drugs against DENV.

It has been previously proposed that a human membrane protein denominated Low Density Lipoprotein Receptor-Related Protein (LRP1) is the actual endocytic receptor used during DENV entry (Huerta V. et al, *WO* 2007/124698). LRP1 would, therefore, constitute an attractive target for the design of antiviral drugs, as this molecule efficiently mediates the endocytosis of over 30 natural ligands, and has been previously shown to act as a receptor to an unrelated viral species, the minor group of human Rhinoviruses. LRP1 has been shown to bind DIIIE both directly and through bridging molecules that interact simultaneously with LRP1 and the virus. One example of the latter case is human alfa-2-macroglobulin (α2M), which binds DIIIE and is also an LRP1 ligand.

It has previously been shown that beta hairpin peptides based on the structure of DIIIE can be used to inhibit DENV infection both in vitro and in vivo (Huerta V. et al, *WO* 2007/124698). These peptides, whose exact sequence depends on the viral serotype from which they are derived, encompass part of the FG beta hairpin of DIIIE, and are stapled through a disulphide bridge between cysteine residues appended at the N- and C-termini of the selected hairpin fragment. Out of this series of peptides, the member exhibiting the highest antiviral activity was peptide HDIII3CL which, although derived from DENV3 DIIIE, exhibits inhibitory activity against all four DENV serotypes.

These stapled beta hairpin peptides do, however, have important disadvantages, such as a relatively low potency. For instance, the 50% inhibitory concentration ($IC_{50}$) of HDIII3CL, determined through infection inhibition assays in Vero cells, is 15 µM for DENV1, 20 µM for DENV2 and DENV3, and 40 µM for DENV4. This relatively poor potency precludes direct use of these molecules for clinical development, as good drug leads must have potencies at least in the submicromolar range, and preferably in the nanomolar range, or better.

Another disadvantage of this peptide series is that the inter-strand part of the loop contains a neutralizing, immunodominant B-cell epitope (Matsui K, et al. (2009) *Virology* 384(1):16-20). Document Huerta V. et al, *WO* 2007/124698, for instance, demonstrates that the neutralizing mAb 3H5 binds peptides containing this inter-strand loop. Since part of the anti-DIIIE antibody response is cross-reactive among different serotypes, there exists the possibility that a pre-existing cross-reactive anti-DIIIE antibody response, induced by a previous infection, might bind this peptide and decrease its effective concentration, thereby requiring even higher therapeutic dosages of the peptide than those already required by their low potency.

The facts presented above demonstrate that no high-potency antiviral drugs against DENV, with $IC_{50}$ preferably in the nanomolar range, are yet available. The present invention addresses exactly this unmet need.

DESCRIPTION OF THE INVENTION

The present invention solves the problem mentioned above by providing new DENV-inhibiting beta hairpin peptides obtained by optimizing the potency of previously identified peptides. The beta hairpin peptides of the present invention are characterized by having one of the amino acid sequences presented in SEQ ID No. 1 to SEQ ID No. 9, or a sequence analogous to these sequences.

A central objective of the present invention is to design peptides inhibiting DENV infection with a relatively high potency, at least in the submicromolar range, and preferably at the nanomolar range or better. High potencies are necessary to decrease as much as possible the therapeutic dose. Therapeutic synthetic peptides currently in clinical use against other pathologies are typically very potent compounds, whose effectiveness ($IC_{50}$, 50% effective concentration (EC50), etc.) sits at the nanomolar/subnanomolar range and whose specificity is very high, exhibiting therefore very low toxicity. A low potency peptide would require high therapeutic dosages, which bring along a number of important disadvantages. One of them is the fact that high doses increase the possibility that the drug will exhibit side effects due to non-specific interactions. Another, that the probability of having aggregation problems, either during manufacture and formulation or during its delivery in vivo (due e.g. to non-specific interactions with serum proteins) increases significantly. Yet another is the fact that high doses increase the probability of having immunogenicity/antigenicity problems, where the induction of an anti-peptide antibody response neutralizes its therapeutic activity, especially if the treatment is repeated or prolonged in time, thereby requiring even higher doses to compensate for this loss.

In contrast, the use of high potency peptides with low effective doses exhibits a number of economic advantages, stemming both from lower manufacturing costs and lower prices to be paid by the patients. Peptide synthesis technology is usually much more expensive than the synthesis of drugs based on small molecular weight compounds, and cost considerations may ultimately limit the number of patients or persons with access to peptide-based antiviral drugs against dengue, especially if therapeutic doses are large.

One of the fundamental factors determining the potency of a therapeutic peptide is the affinity of its interaction with its target. However, the task of designing active peptides that mimic the functional surface patches involved in high-affinity protein-protein interactions is far from trivial. The fundamental problem here is that functional surface patches in globular proteins are usually topographic (i.e. involving more than one continuous segment of the polypeptide chain) and conformational (i.e. requiring a well-defined spatial arrangement of the participating residues for the interaction to take place). In contrast, peptides derived from short protein segments, typically 10-20 residues long, are flexible in solution and usually do not adopt one single well-defined conformation. Beta hairpin peptides, for instance, despite being derived from a well defined structural motif in a folded protein, are not structurally stable in solution, existing instead as an ensemble of different conformations in equilibrium.

The conformational status of a peptide in solution intended to mimic a particular conformation is usually analyzed as an equilibrium between two states: the folded state (whose tri-dimensional structure matches the native protein structure it is supposed to mimic) and the unfolded or denatured state (the ensemble of all non-native conformations adopted by the peptide in solution). In the case of a beta hairpin peptide mimicking the interaction between a beta hairpin in a native protein and a separate protein target, the more stable the hairpin is, the more its structure will resemble that of the corresponding segment in the native protein, and the higher the affinity of the resulting interaction due to smaller losses in conformational entropy upon formation of the peptide-receptor complex.

In other words: assuming that a peptide in solution adopts a disordered structure, and assuming that the process of binding to its target proceeds through a conformational selection mechanism, then the variation in free energy of the binding process can be expressed as the sum of the variation in free energy associated to the folding of the peptide into the appropriate conformation and the variation in free energy associated to the binding of the already folded peptide to its docking site on the receptor. In that case, the amount of free energy released by the binding process, or in other words, the stability of the interaction, can be increased by modifying the sequence of the peptide, replacing some residues of the original sequence by other residues that either a) enhance the conformational stability of the peptide in solution (especially convenient when the selected residues do not interact directly with the contact surface at the receptor site) or b) optimize the intermolecular interactions between the peptide and its receptor, increasing the drop in free energy that takes places during the docking step.

An analysis of the sequence of peptide HDIII3CL (SEQ ID No. 10, Table 1) reveals several characteristics that can be taken advantage of to improve the stability of its beta hairpin fold. These are: a) the presence of asparagine residues—such as Asn3 and Asn16—on beta strands F and G. Asparagine is a poor beta-sheet former, with a very low intrinsic beta sheet propensity and a tendency to appear in loops and backbone structures characterized by positive torsion angles (Swindells M B, et al. (1995). *Nat Struct Biol.;* 2(7):596-603); b) the presence of a rather large loop—six residues from strand to strand, much larger (by four residues) than the optimum size of two (Branden C. & Tooze J. *Introduction to protein structure.* New York: Garland Publishing, 1991). The problem here is that the insertion of new residues into protein loops has an entropic cost associated with loop closure, which grows with loop size; and c) the presence of two glycine residues—Gly7 and Gly9—in the inter-strand loop. Glycine is the residue suffering the largest conformational entropy loss during the folding process, as it is not subject to the backbone torsion angle restrictions associated with the other natural amino acids.

The basis of the sequence changes presented in the current invention, which increase the conformational stability of the disclosed beta hairpin peptides, is to replace existing residues at modifiable positions by residues with a higher structural propensity for the formation of beta hairpin-type structures. The structural propensity of a particular amino acid to occupy a specific position in a beta hairpin can be estimated from the frequency of appearance of said amino acid at that position among experimentally determined beta hairpin structures from protein structure databases. Mathematically, it is calculated as the logarithm of the quotient between its observed and expected frequencies of appearance, deriving the latter from the relative abundance of the relevant residue in the database.

The positions defined as modifiable in the present invention are:
a) Positions in the first beta strand of the beta hairpin peptide that correspond to residues of the internal face of strand F in the structure of DIIIE, that is, residues not exposed to the solvent in the native structure. These residues occupy positions (HB positions) where hydrogen bonds between donor and acceptor atoms in the backbones of the first and second beta strand (corresponding to strand G in the structure of DIIIE) of the peptide are established;
b) The positions corresponding to the inter-strand loop;
c) HB positions in the second beta strand of the peptide (corresponding to strand G of DIIIE), excepting that of residue Trp391 of DIIIE (DENV2 ordinates), which will remain invariable. At the rest of these "c" positions, residues with hydrophobic character are allowed and preferred.
d) The non-HB (NHB) positions of strand F closest to the loop;
e) Possible modifications for the first HB position of the second strand of the peptide (corresponding to strand G in DIIIE) include, in addition to residues with high structural propensity, its replacement by a Lys residue that would mimic the role of a lysine (Lys385, DENV2 ordinates) that is topographically conserved among DIIIE of all four serotypes and may potentially be engaged during binding to the LRP1/α2M* (activated α2M) complex.

The modifiable residues of the present invention defined in point a) are not solvent-accessible in the structure of DIIIE, and therefore are not part of the contact interface between the domain and its receptor or any other relevant receptors during the viral lifecycle. They can therefore be replaced by residues increasing the folding stability of the peptide.

The residues of the inter-strand loop defined in point (b) are considered modifiable because the sequence of this region varies between DENV serotypes, indicating that strict conservation of these residues is not necessary to preserve the interaction of DIIIE with the putative DENV receptor. This line of reasoning is supported by the fact that peptide HDIII3CL inhibits the infection of all four DENV serotypes, and that in general, blocking the α2M*/LPR1 receptor has a serotype-independent antiviral effect. The inter-strand loop variant preferred by this invention consists of the two central residues of a beta turn where positions 1 and 4 of the turn would correspond to the first connecting residue of the adjacent beta strands, as such a variant would increase the conformational stability of the peptide. In general, natural beta hairpins tend to have short connecting loops (Branden C. & Tooze J. New York: Garland Publishing, 1991), and a reduction in loop size concomitantly reduces the conformational entropy of the denatured state, which increases with the size of the polypeptide chain.

One of the two central residues of the two-residue loop (preferred size for the inter-strand loop in the present invention) can take on a functional role by mimicking Lys385 of DIIIE from DENV3. In some of the peptides disclosed in the present invention, this functional role is performed by a lysine residue at position 2 of the loop in the case of type IIP beta turns (this Lys residue would thus occupy the central position of the turn) whose topology were identical to that of the FG hairpin of DIIIE. In another of the peptides disclosed by the present invention, this functional role is fulfilled by a D-Lys residue (a D stereoisomer of L-lysine) placed at position 1 of the loop (position 2 in type IIP beta turns), although in this case, the topology of the peptide is reversed relative to that of the FG beta hairpin in DIIIE.

The modifiable residues defined in point (c) are oriented to the same face of the hairpin as those of point a), to which they are therefore adjacent, and with which they form hydrogen bonds involving backbone atoms. The corresponding residues in the structure of DIIIE are partially solvent-exposed, as strand G forms the edge of the beta sheet. The position in the beta hairpin peptide corresponding to that of Trp391 (DENV2 ordinates) in DIIIE is defined as non-modifiable in the present invention, as this residue is strictly conserved across all DENV serotypes and is, very likely, functional. Indeed, Example 2 (Table 2) demonstrates that this residue is essential for the antiviral activity of peptide HDIII3CL (and that of peptide HDIII3CL2 as well, see Table 1), and is lost upon its replacement by an alanine residue. A lysine substitution is also allowed at the first position of the second strand (modifiable residue referred to in point e)), as such a substitution would constitute a structural/functional mimic of residue Lys385 of DIIIE of DENV3. Lys385 is a cationic residue involved in the interaction of DIIIE with α2M*, one of the constituent proteins of the putative α2M*/LRP1 endocytic receptor complex.

Although the modifiable positions referred to in point d) correspond to residues in the solvent-exposed surface of DIIIE, these are still defined as modifiable because they are not strictly conserved across DENV serotypes (FIG. 1E).

Once the set of modifiable positions in peptide HDIII3CL was defined, its sequence was optimized by selecting, for each modifiable position, the residue with the highest structural propensity index. This parameter, as mentioned above, is derived from the observed frequency of appearance of each residue in 8-residue fragments adopting a beta hairpin structure with a central 2-residue loop (that is, residues 4 and 5 of the fragment would correspond to the central residues of a beta turn), taken from databases of experimentally determined protein structures. The database used in this instance was a non-redundant set of tridimensional protein structures with a resolution higher than 2.5 Å (WHAT IF database; Vriend, G. (1990), *J. Mol. Graph.* 8, 52-6). The structural propensity index was defined as the logarithm of the quotient between the number of occurrences of a particular amino acid at a particular position in the hairpin and the expected number of occurrences based on the relative abundance of the residue in the database, and was calculated separately for beta hairpins containing type IP and IIP beta turns. The final selection required building models of the tridimensional structures of the proposed beta hairpin peptides, taking into account the most common side chain rotamers and inter-strand contacts.

The present invention also discloses the introduction of non-natural amino acids into positions of the beta hairpin that are structurally compatible with their chemical structure and stereochemistry. Such is the case of D-stereoisomers of natural amino acids, introduced into positions adopting positive backbone torsion angles. D-Pro, for instance, is favorable as the second residue of type IIP beta turns (equivalent to the first residue of a 2-residue inter-strand loop in the present invention). Another example is D-Lys, also introduced into the position corresponding to the second residue of a type IIP beta turn, but in peptides with a reversed topology. In these cases, L-Lys is not structurally favored for this position (its structural propensity index is not high, reflecting the fact that Lys is not good at adopting torsion angles located at the right bottom quadrant of the Ramachandran plot), which is unfortunate in light of the fact that a Lys residue in this position would potentially mimic Lys285 of DIIIE from DENV3. Introducing a D-Lys residue instead solves this conundrum, as it can easily adopt the torsion angles required for position 2 of type IIP beta turns.

The definition of modifiable residues, as described in the paragraphs above, corresponds to beta hairpin turns whose topology is identical (native topology) to that of beta hairpin FG in the structure of DIIIE. However, the present invention also discloses peptides with the reverse topology. In these peptides, the first and second beta strand of the sequence correspond, functional and structurally, to strands G and F of DIIIE, respectively, and the residues occupying NHB positions correspond to HB positions in native topology peptides (and vice versa).

The peptides designed here that maintain the native topology of the FG beta hairpin of DIIIE include a disulphide bridge at an NHB position, which increases the conformational stability of beta hairpin structures. The positions occupied by these Cys residues are: a) the first residue of strand F and b) the last residue of strand G (FIG. 1E).

Several of the peptides disclosed in the present invention exhibit longer beta strands than those of peptide HDIII3CL. These longer strands increase the conformational stability of the peptide, as they introduce two additional hydrogen bonds (one HB residue per strand).

In addition to stabilizing their conformation, the affinity of the interaction of the disclosed peptides with their target (and hence, their antiviral activity) can also be increased by directly optimizing said interaction. This can be done by modifying interface residues whose contribution to the energetics of the interaction is either negligible or actually negative.

In general, it has been found that the energetics of protein-protein binding is dominated by the interactions of a rather small set of residues. Hence, most interface residues play a relatively limited role in the binding process, if at all. Although no structural data are available about the interaction between the peptides disclosed in this invention and their target, or about the interaction between DIIIE and its putative receptor, it can be assumed, as a first approximation, that every solvent-exposed residue of the FG hairpin of DIIIE is engaged and/or plays a functional role in the peptide-receptor interface.

Examples 2 (Table 2) and 6 of the present invention demonstrate that replacing Lys14 (corresponding to Lys388 in DENV3 DIIIE) or Trp17 (corresponding to Trp391 in DIIIE) of peptide HDIII3CL2 by an alanine residue abolishes in either case the antiviral activity of this peptide in Vero cells and affects its binding to the LRP1 receptor. Both residues are hence essential for the biological activity of HDIII3CL2 and are very likely located at the interface, making essential contributions to the interaction. Therefore, none of these residues are substituted in the present invention. A double substitution of residues Cys1 and Cys18 by alanine also abolishes the antiviral activity and binding to LRP1 of HDIIICL2, but the effect in this case is thought to be caused by the loss of conformational stability in solution of the beta hairpin rather than the loss of favorable intermolecular interactions.

The present invention also discloses that extending the potentially functional surface of beta hairpin peptides constitutes an additional means for increasing their potency. In this particular case, four residues are added to the structure of the hairpin, of which two correspond to the exposed face of the FG hairpin in DIIIE and had not been previously included in the HDIII3CL series of analogue peptides. Specifically, two residues are added to each beta strand, where NHB positions are occupied by the amino acids corresponding to residues 375 (F strand) and 392 (G strand) of DENV3 DIIIE. Although in DIIIE the identity of position 375 is not strictly conserved across all four serotypes, since either Asp or Glu are observed in different isolates, this is a conservative substitution. Therefore, both amino acids are eligible for the equivalent position of the beta hairpin peptides disclosed in the present invention, although Glu is the preferred solution due to the lower propensity of Asp to be part of extended conformations such as beta sheets. In the case of the peptide position equivalent to residue 392 of DIIIE, the preferred amino acids are Phe or Tyr, which are the residues most frequently observed at this position among the four DENV serotypes. The modifiable residues of these extended portions of the hairpin then correspond to the HB positions, which would be used to optimize conformational stability by including preferentially hydrophobic amino acids with high beta sheet forming propensities.

Excepting the essential residues disclosed in Example 2 (those corresponding to Lys388, Trp391 and Glu/Asp392 in DIIIE), all remaining residues of the external face (NHB positions) are considered modifiable in the present invention, as their corresponding amino acids in DIIIE exhibit more variability across DENV serotypes.

Concerning the residue type selectable for the modifiable positions of the beta hairpin peptides of the present invention, the preferred solutions are those residue types which appear at the corresponding positions of homologous sequences of the four serotypes of DENV. Such is the case of the residue corresponding to position 377 in DIIIE, where the preferred solution is Tyr (appearing in DIIIE from DENV1 and DENV4) rather than Asn (appearing in DIIIE from DENV3). Although both Tyr and Asn are polar and hydrogen bond donor/acceptors, Tyr exposes a larger non-polar surface and appears more frequently at protein-protein interaction interfaces, has a higher propensity for adopting extended structures and forming part of beta strands, and may contribute a more favorable (pi-cation) interaction with the residue corresponding to Lys388 from DIIIE, thus contributing to the conformational stability of the beta hairpin.

Non-essential but potentially functional positions can usually be identified through combinatorial methods, such as the use of phage peptide libraries where essential/structural positions have been fixed and the remaining positions have been randomized. In this case, the library is screened for optimal sequences through the use of binding assays that select those phage expressing high-binding peptides to a specific ligand, such as LRP1 and/or α2M*. Optimal sequences can also be obtained through the use of rational design methodologies.

For the purposes of the present invention, the disclosed beta hairpin peptides may be synthesized chemically or, if their sequence contains only natural amino acids, through recombinant DNA technology, either alone or as fusion proteins. The use of fusion proteins, should recombinant DNA technology be applicable, may increase expression levels and the stability of the recombinant peptide against host proteases. The peptide may be bound to its fusion partner through a protease recognition site, which can then be used to release the peptide by treatment with the cognate protease.

Example 1 of this invention discloses the design of nine beta hairpin peptides (SEQ ID No. 1-SEQ ID No. 9). Basically, their structure consists of four segments: two beta-strand segments (structurally analogous to the FG hairping of DIIIE), separated by a beta turn and followed by a C-terminal cationic extension containing three lysine residues. These peptides were designed following the structural/functional criteria discussed above for optimizing their antiviral potency and their binding to cellular receptors.

For the purposes of the present invention, a peptide sequence is considered to be analogous to that of the herein disclosed beta hairpin peptides (peptides PHB1-9 of table1, SEQ ID1-9) if the sequence identity of said peptide to at least one of the sequences of the PHB1-9 beta hairpin peptides is equal to or higher than 70%, and preferably 80%. The sequences of said analogous peptides differ from one another in one or several positions, selected from: 1) modifiable positions a)-e) described above, where a particular residue or residues in PHB1-9 is/are substituted by residues which also exhibit a high structural propensity for occupying that position in beta hairpins; 2) the potentially functional positions described above, whereby the relevant position(s) in PHB1-9 is/are occupied instead by a residue or residues of the FG hairpin of DIIIE from a particular DENV serotype, wherein said residues(s) occupy an analogous position in the beta hairpin of PHB1-9 peptides; 3) positions corresponding to residues of the C-terminal lysine tag; in this case, the tag may comprise two or three lysine residues, preferably three; and 4) positions corresponding to the cysteines forming the disulfide bonds of peptides PHB1-4 and PHB7-9, wherein one Cys residue may be replaced by Asp/Glu as long as the opposing Cys residue is replaced by Lys, such that the peptide is stapled through the formation of an amide bond between the side chains of said residues, that is Asp/Glu on one side and Lys on the other.

The activity of the PHB1-9 peptides was evaluated in a plaque inhibition assay on Vero cells, whose results are shown in Example 2. All of them exhibited antiviral activity in this experimental model, six of them at higher levels than peptide HDIII3CL. Peptide PHB4 in particular exhibited a very potent antiviral effect at the nanomolar range against all four DENV serotypes, with very good selectivity indexes (1290 to 6450, depending on the specific serotype). Hence, this peptide constitutes an excellent lead molecule for the development of antiviral drugs against DENV, with a better potency than previously reported antiviral drug candidates.

The present invention, therefore, also discloses a pharmaceutical composition comprised of one or more beta hairpin peptides with an amino acid sequence selected from those presented in SEQ ID No. 1 to SEQ ID No. 9, or an analogous sequence thereof, and at least one pharmaceutically acceptable excipient.

In one embodiment of the present invention, the peptides comprising said pharmaceutical composition are forming supramolecular aggregates. Since peptide PHB4 (and, in general, the beta hairpin peptides disclosed in the presence invention) is a molecule that is designed to adopt the structure of an amphiphilic beta strand, it can form supramolecular aggregates depending on peptide concentration and exact solvent composition.

Example 5 shows how the peptide self-assembles into nanostructures, whose size and form depend on experimental conditions such as peptide concentration, temperature, solvent, solution age, presence of different additives, etc. The antiviral activity of this peptide may change, depending on these conditions.

In the context of the present invention, the term 'supramolecular aggregates' is intended to denominate aggregates formed by several peptide molecules, preferably more than 10.

Example 8 shows how the addition of human serum albumin (HSA) at specific time points after peptide PHB4 is dissolved into saline produces formulations with potencies at the low nanomolar/subnanomolar range. This result indicates that it is possible to formulate the peptide in the presence of HSA, and that the presence of this protein leads to the formation of peptide:HSA complexes exhibiting very high antiviral activity. This is an important finding from a pharmacokinetic point of view if the peptide is to be developed into an antiviral compound, as not only is the serum half-life of HSA very long, but HSA may protect the peptide against serum proteases and unwanted interactions with other serum constituents. Therefore, in one embodiment of the present invention, the pharmaceutical composition comprised of the disclosed beta hairpin peptides also contains HSA.

Regardless of the presence of HSA, the fact that peptide PHB4 self-assembles into nanoparticles is a desirable characteristic from pharmacokinetic and pharmacodynamic points of view. Owing to their size, nanoparticles tend to exhibit longer serum half-lives than monomeric peptides, which are usually cleared and metabolized in a very short time span. In addition, monomeric peptides are very susceptible to proteolytic attack by host proteases, against which their assemblage into nanoparticles tends to provide some protection. Also, nanoparticles offer a structural context on which there would be multiple binding sites in a single entity, which may lead to avidity effects due to multivalent binding and thus, a higher apparent affinity for the peptide-receptor interaction or, in other words, better antiviral potency.

Examples 3 and 6 demonstrate that the beta hairpin peptides of this invention can bind the α2M* and LRP1 proteins, which are components of the putative endocytic receptor for DENV and would, therefore, constitute a target for the development of antiviral compounds, as reported in Huerta H. et al, WO 2007/124698.

An essential part of the present invention is the analysis of the biological activity of the disclosed beta hairpin peptides at the nanomolar range. As shown in Example 3, peptides PHB2, PHB4, PHB5, PHB8 and PHB9 inhibit the binding of a biotinylated variant of recombinant DENV1 DIIIE (Jamaica strain; DIIIE1Jbiot) to protein α2M* at the nanomolar/submicromolar range, and said inhibitory capacity is clearly higher than that exhibited by non-biotinylated DIIIE (DIIIE1J), since their inhibition percentages are 1.5- to 3-fold higher than that of DIIIE1J. In contrast, the inhibitory capacity exhibited by HDIII3CL at this concentration range is very low, compared to DIIIE1J. Example 6 demonstrates that the beta-hairpin peptides of the present invention bind receptor LRP1 with high avidity, and that peptide PHB4 exhibits the highest avidity in this regard. This result is coherent with the fact that PHB4 was also the most potent peptide on antiviral activity assays.

Example 8 demonstrates that the antiviral effect of beta hairpin peptides correlates with their ability to bind receptor LRP1 and protein α2M*, solidly supporting the notion that these peptides exert their antiviral effect by inhibiting the entry of DENV to its target cells. This result also underscores the rationality of the strategy disclosed in this invention for optimizing the antiviral potency of the beta hairpin peptides.

The capacity of the beta hairpin peptides disclosed in the present invention for binding protein α2M* and receptor LRP1 can be harnessed to develop therapeutic agents for the control of diseases or clinical conditions mediated by these proteins. Their potent inhibition of DENV infection, as disclosed in the present invention, constitutes one example of that possibility.

Blocking the binding of DENV (in other words, inhibiting the binding of protein E) to the putative endocytic receptor α2M*/LRP1 is a better choice for developing antiviral drugs against this virus than the other receptors known in the state of the art. The receptors described by other authors are adhesion receptors, that is, they mediate the binding of the virus to the cytoplasmic membrane, but do not internalize the virus by endocytosis. Since the stage inhibited by the peptides disclosed in the present invention is located downstream the initial adhesion stage, the peptides would be effective independently of what specific receptor or receptors the virus uses for adhering to the target cell.

Taking into account these findings, the present invention also comprises the use of the beta hairpin peptides described thereof for the manufacture of a drug. In one embodiment, the drug is used to inhibit or attenuate an infection by DENV. In another embodiment, the drug manufactured with the beta hairpin peptides disclosed in the present invention is employed for the treatment of clinical conditions mediated by proteins α2M* or LRP1.

The present invention also provides a method for inhibiting or attenuating an infection by DENV in an affected patient, characterized by the administration to said patient of one or more of the beta hairpin peptides disclosed in the present invention, or a pharmaceutical composition comprising at least one of these peptides.

EXAMPLES

Example 1

Figure 1:
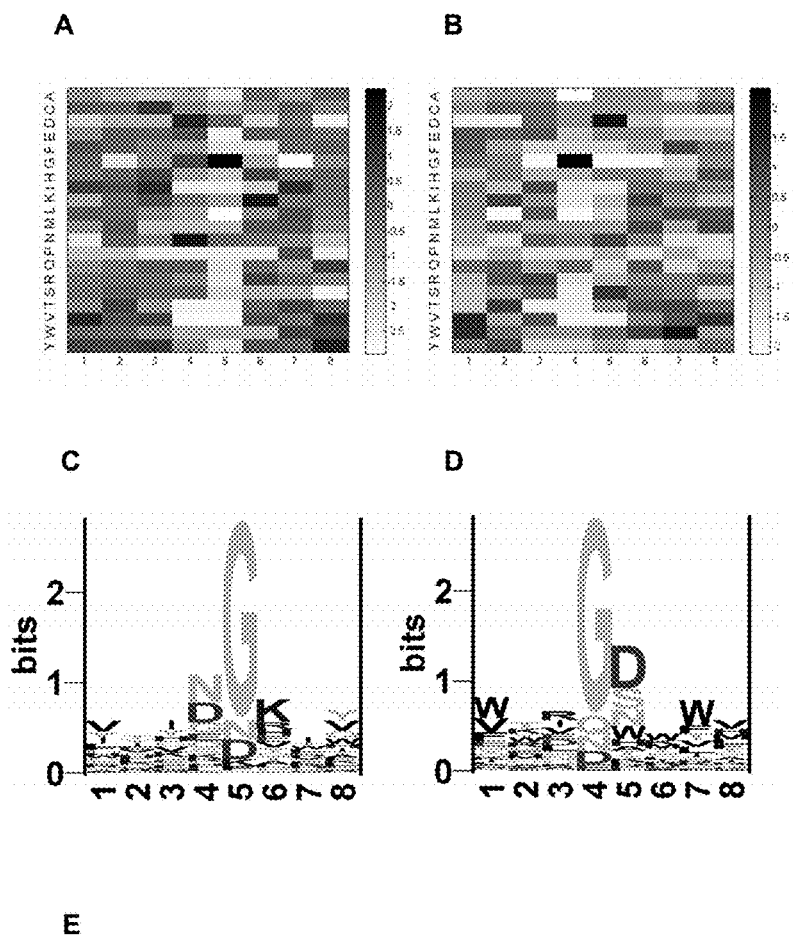
FIG. 1. Design of beta hairpin peptides inhibitory for Dengue virus (DENV) A) Preference parameters for each of the 20 natural amino acids, calculated for each position of an 8-residue hairpin with a type IP central beta turn. The higher the value of the preference parameter, the darker the shade of gray. If there are no instances of a specific amino acid appearing at a particular position in any of the beta hairpins of the WHATIF database, said amino acid is assigned an observed value of 0.5 at that position, and the corresponding preference parameter is then calculated. B) Preference parameters for each of the 20 natural amino acids, calculated for each position of an 8-residue hairpin with a type IIP central beta turn. The coloring scheme and the calculation of preference parameters are identical to those in (A). C-D) Logo-style representation of consensus sequences derived from aligning beta hairpins with either type IP (C) or IIP (D) central beta turns. Letter size is proportional to the ratio of the observed frequency of that amino acid in that position and the expected frequency based on the amino acid composition of the database. E) Sequence alignment of the DIIIE fragment corresponding to hairpin FG in each of the four DENV serotypes and peptide PHB4. MP: modifiable positions (a-e) defined in the present invention, * position corresponding to that of residue Lys385, which is functionally relevant; SS: 'designed' secondary structure for peptide PHB4; RN: residue number in the PHB4 sequence; SSDEN: secondary structure in DIIIE; RNDEN: residue number in the sequence of protein E from DENV2; strands: beta strands corresponding to strands F and G in DIIIE.

Design and Synthesis of Beta Hairpin Peptides Inhibiting the Infection of Dengue Virus Description of the sequences of the beta hairpin peptides disclosed in the present invention A total of nine beta hairpin peptides, denominated PHB1-9 in Table 1, whose sequences are shown in SEQ ID No. 1-9, were designed starting from peptide HDIII3CL (SEQ ID No. 10), following structural/functional criteria aimed at increasing the potency of their antiviral activity and the strength of their binding to cell receptors when compared with HDIII3CL. The structure of these peptides basically consists of four segments: two beta strand segments (structurally analogous to those of the FG beta hairpin of DIIIE), separated by a beta turn and followed by a cationic C-terminal extension composed of three lysine residues. Two different topologies were used: the native topology, used in peptides PHB1-4 and PHB7-9, where the polypeptide backbone runs in the same direction as in the FG beta hairpin of DIIIE, and the reverse topology, used in peptides PHB5 and PHB6. In native topology peptides, the first beta strand segment (Beta1 in Table 1) corresponds structurally to the F beta strand, and the second beta strand segment (Beta2) corresponds to the G beta strand (FIG. 1E). Strand length in peptides PHB1, PHB2 and PHB7 is identical to that of peptide HDIII3CL (six residue strands), but has been extended to seven residues in peptides PHB5-6 and to eight in peptides PHB3-4 and PHB8-9. Longer strands increase the conformational stability of the peptides (Stanger, H. E., et al. (2001). *Proc. Natl. Acad. Sci. USA* 98, 12015-12020).

Residues Cys1, Asn/Tyr3 and Thr5 from peptides PHB1, PHB2 and PHB7 correspond to exposed NHB positions in the FG beta hairpin of DIIIE. An Asn residue, equivalent to residue Asn377 in DENV3 DIIIE, was chosen for position 3 (Asn3) of peptides PHB1 and PHB7, and a Tyr residue, equivalent to Tyr377 of DIIIE from DENV1, DENV2 and DENV4, was chosen for position 3 (Tyr3) of peptide PHB2. Tyr3 is preferred over Asn3, as it is more conserved across DENV serotypes, has a higher propensity for beta sheet formation, and is arranged diagonally to Lys10, facilitating a favorable pi-cation interaction between their corresponding side chains (FIG. 2B). A Thr residue was chosen for position 5 (Thr5) instead of the Val/Ile379 observed in DENV DIIIE sequences (FIG. 1E). The rationale behind this choice was not only that Thr is a conservative substitution relative to Val/Ile with a good beta sheet-forming propensity, but that it is more hydrophilic than the other two alternatives (thus contributing positively to peptide solubility in water) and exhibits higher values of the structural preference parameter (position 2 of the 8-residue beta hairpin in FIG. 1E). Residues Cys14, Asn12 and Lys10 in these peptides occupy positions adjacent to Cys1, Tyr/Asn3 and Thr 5 respectively in the same face of the beta hairpin, but there are no backbone hydrogen bonds between these residues. Residues Lys10 and Asn12 correspond, structurally and functionally, to residues Lys388 (conserved in DENV1-3) and Asn390 (conserved in DENV2-3). A Trp residue was chosen for position 13, since the equivalent residue in DIIIE (Trp391) is strictly conserved across all DENV serotypes. Cysteines Cys1 and Cys14 form a disulfide bond that fulfills an essential structural role. They occupy NHB positions, and a disulfide bond at this position contributes favorably to the stability of beta hairpins (Santiveri C. M., et al. (2008). *Chem. Eur. J.*, 14, 488-499). Later in the invention, it will be demonstrated experimentally that residues Lys10, Trp13, Cys1 and Cys14 are essential for the antiviral activity of these peptides. Peptides similar to HDIII3CL, where substitutions occur at one position (Lys14→ala or Trp17→Ala, Lys14 in HDIII3CL corresponds structurally to residue Lys10 of PHB1, PHB2 and PHB7; and Trp17 of HDIII3CL corresponds structurally to residue Trp13 of PHB1, PHB2 and PHB7) or at two positions (Cys1→Ser and Cys18→Ser, Cys18 of HDIII3CL corresponds structurally to residue Cys14 of PHB1, PHB2 and PHB7), did not exhibit a detectable antiviral effect at the assayed concentration range. Also later in this document, it will be demonstrated experimentally that Tyr3 is a better choice than Asn3, as peptide PHB9 exhibits a higher antiviral potency than peptide PHB8, whose only difference is the nature of the substitution at the position corresponding to Tyr375 of DIIIE from DENV1-2 and DENV4.

TABLE 1

Design of beta hairpin peptides

| Seq No. | Name | [Beta1] | [Turn] | [Beta2] | Extension | Topology | Beta turn type |
|---|---|---|---|---|---|---|---|
| 1 | PHB1 | CVNWTE | pD | KKVNWC | KKK | native | IIP |
| 2 | PHB2 | CVYWTR | pK | WKVNWC | KKK | native | IIP |
| 3 | PHB3 | CIEVNWTE | pD | KKVNWFIC | KKK | native | IIP |
| 4 | PHB4 | CIEVYWTR | pK | WKVNWFIC | KKK | native | IIP |
| 5 | PHB5 | FWNWKWE | kN | KWTWNVE | GGKKK | reverse | IIP |
| 6 | PHB6 | FWNWKWE | pN | KWTWNVE | GGKKK | reverse | IIP |
| 7 | PHB7 | CVNVTI | NG | KKYNWC | KKK | native | IP |
| 8 | PHB8 | CIEVNVTI | NG | KKYNWFIC | KKK | native | IP |
| 9 | PHB9 | CIEVYVTI | NG | KKYNWFIC | KKK | native | IP |
| 10 | HDIII3CL | CSNIVI | GIGDKA | LKINWC | KK | native | 6 aa |
| 11 | HDIII3CL2 | CSNIVI | GIGDKA | LKINWC | KKK | native | 6 aa |
| 12 | HDIII3CLW- | CSNIVI | GIGDKA | LKINAC | KKK | native | 6 aa |
| 13 | HDIII3CLK- | CSNIVI | GIGDKA | LAINWC | KKK | native | 6 aa |
| 14 | HDIII3CLC- | SSNIVI | GIGDKA | LKINWS | KKK | native | 6 aa | p, proline D-stereoisomer;
k, lysine D-stereoisomer;
native topology: identical to the topology of the FG beta hairpin of DIIIE;
reverse topology, opposite to the topology of the FG beta hairpin of DIIIE.

Residues Val2, Trp/Val4, Glu/Arg/Ile6, Lys/Trp9, Val/Tyr11 and Trp13 form part of the opposite face of the hairpin, occupying HB positions. Positions 2, 4 and 6 are adjacent to positions 13, 11 and 9 respectively, and form backbone hydrogen bonds. Position 13 is occupied only by Trp, as explained earlier, and the remaining positions are chosen according to the value of the preference parameter for each residue (FIGS. 1A and B). The Glu6-Lys9 (PHB1) and Arg6-Trp9 (PHB2) pairs were selected for positions 6 and 9, due to the fact that they can establish favorable salt bridge and pi-cation interactions, respectively. Lys9 (PHB1 and PHB7) may functionally mimic the role of residue Lys385 of DIIIE, which is essential for the interaction with α2M*, as demonstrated later in the invention.

Peptides PHB1 and PHB2 have been designed to that a type IIP beta turn forms between residues 6 and 9. Position 7 in these peptides is occupied by a d-Pro residue (a D-stereoisomer of proline), which is a favorable amino acid for the second position of type IIP beta turns (Pantoja-Uceda D, et al. (2006) *Methods Mol Biol.*; 340:27-51). Asp was chosen for position 8 in peptide PHB1 due to the high scores of the preference parameter for this amino acid at this position. In contrast, a Lys residue was selected instead for position 8 in peptide PHB2, with the intention of mimicking Lys386 from DIIIE. For peptide PHB7, a type IP beta turn was introduced between positions 6 and 9. The choice of residue for positions 7 and 8 (Asn7 and Gly8) was driven by the value of the preference parameter (FIGS. 1A and B). Asn-Gly dipeptides are very frequent in type IP beta turns.

The sequence of the beta hairpin of peptides PHB3 and PHB4 comprises the sequence of the corresponding hairpin in peptides PHB1 and PHB2 respectively (Table 1). In this case, positions 4-15 in the former are equivalent to positions 2-13 in the latter, and so the residues chosen for positions 4-15 of PHB3 and PHB4 used the same criteria described above for peptides PHB1 and PHB2.

Figure 2:
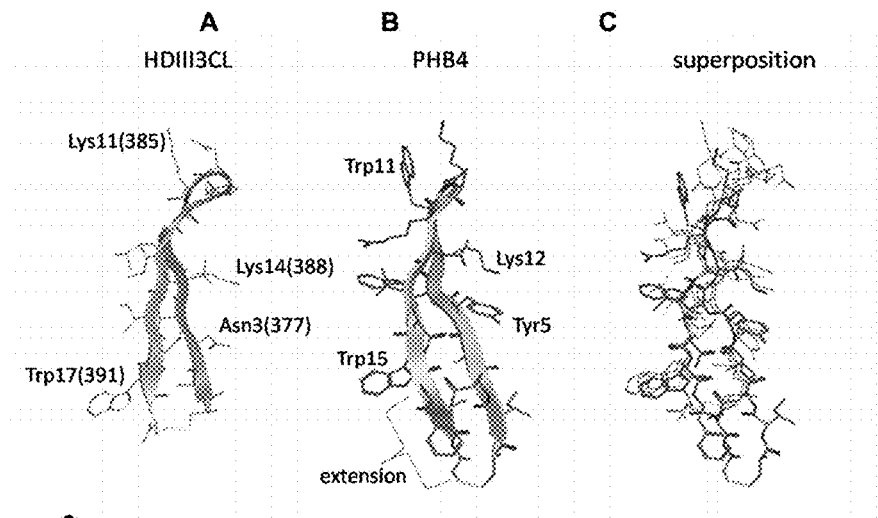
FIG. 2. Tridimensional structural models for DENV-inhibiting beta hairpin peptides. A) HDIII3CL beta hairpin peptide. The segment shown corresponds to the hairpin without the cationic C-terminal extension, highlighting some relevant residues. The ordinates of their equivalent residues in DIIIE are given between parentheses. B) Peptide PHB4. The bracket delimits the portion of the beta strand that has been extended relative to HDIII3CL. C) Structural superposition of both peptides.

Similarly, peptides PHB8 and PHB9 comprise the sequence of peptide PHB7, and the residues for positions 4-15 were chosen following the same criteria as for positions 2-13 in PHB7. Residues Glu3 and Phe16 in PHB3, PHB4, PHB8 and PHB9 were chosen with the purpose of mimicking Glu375 (conserved in DENV1 and DENV3, Asp in DENV2 and DENV4) and Phe392 (conserved in DENV1, DENV2 y DENV4, Tyr in DENV3) from DIIIE (FIG. 1E). Residues Ile2 and Ile17 in PHB3-4 and PHB8-9 were chosen due to their propensity to form beta strand structures. Cys1 and Cys18 occupy NHB positions, and are introduced in order to form a disulfide bond that staples the peptide, thus stabilizing the beta hairpin structure (FIG. 1E and FIG. 2).

The topology of peptides PHB5 and PHB6 is reversed to that of the native FG hairpin loop in DIIIE. In their case, residues Phe1, Asn3, Lys5, Thr12, Asn14 and Glu16 are structurally equivalent to Phe16, Asn14, Lys12, Thr7, Asn5 and Glu3 in peptide PHB3, but they occupy HB positions interacting together through hydrogen bonds. Residues Trp4 and Trp6, which are adjacent to residues Trp11 and Trp13 in the folded hairpin, occupy NHB positions, and were chosen so as to form Trp zippers that increase the conformational stability of the beta hairpin. Residue Trp2 corresponds structurally to residue Trp391 of DIIIE, and was chosen due to the reasons explained earlier. Residues Glu7 and Lys10 were chosen based on high scores for the preference parameter and on the fact that they can form a salt bridge that would provide further stability to the hairpin. The choice of Asn9 was also based on a high score for the preference parameter. Residue d-Pro8 in PHB6 was selected because this is a favorable amino acid for position 2 in type IIP beta turns. The d-Lys residue introduced in PHB5 (at position 8) is aimed at mimicking the Lys385 residue of DIIIE; in addition, d-Lys is more favorable for position 2 of type IIP beta turns than its L stereoisomer. Alternatively, Lys10 in PHB5 and PHB6 may also mimic Lys385 from DIIIE.

The C-terminal extensions introduced in peptides PHB1-9 consist of a Lys tripeptide. Their purpose is to increase the solubility of the disclosed beta hairpin peptides and to confer them a cationic character, thus favoring their interaction through electrostatic forces with receptor LRP1, which is an anionic protein. In the case of peptides PHB5 and PHB6, the cationic tripeptide is joined to the beta hairpin through a di-glycine dipeptide spacer, intended to provide some flexibility between both segments and to block the prolongation of the extended beta structure of strand Beta2.

FIGS. 1C and 1D are logo-type representations (J. Gorodkin, et al. (1997). *Comput. Appl. Biosci.*, Vol. 13, no. 6: 583-586; T. D. Schneider & R. M. Stephens. (1990). *Nucleic Acids Research*, Vol. 18, No 20, p. 6097-6100) of the consensus sequence generated by aligning 8 residue-long type IP and IIP beta hairpins, respectively. They were obtained using the "Protein Sequence Logos using Relative Entropy" web server at http://www.cbs.dtu.dk/-gorodkin/appl/plogo.html. This representation is an alternative to the preference parameter matrices shown in FIGS. 1A y 1B. The size of the letter representing each amino acid is proportional to the "importance" of that amino acid at each position; that is, larger letters imply that the residue is structurally more favorable.

In addition to peptides PHB1-9, Table 1 shows the sequence of peptide HDIII3CL (SEQ ID No.10) and several variants thereof, bearing substitutions of selected residues to an alanine residue, which were used to investigate the importance of the substituted residues for the antiviral activity of this peptide. The peptides thus designed were HDIII3CL2, where peptide HDIII3CL was extended C-terminally with 3 lysine residues (SEQ ID No. 11); HDIII3CLW-, a Trp17→Ala mutant of HDIII3CL2 (SEQ ID No. 12); HDIII3CLK-, a Lys14→Ala mutant of HDIII3CL2 (SEQ ID No. 13); and HDIII3CLC-, a double Cys1→Ala and Cys18→Ala mutant of peptide HDIII3CL2 (SEQ ID No. 14).

FIG. 2 depicts tridimensional models of the structure of the beta hairpin peptides HDIII3CL (A) and PHB4 (B). In the case of peptide HDIII3CL (FIG. 2A), the figure shows the segment corresponding to the hairpin (without the cationic C-terminal extension) and highlights some important residues. The numbers between parentheses correspond to the ordinates of the corresponding residues in DIIIE. In the case of peptide PHB4 (FIG. 2B), a bracket is used to indicate where the strand is extended relative to HDIII3CL, and the following side chains, which are important for the biological activity of the peptides disclosed in the present invention, are highlighted: 1) Lys located at the turn/loop, corresponding to Lys385 of DIIIE, 2) Lys located at the second beta strand, corresponding to Lys388 of DIIIE, 3) Trp located at the second beta strand, corresponding to Trp391 of DIIIE, 4) Tyr located at the first beta strand, corresponding to Tyr377 of DIIIE. FIG. 2C depicts a structural superposition of both peptides.

The peptides PHB1-9, disclosed by the present invention, represent specific examples of beta hairpin peptides with highly potent antiviral activity against DENV that can be designed by following the general principles exposed in the Description section and in this Example of the present invention. The present application, therefore, covers any beta hairpin peptide whose sequence is analogous to at least one of the peptides of the PHB1-9 set, such that its sequence identity is equal to or higher than 70%, and preferably 80%. Such analogous peptides would bear differences in one or several positions selected among: 1) modifiable positions a-e), described in the Description of the Invention section; in this case, the residue(s) in PHB1-9 would be replaced by residues also exhibiting a high structural propensity for occupying that position in beta hairpins; 2) potentially functional positions, described in the Description of the Invention section; in this case, the residue(s) in PHB1-9 would be replaced by a residue from the equivalent position of the FG beta hairpin of DIIIE from a specific DENV serotype; 3) positions corresponding to the C-terminal Lys extension; in this case, the extension comprises two or three lysine residues, preferably three, and 4) positions corresponding to the cysteines forming the disulfide bonds of peptides PHB1-4 and PHB7-9; in these cases one member of the Cys pair may be replaced by Asp/Glu or Lys and the other by Lys or Asp/Glu, such that the peptide may be stapled by forming an amide bond between the side chains of these residues, that is, Asp/Glu on one side and Lys on the other.

The sequences of beta hairpin peptides analogous to peptides of the PHB1-9 set may be described, in general terms, as follows:

i. Peptides analogous to PHB1 and PHB2: these are peptides exhibiting a sequence identity of 70% or higher (preferably 80% or higher) with PHB1 or PHB2, wherein their sequence consists of,
  Position 1 (structural, cyclization): Cys or Lys or Asp or Glu, if Cys then it forms a disulfide bond with Cys residue at position 14, if Glu/Asp (Lys) then its side chain forms an amide bond with the Lys (Glu/Asp) side chain at position 14
  Position 2 (modifiable "a"): Val or Ile or Trp or Phe or Tyr or Met
  Position 3 (potentially functional): Tyr or Asn
  Position 4 (modifiable "a"): Trp or Val or Phe or Glu
  Position 5 (modifiable "d"): Thr or Val or Ile (The latter two are the residues that appear in natural DENV sequences)
  Position 6 (modifiable "a"): Arg or Ile or Val or Glu or Leu
  Position 7 (modifiable "b"): d-Pro
  Position 8 (modifiable "b"): Asp or Lys or Asn
  Position 9 (modifiable "a" and "e"): Trp or Lys or Met or Thr or Gln
  Position 10 (potentially functional): Lys
  Position 11 (modifiable "a"): Val or Met or His or Leu
  Position 12 (potentially functional): Asn or Asp or Ser or His
  Position 13 (essential position): Trp
  Position 14 (structural, cyclization): Cys or Lys or Asp or Glu, if it is Cys then it forms a disulfide bond with the Cys residue at position 1, if it is Glu/Asp (Lys) then its side chain forms an amide bond with the Lys (Glu/Asp) side chain at position 1
  Position 15-17 or 15-16 (C-terminal extension): Lys-Lys-Lys tripeptide or Lys-Lys dipeptide.
ii. Peptides analogous to PHB3 and PHB4: These are peptides with a sequence identity of 70% or higher (preferably 80% or higher) relative to peptides PHB3 and PHB4, wherein said analogous peptides have a sequence consisting of:
  Position 1 (structural, cyclization): Cys or Lys or Asp or Glu, if Cys then it forms a disulfide bond with residue Cys at position 18, if Glu/Asp (Lys) then its side chain forms an amide bond with the Lys (Glu/Asp) side chain at position 18
  Position 2 (modifiable "a"): Ile or Val or Trp or Phe or Tyr or Met
  Position 3 (potentially functional): Glu or Asp
  Position 4 (modifiable "a"): Val or Ile or Trp or Phe or Tyr or Met
  Position 5 (potentially functional): Tyr or Asn
  Position 6 (modifiable "a"): Trp or Val or Phe or Glu
  Position 7 (modifiable "d"): Thr or Val or Ile (The latter two are the residues appearing in natural DENV sequences)
  Position 8 (modifiable "a"): Arg or Ile or Val or Glu or Leu
  Position 9 (modifiable "b"): d-Pro
  Position 10 (modifiable "b"): Asp or Lys or Asn
  Position 11 (modifiable "a" and "e"): Trp or Lys or Met or Thr or Gln
  Position 12 (potentially functional): Lys
  Position 13 (modifiable "a"): Val or Met or His or Leu
  Position 14 (potentially functional): Asn or Asp or Ser or His
  Position 15 (essential position): Trp
  Position 16 (potentially functional): Phe or Tyr
  Position 17 (modifiable "a"): Ile or Val or Trp or Phe or Tyr or Met
  Position 18 (structural, cyclization): Cys or Lys or Asp or Glu, if Cys then it forms a disulfide bond with the Cys residue at position 1, if Glu/Asp (Lys) then its side chain forms an amide bond with the Lys (Glu/Asp) side chain at position 1
  Position 19-21 or 19-20 (C-terminal extension): Lys-Lys-Lys tripeptide or Lys-Lys dipeptide
iii. Peptides analogous to PHB7: These are peptides with a sequence identity of 70% or higher (preferably 80% or higher) with peptide PHB7, wherein said analogous peptides have a sequence consisting of,
  Position 1 (structural, cyclization): Cys or Lys or Asp or Glu, if Cys then it forms a disulfide bond with residue Cys at position 14, if Glu/Asp (Lys) then its side chain forms an amide bond with the Lys (Glu/Asp) side chain at position 14
  Position 2 (modifiable "a"): Val or Ile or Trp or Phe or Tyr or Met
  Position 3 (potentially functional): Tyr or Asn
  Position 4 (modifiable "a"): Val or Ile or Phe or Tyr or Leu
  Position 5 (modifiable "d"): Thr or Val or Ile (The latter two are the residues appearing in natural DENV sequences)
  Position 6 (modifiable "a"): Ile or Val or Tyr, His or Lys
  Position 7 (modifiable "b"): Asn or Asp
  Position 8 (modifiable "b"): Gly
  Position 9 (modifiable "a" and "e"): Lys or His or Arg or Val or Tyr or Glu or Met
  Position 10 (potentially functional): Lys
  Position 11 (modifiable "a"): Tyr or Val or Gln or Trp, Phe
  Position 12 (potentially functional): Asn or Asp or Ser or His
  Position 13 (Essential position): Trp
  Position 14 (structural, cyclization): Cys or Lys or Asp or Glu, if Cys then it forms a disulfide bond with the Cys residue at position 1, if Glu/Asp (Lys) then its side chain forms an amide bond with the Lys (Glu/Asp) side chain at position 1
  Position 15-17 or 15-16 (C-terminal extension): Lys-Lys-Lys tripeptide or Lys-Lys dipeptide
iv. Peptides analogous to PHB8 and PHB9: These are peptides with a sequence identity of 70% or higher (preferably 80% or higher) relative to peptides PHB8 and PHB9, wherein said analogous peptides have a sequence consisting of:
  Position 1 (structural, cyclization): Cys or Lys or Asp or Glu, if Cys then it forms a disulfide bond with residue Cys at position 18, if Glu/Asp (Lys) then its side chain forms an amide bond with the Lys (Glu/Asp) side chain at position 18
  Position 2 (modifiable "a"): Ile or Val or Trp or Phe or Tyr or Met
  Position 3 (potentially functional): Glu or Asp
  Position 4 (modifiable "a"): Val or Ile or Trp or Phe or Tyr or Met
  Position 5 (potentially functional): Tyr or Asn
  Position 6 (modifiable "a"): Val or Ile or Phe or Tyr or Leu
  Position 7 (modifiable "d"): Thr or Val or Ile (The latter two are the residues appearing in natural DENV sequences)
  Position 8 (modifiable "a"): Ile or Val or Tyr or His or Lys Position 9 (modifiable "b"): Asn or Asp
Position 10 (modifiable "b"): Gly
Position 11 (modifiable "a" and "e"): Lys or His or Arg or Val or Tyr or Glu or Met
Position 12 (potentially functional): Lys
Position 13 (modifiable "a"): Tyr or Val or Gln or Trp, Phe
Position 14 (potentially functional): Asn or Asp or Ser or His
Position 15 (essential position): Trp
Position 16 (potentially functional): Phe or Tyr
Position 17 (modifiable "a"): Ile or Val or Trp or Phe or Tyr or Met
Position 18 (structural, cyclization): Cys or Lys or Asp or Glu, if Cys then it forms a disulfide bond with the Cys residue at position 1, if Glu/Asp (Lys) then its side chain forms an amide bond with the Lys (Glu/Asp) side chain at position 1
Position 19-21 or 19-20 (C-terminal extension): Lys-Lys-Lys tripeptide or Lys-Lys dipeptide
v. Peptides analogous to PHB5 and PHB6: These are peptides with a sequence identity of 70% or higher (preferably 80% or higher) relative to peptides PHB5 and PHB6, wherein said analogous peptides have a sequence consisting of:
Position 1 (potentially functional): Phe or Tyr
Position 2 (essential position): Trp
Position 3 (potentially functional): Asn or Asp or Ser or His
Position 4 (modifiable "a"): Trp
Position 5 (potentially functional): Lys
Position 6 (modifiable "a"): Trp
Position 7 (potentially functional, modifiable "b"): Glu or Val or Arg or Ile or Asp
Position 8 (modifiable "b"): d-Pro or d-Lys
Position 9 (modifiable "b"): Asn or Asp or Lys
Position 10 (potentially functional, modifiable "b"): Lys or Met or Trp or Gln or Thr
Position 11 (modifiable "a"): Trp
Position 12 (modifiable "d"): Thr or Val or Ile (The latter two are the residues appearing in natural DENV sequences)
Position 13 (modifiable "a"): Trp
Position 14 (potentially functional): Tyr or Asn
Position 15 (modifiable "a"): Ile or Val or Trp or Phe or Tyr or Met
Position 16 (potentially functional): Glu or Asp
Position 17-20 or 17-21 (C-terminal extension): Gly-Gly-Lys-Lys-Lys pentapeptide or Gly-Gly-Lys-Lys tetrapeptide Peptide Synthesis The peptides listed in Table 1 were obtained by solid phase synthesis on Fmoc-AM-MBHA resin, following the Fmoc/tBu strategy (Barany, G. & Merrifield, R. B. (1977) *J Am Chem Soc.* 99 7363-7365). The process was performed manually, on 10 mL syringes fitted with a porous fritter, so that all reagents and solvents could be conveniently removed by filtration under vacuum. The amino acids were coupled using the DIC/HOBt activation method, and completion of the coupling reaction was verified with the ninhydrin test (Kaiser, E., et al. (1970) *Anal Biochem.* 34 595-598). The synthesized peptides were released by treating the resin with a trifluoroacetic acid/EDT/H$_2$O/TIS (94%/2.5%/2.5%/1%) solution, precipitated with ether and lyophilized for 72 h, after which they were stapled by forming a disulfide bond via oxidation with dimethyl sulf oxide (DMSO) (Andreu, D., et al. (Eds), *Peptide Synthesis Protocols, Methods in Molecular Biology*, Totowa, N.J., 1994, pp. 91-169). The resulting peptides were purified by preparative RP-HPLC in an RP-C18 column, the collected fractions were analyzed independently by analytical RP-HPLC, and the final peptide preparation was obtained by pooling the fractions of purity higher than 99%. Mass spectrometry (ESI-MS) was used to verify the molecular weight of the final preparation.

Mass spectra were acquired with a hybrid octagonal geometry QTOF-2TM mass spectrometer (Micromass, UK) fitted with a Z-spray electrospray ionization source. The software package MassLynx, ver. 3.5 (Waters, USA) was used for spectra acquisition and processing.

Example 2

Inhibition of DENV Infection in Vero Cells

In order to demonstrate that the beta hairpin peptides disclosed by the present infection can inhibit DENV infection in vitro, said peptides were evaluated in a plaque reduction assay using the Vero cell.

The cells were grown in 24 well plates until the monolayer reached approximately 90% confluence, after which they were washed twice with MEM medium without Fetal Bovine Serum (FBS). Then, peptide dilutions were added and the cell-peptide mixtures were incubated typically for 1 hour at 37° C., followed by the addition of a DENV serotype 2 preparation (NIBSC code S16803) at a multiplicity of infection (m.o.i.) of 0.001. The cells were then incubated for 1 hour at 37° C., and once the period of incubation with the viral inoculum concluded, were washed again to remove unbound virions and incubated for 5 days at 37° C. in high density medium (MEM supplemented with non-essential amino acids, 1% FBS, 1% carboxymethylcellulose) in order to let viral plaques form. Afterwards, the cells were stained with 0.1% Naphtol Blue Black in 0.15 M sodium acetate. Two replicates per experimental point were used in each assay, and three independent determinations were performed for each sample.

The toxicity of the beta hairpin peptides was assessed with the MTT (3-(4,5-dimethylthiazol-2-yl)-2,5-diphenyltetrazolium bromide, Invitrogen, USA) assay (Mosmann, T. (1983). *J. Immunol. Methods* 65, 55-63.), and by manual cell counting using a Neubauer chamber. Ninety-six well plates (Costar, USA) were seeded with 200 μL/well of a suspension containing Vero cells at $1 \times 10^5$ cells/mL and incubated until the monolayers reached approximately 90% confluence, typically for 18-24 h. After washing the cells twice with DMEM (Dulbecco's Modified Eagle Medium) medium, 50 μL/well were added of the peptide or additive dilutions to be evaluated (Triton $^{X\text{-}}100$™ dissolved in PBS was used as positive toxicity control) and the plates were incubated at 37° C. under a 5% CO$_2$ atmosphere for 2 or 24 h. Two different procedures were then employed to measure toxicity:

a) A 2 mg/mL solution of MTT in PBS was added (50 μL/well) and the plates were incubated for further 4 h at 37° C., 5% CO$_2$. The medium was then removed, and 100 μL/well of DMSO were then added to solubilize formazan precipitates. Finally, the optical density (OD) of the supernatants at a wavelength of 540 nm was measured using a plate reader (Sensident Scan™, Merck, Germany).

b) The plates were washed with 200 μL/well of DMEM medium and then a trypsin solution (Sigma, USA) was added at 50 μL/well. After inactivating the trypsin by adding 150 μL/well of DMEM supplemented with 10%

FBS, the cells were counted using the Trypan Blue (Gibco, USA) vital stain. The data were processed using the statistical software package Prism v5.3 (GraphPad, USA), using non-linear regression to fit them to a $\log_{10}$ (concentration) vs response curve.

Table 2 shows the calculated IC50 values corresponding to the antiviral activity of the beta hairpin peptides against DENV2 in Vero cells, as well as their toxicity and selectivity index. All the analyzed peptides exhibited detectable antiviral activity in this system. Peptides PHB2, PHB3, PHB4, PHB5, PHB8 and PHB9 exhibited higher antiviral potency than peptide HDIII3CL, although in the case of peptides PHB3, PHB5 and PHB8 the difference was small. In this in vitro system, peptides PHB1, PHB6 and PHB7 were actually less potent than peptide HDIII3CL. Peptide PHB4 exhibited antiviral activity in the nanomolar range and an excellent selectivity index of 4333. This peptide therefore constitutes a lead molecule with excellent properties as a candidate antiviral drug against DENV.

The results also demonstrated that the six-residue interstrand loop of peptide HDIII3CL is completely dispensable, as it has been deleted from the sequence of the beta hairpin peptides disclosed by the present invention and replaced with a beta turn with two central residues, with no similarity, complete or partial, to the original sequence of the DIIIE loop, without deleterious effects on antiviral activity in vitro. This is a desirable characteristic if the peptides are to be used during secondary DENV infections, because this loop is immunodominant during the human antibody response against DENV (Sukupolvi-Petty S, et al. (2007). J Virol.; 81(23):12816-26) and pre-existing antibodies might, therefore, neutralize the antiviral activity of FG beta hairpin-based peptides should the loop not be eliminated. Hence, deleting the loop in the peptides disclosed in the present invention eliminates this possibility.

The data also points at several common features among the most potent beta hairpin peptides, which probably are playing an important role on increasing their antiviral activity. One of them, for instance, is the presence of a lysine (or d-lysine) in a central position on the inter-strand beta turns. Peptide PHB5 is more potent than PHB6, and their only difference is the absence of a lysine residue on the beta turn of the latter (Table 1). Also, PHB2 and PHB4 are more potent than their counterparts PHB1 and PHB3, and neither PHB1 nor PHB3 have a lysine residue at the central positions of the loop (this lysine is thought to mimic functionally the Lys386 residue of DIIIE). Another distinctive feature of the most potent peptides is the presence of a tyrosine residue at the position equivalent to that of residue 377 in DIIIE (ordinates from the E protein of DENV3). For instance, peptide PHB9 is more potent than PHB8, and their only difference is that Tyr5 has been replaced by Asn5 in the latter. Also, PHB2 (containing Tyr3) and PHB4 (containing Tyr5) are more potent than their peptide counterparts PHB1 and PHB3, where these tyrosine residues have been replaced by asparagine residues.

Finally, the data confirmed that extending the beta strands by adding four (two per strand) additional amino acids had a favorable effect on the antiviral activity of the resulting peptides. The potency of peptide PHB4, for instance, was higher than that of PHB2, and that of peptides PHB8 and PHB9 was higher than that of PHB7. Peptide PHB4 is the most potent of the entire series, and the only one whose sequence contains all the three distinctive features of potent peptides identified above. Hence, the experimental data obtained in this example demonstrated, taken together, that the criteria followed for designing the beta hairpin peptides disclosed in the present invention were judiciously chosen.

TABLE 2

Potency, in vitro toxicity and selectivity index for beta hairpin peptides

| Peptide | Antiviral activity in Vero cells | | |
|---|---|---|---|
| | IC50*, µM | Ctox50, µM | SI |
| PHB1 | 75 | >>1000‡ | >>13 |
| PHB2 | 12 | 85 | 7 |
| PHB3 | 17 | >>1000‡ | >>59 |
| PHB4 | 0.003 | 13 | 4333 |
| PHB5 | 17 | 259 | 15 |
| PHB6 | 33 | 411 | 12 |
| PHB7 | 79 | 1911 | 24 |
| PHB8 | 15 | 300 | 20 |
| PHB9 | 7 | 216 | 31 |
| HDIII3CL | 20 | 1000 | 50 |
| HDIII3CL2 | 20 | 1000 | 50 |
| HDIII3CLW- | NA | ND | ND |
| HDIII3CLK- | NA | ND | ND |
| HDIII3CLC- | NA | ND | ND |

*Antiviral activity (50% inhibitory activity),
NA, no detectable activity at concentrations lower than or equal to 100 µM.
‡non toxic at 1000 µM.
ND, not determined Next, it was decided to compare the antiviral activity of peptides PHB4 and HDIII3CL against all four DENV serotypes, with the objective of comparing their respective $IC_{50}$ values. This comparison was performed with plaque reduction assays on Vero cells, adding the viral inoculum for each serotype (DENV1, NIBSC code West Pac 74, DENV2, NIBSC, code S16803; DENV3, NIBSC, code CH53489; DENV 4, NIBSC code TVP360) at a m.o.i. of 0.001. As can be observed in Table 3, peptide PHB4 was active against the four serotypes, and much more so than peptide HDIII3CL (4000- to 7500-fold more potent, depending on serotype). The fact that PHB4 exhibited inhibitory activity against the four serotypes is consistent with the proposed role of the α2M*/LRP1 complex as endocytic receptor for all DENV serotypes and with the experimental evidence demonstrating the binding of peptide PHB4 to these proteins, as shown later in this application.

TABLE 3

Antiviral activity of peptides PHB4 and HDIII3CL against the four serotypes of Dengue virus

| Peptide | Antiviral activity IC50, µM | | | |
|---|---|---|---|---|
| | vs DENV1 | vs DENV2 | vs DENV3 | vs DENV4 |
| PHB4 | 0.002 | 0.003 | 0.005 | 0.01 |
| HDIII3CL | 15 | 20 | 20 | 50 |

Example 3

Inhibition of the Binding of DIIIE to α2M* by Beta Hairpin Peptides

Purification and Activation of Human α2M

Human α2M was purified from 380 mL of human plasma, obtained by pooling plasma samples from healthy 30- to 40-years old volunteers. The plasma was dialyzed against deionized water, with frequent changes, for 72 at 4° C. Insoluble material was removed from the resulting dialysate by centrifugation at 10,000×g for 30 min, and the supernatant was equilibrated to PBS pH 6.0 by dialysis and then loaded onto an XK 50/30 column (Amersham, UK) packed with 65 mL of Chelating Sepharose Fast Flow (Amersham, UK) previously loaded with $Zn^{2+}$ and equilibrated with PBS pH 6.0. After loading the sample, the column was washed with PBS pH 6.0 until the absorbance of the eluent dropped to baseline, and bound proteins were eluted with 10 mM sodium acetate/150 mM sodium chloride pH 5.0 buffer. The collected eluate was concentrated by ultrafiltration and then loaded onto a Superdex 200 (Amersham, UK) gel filtration column equilibrated with PBS pH 7.8. The presence of α2M in the highest molecular weight fraction was verified by Western blotting with an anti-human α2M polyclonal antibody preparation (Sigma, USA).

Purified α2M was activated by incubating it with 200 mM methylamine in 50 mM sodium phosphate, 150 mM sodium chloride, pH 7.4. The resulting α2M_MeNH$_2$ (α2M*) preparation was extensively dialyzed against 50 mM sodium phosphate/0.5 M sodium chloride pH 7.8.

Competition Assays

The ability of peptides PHB1-9 and HDIII3CL to inhibit the interaction of recombinant DIIIE1J with α2M* was analyzed using a competition ELISA format. The plates were coated with purified α2M* and incubated with previously purified and biotinylated DIIIE1J (DIIIE1Jbiot) in the presence of different concentrations of the test peptides and/or recombinant DIIIE1J, detecting α2M*-bound DIIIE1Jbiot with a streptavidin-peroxidase conjugate. Details of the experimental procedure followed to obtain recombinant DIIIE1J (SEQ ID No. 19) are presented later, but essentially, the molecule consists of residues 289-400 (numbering according to sequence PIR:A32401) of protein E of DENV1, strain 1636 (Chu, M. C., et al. (1989). *Journal of General Virology* 70 (Pt 7), 1701-1712.), corresponding to domain III followed by a C-terminal six-histidine tag.

Figure 3:
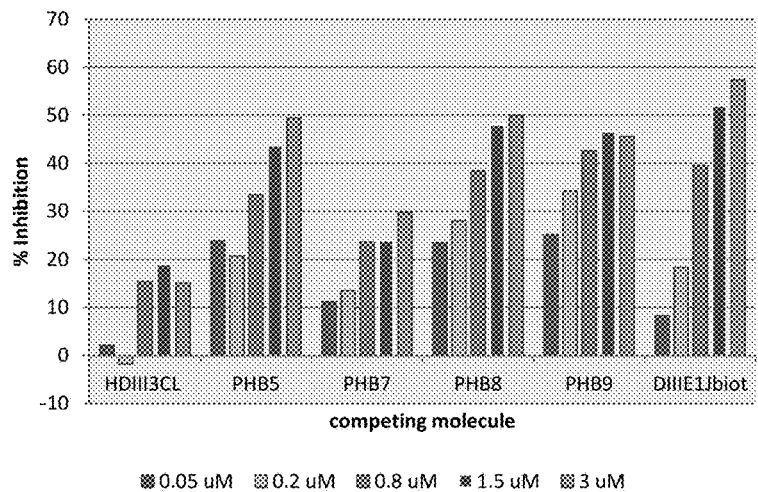
FIG. 3. Inhibition of the binding of biotinylated DIIIE from DENV1 (DIIIE1Jbiot) to protein α2M*. The ordinate axis shows the inhibition percentage for the beta hairpin peptides disclosed by the present invention in the 0.05-3 μM peptide concentration range. The inhibitory activity of peptide HDIII3CL and recombinant DIIIE1J are also shown.

At peptide concentrations in the low micromolar to sub-micromolar/nanomolar range, the beta hairpin peptides PHB5, PHB7, PHB8 and PHB9 partially inhibit the binding of DIIIE1Jbiot to α2M* (FIG. 3), and inhibition percentages increase monotonically with peptide concentration. Peptides PHB5, PHB8 and PHB9 are the most potent inhibitors of this group, exhibiting inhibition percentages that range from 23 to 50%, similar to that of recombinant DIIIE1J. At the analyzed concentration ranges, these three peptides are better inhibitors (2- to 12-fold, depending on their exact concentration) of DIIIE1Jbiot binding to α2M* than peptide HDIII3CL.

The maximum inhibition percentage exhibited by peptide HDIII3CL in these assays was only 18%; lower than the inhibition percentage of even PHB7, the smallest beta hairpin peptide. This indicates that in practice, the residues of the inter-strand loop of the FG hairpin of DIIIE are dispensable for the purpose of interacting with protein α2M*, as the original 6-residue long loop has been replaced in peptide PHB7 by a type IP beta turn with only two central residues. The sequence of this beta turn bears no similarity—total or partial—to that of the original loop, its residues having been chosen based on structural criteria (high type IP beta turn forming propensity, beta hairpin connectors). The only residue from the original HDIII3CL loop that still remains in peptide PHB7 (and PHB8 and PHB9 as well) is Lys11 (HDIII3CL numbering), whose functional role is mimicked by Lys9 of PHB7, which occupies a similar (structurally quasi-equivalent) spatial position.

In addition to Lys9 (which mimics Lys11 from HDIII3CL) there are other PHB7 residues mimicking the role of HDIII3CL residues: a) Asn3, Lys10 and Asn12 from PHB7 mimic residues Asn3, Lys14 and Asn16 from HDIII3CL (these are the beta hairpin residues that do not form hydrogen bonds), whose side chains project into the exposed face of the FG hairpin of DIIIE and are, therefore, potentially functional; b) Trp13 from PHB7 is equivalent to Trp17 from HDIII3CL, and corresponds to a Trp residue that is strictly conserved across all flaviviruses; c) Cys1 and Cys14 from PHB7 form a disulfide bridge equivalent to that formed by Cys1-Cy18 from HDIII3CL. The fact that PHB7 indeed retains, and as a matter of fact improves, upon the DENV inhibitory activity of HDIII3CL suggests that the features that were retained during the design of the former do play an important role for the functional activity of the peptides disclosed by the present invention.

Peptides PHB8 and PHB9 are better inhibitors than peptide PHB7. This indicates that the addition of four residues (two per strand) to PHB8 and PHB9 contributes favorably to the DENV inhibitory activity of the peptides disclosed by the present invention.

Figure 4:
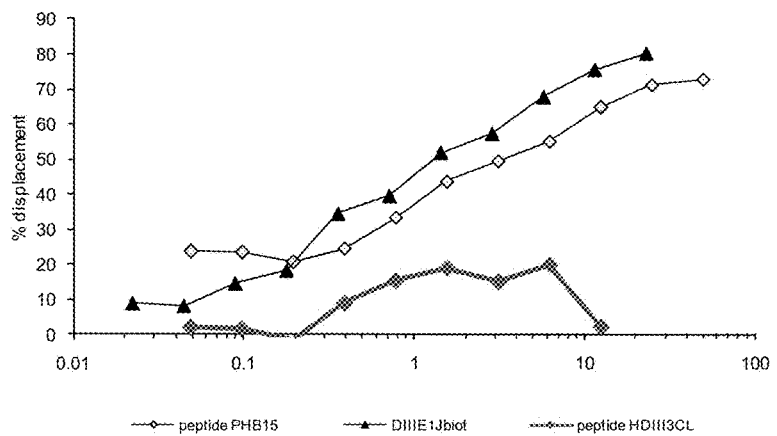
FIG. 4. Dose-response curves for the inhibition of the binding of biotinylated DENV1 DIIIE (DIIIE1Jbiot) to α2M*. The chart shows the inhibition percentages corresponding to the beta turn peptide PHB5, peptide HDIII3CL and recombinant DIIIE1J.

As can be observed in FIG. 4, the apparent affinity of the interaction between the PHB5 beta hairpin peptide and α2M* is similar to that of the interaction between DIIIE and α2M*, as the inhibition percentages for each assayed PHB5 concentration are only slightly lower than those exhibited by DIIIE1J. These results demonstrate that it is possible to use a beta hairpin peptide whose topology is reversed relative to that of the native FG beta hairpin of DIIIE and still be able to inhibit the DIIIE-α2M* interaction. A similar conclusion may be drawn regarding the type of beta turn designed into the peptide, taking into account that a type IIP turn is used in PHB5, whereas peptides PHB7-9 use type IP turns. What is important is to preserve the structural equivalency of the residues that are essential for the interaction, that is, that they be arranged in an analogous spatial fashion even when presented within the context of a structurally different framework. Also, PHB5 demonstrates that the role played by the disulfide bond in stabilizing the conformation of peptides PHB8 and PHB9 can be taken over by other structural motifs, such as the Trp zipper used in PHB5.

Figure 5:
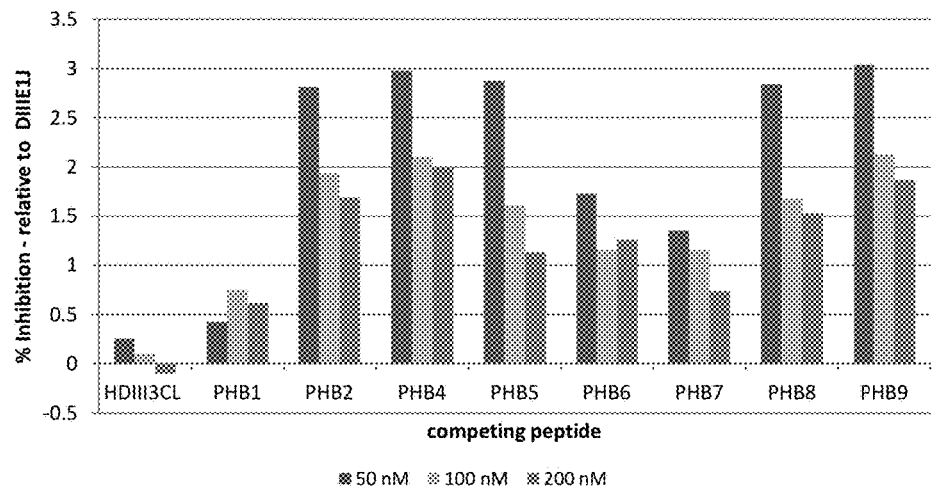
FIG. 5. Inhibition of the binding of biotinylated DENV1 DIIIE (DIIIE1Jbiot) to protein α2M* by the indicated beta hairpin peptides, and relationship with antiviral activity. The ordinate axis shows the binding inhibition percentage relative to the binding inhibition determined for DIIIE1J. The data showed correspond to the submicromolar (50-200 nM) peptide concentration range.

An essential element of the present invention is the analysis of the biological activity of the disclosed peptides at the nanomolar range. High potency peptides allow the use of lower therapeutic dosages and the advantages they entail in terms of lower costs and lower likelihood of appearance of a number of issues associated with high dosages, such as aggregation, non-specific interactions, antigenicity and immunogenicity. As shown in FIG. 5, at the nanomolar/submicromolar range peptides PHB2, PHB4, PHB5, PHB8 and PHB9 were still better inhibitors of the binding of biotinylated DIIIE1J (DIIIE1Jbiot) to α2M* than DIIIE1J itself (1.5- to 3-fold better percentage inhibition). On the other hand, at that concentration range the inhibition exhibited by peptide HDIII3CL is very low, compared to DIIIE1J.

Example 4

Mapping of Essential Residues for the Binding of DIIIE to α2M*

Preparation of a Library of Alanine Mutants for DIIIE (DIIIE1PRS)

In order to determine which residues in DIIIE from DENV1 play an important role in the interaction of said molecule with a number of different ligands, a library of single-residue mutants was prepared where each solvent-exposed residue was systematically replaced by an alanine residue (a technique more commonly known as 'alanine scanning') in order to later study the binding of said mutant variants to the ligands to be analyzed. In this type of experiments, any variation regarding the binding of a particular variant to the ligand is interpreted as evidence of the involvement of the mutated residue in the interaction of the wild-type protein with said ligand.

In order to prepare this library, the initial analysis was circumscribed to residues 289 to 395 (numbering according to GenBank: AAN32775.1) of the envelope protein of DENV1, strain PRS 288690 (Goncalvez, A. P., et al. (2002), Virology 303 (1), 110-119.). The sequence corresponding to this fragment of the viral polyprotein, herein defined as DIIIE from DENV1 strain PRS 288690 (DIIIE1PRS), is shown in SEQ ID No. 15.

Selection of Residues to be Mutated in DIIIE1lPRS

Instead of a brute-force approach where every residue was replaced by alanine one at a time, it was decided to make a previous selection based on relative solvent accessibility, as estimated using the WHAT IF version 2005091 9-1718 software package (Vriend, G., (1990), *J. Mol.Graph.* 8, 52-6), and based on the estimation of the difference in stability of every possible variant with respect to the wild-type protein, expressed as the ΔΔG calculated by FoldX version 6.0 (Schymkowitz, J., et al. (2005). *Nucleic Acids Res.* 33, W382-W388). Both calculations were based on homology models of DIIIE1PRS (residues 1-105 in SEQ ID No. 15), obtained from the crystallographic coordinates of protein E from DENV3 (Modis, Y., et al. (2003). *Proc. Natl. Acad. Sci. U.S.A* 100, 6986-6991) and submitted to an energy minimization process.

The criterion used to select residues to be mutated to Ala was a relative accessibility higher than 15% and a ΔΔG lower than 4 kcal/mol. The 79 positions meeting this criterion and the results of the calculations for the parameters mentioned above are shown in Table 4.

TABLE 4

Residues selected for the alanine scanning of DIIIE1PRS.

| Res. | aa | %ACC | ΔΔG$^1$ kcal/mol | ΔΔG$^2$ kcal/mol |
|---|---|---|---|---|
| 289 | MET | 78.4 | — | — |
| 290 | ASP | 85.6 | 2.4 | 2.4 |
| 291 | LYS | 88.2 | 2.5 | 2.4 |
| 292 | LEU | 70.4 | 2.3 | 2.2 |
| 293 | THR | 82.8 | 2.8 | 2.8 |
| 294 | LEU | 70.6 | 2.3 | 2.1 |
| 295 | LYS | 76.6 | 3.4 | 3.3 |
| 296 | GLY | 26.7 | 3.6 | 2.2 |
| 297 | MET | 58.7 | 2.1 | 2.1 |
| 298 | SER | 91.1 | 2.5 | 2.3 |
| 299 | TYR | 32.5 | 3.7 | 3.2 |
| 300 | VAL | 65.7 | 2.4 | 2 |
| 301 | MET | 57.8 | 2.2 | 2.4 |
| 303 | THR | 76.8 | 2.8 | 2.9 |
| 304 | GLY | 23.2 | 4.6 | 3.7 |
| 305 | SER | 18.5 | 3.2 | 3.1 |
| 307 | LYS | 51.3 | 3.9 | 3.7 |
| 308 | LEU | 31 | 5.3 | 5 |
| 309 | GLU | 32.1 | 2.2 | 2.6 |
| 310 | LYS | 67.9 | 3.2 | 3.1 |
| 311 | GLU | 79.1 | 2.8 | 2.6 |
| 312 | VAL | 19 | 3.8 | 4 |
| 314 | GLU | 42.2 | 1.7 | 1.5 |
| 315 | THR | 37.8 | 5.1 | 4.7 |
| 316 | GLN | 90.6 | 2.8 | 2.7 |
| 317 | HIS | 79.1 | 1.8 | 2.2 |
| 321 | LEU | 43.9 | 4.1 | 4 |
| 323 | GLN | 23.7 | 2.3 | 2.8 |
| 325 | LYS | 30 | 3.3 | 3.1 |
| 327 | GLU | 59.1 | 3.3 | 3.1 |

TABLE 4-continued

Residues selected for the alanine scanning of DIIIE1PRS.

| Res. | aa | %ACC | ΔΔG$^1$ kcal/mol | ΔΔG$^2$ kcal/mol |
|---|---|---|---|---|
| 329 | THR | 84.2 | 2.2 | 2.6 |
| 330 | ASP | 29.5 | 0.5 | 2 |
| 332 | PRO | 40.5 | 3.9 | 3.8 |
| 334 | LYS | 15.1 | 1.8 | 1.7 |
| 336 | PRO | 21.5 | 4.9 | 4.9 |
| 338 | SER | 28 | 2.3 | 2.3 |
| 340 | GLN | 17.6 | 2 | 2.2 |
| 342 | GLU | 61.8 | 1.8 | 1.1 |
| 343 | LYS | 72.2 | 3.4 | 3 |
| 344 | GLY | 31.4 | 4.7 | 4.3 |
| 345 | VAL | 60.8 | 3.2 | 2.2 |
| 346 | THR | 58.2 | 2.7 | 2.7 |
| 347 | GLN | 55.3 | 2.6 | 2.9 |
| 348 | ASN | 51.4 | 3.1 | 3 |
| 350 | ARG | 69 | 4 | 3.7 |
| 351 | LEU | 21.1 | 5.4 | 5.5 |
| 352 | ILE | 36.3 | 3.4 | 3.6 |
| 353 | THR | 42.7 | 3.6 | 2.8 |
| 355 | ASN | 26 | 2.6 | 2.7 |
| 357 | ILE | 24.1 | 3.8 | 3.8 |
| 359 | TRH | 66.6 | 2.5 | 2.6 |
| 360 | ASP | 31.5 | 3.1 | 2.2 |
| 361 | LYS | 38.5 | 1.8 | 2.9 |
| 362 | GLU | 65.3 | 2.2 | 2.2 |
| 363 | LYS | 61.1 | 3.3 | 3.1 |
| 364 | PRO | 34.9 | 4.2 | 4.3 |
| 365 | VAL | 15.4 | 4 | 4 |
| 366 | ASN | 55.8 | 2.7 | 2.8 |
| 368 | GLU | 26.9 | 3.1 | 3.2 |
| 370 | GLU | 29 | 3.2 | 3.1 |
| 372 | PRO | 25.1 | 5.5 | 5.2 |
| 373 | PHE | 62.9 | 2.7 | 2.5 |
| 374 | GLY | 25 | 4.3 | 4 |
| 375 | GLU | 55.4 | 3.6 | 3.6 |
| 379 | VAL | 17.7 | 4 | 4 |
| 383 | GLY | 75.8 | 3.4 | 3.9 |
| 384 | GLU | 68.3 | 3 | 3 |
| 385 | LYS | 67.2 | 3.3 | 3 |
| 387 | LEU | 22.8 | 3.6 | 3.7 |
| 388 | LYS | 60.6 | 3.4 | 3.5 |
| 389 | LEU | 23.1 | 4.7 | 5.6 |
| 390 | SER | 54.4 | 2.5 | 2.4 |
| 391 | TRP | 17.6 | 4.2 | 5 |
| 392 | PHE | 63.8 | 3 | 3 |
| 394 | LYS | 61.8 | 2.7 | 2.7 |

ΔΔG: difference in folding ΔG between the Ala mutant and the wild-type protein (1: non-minimized models, 2: minimized model);
%AAC: solvent accessibility percentage. Boldfaced, italicized residues correspond to positions where ΔΔG was higher than 4 kcal/mol.

Preparation of a Library of Recombinant Plasmids for the Expression of DIIIE1PRS and its Mutated Variants in *Escherichia Coli*

Figure 6:
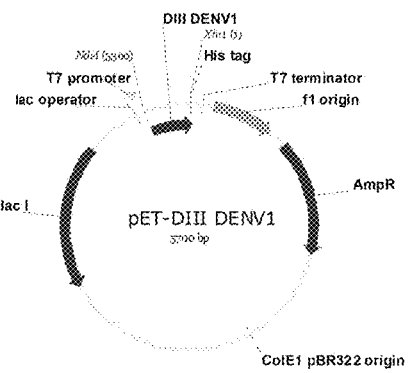
FIG. 6. Diagram of plasmid pET-DIII DENV1.

After selecting the DIIIE1 PRS residues to be used for the alanine scan, recombinant plasmids were prepared for the heterologous expression of each Ala-mutant variant of the library in *E. coli*. This was accomplished by synthesizing, using the method of Agarwal et al. (Agarwal K L, et al. (1970), *Nature* 227, 27-34), and starting from oligonucleotides synthesized on solid phase via phosphoramidite chemistry (Beaucage S L & Caruthers M H (1981). *Tetrahedron Letters*, 22, 1859), a double-stranded DNA molecule coding for residues 289-400 (numbering according to GenBank: AAN32775.1) of protein E of DENV1, strain PRS 288690 (Goncalvez, A. P., et al. (2002). *Virology* 303 (1), 110-119), followed by a C-terminal 6-histidine tag; a recombinant protein defined here as recombinant DIIIE1PRS (rDIIIE1PRS, SEQ ID No. 17). This double-stranded DNA molecule (SEQ ID No. 16) contains recognition sites for the Nde I and Xho I restriction enzymes, designed so that the fragment can be inserted into plasmid pET22b (Novagen Inc., USA) in the same reading frame as the start codon provided by said plasmid. After digesting this double-stranded DNA molecule with the Nde I and Xho I restriction enzymes under the conditions specified by their manufacturer, the digested fragment was ligated, using T4 DNA ligase under the conditions specified by its manufacturer, to plasmid pET22b (Novagen Inc., USA) previously digested in the same manner. The ligation mixture thus obtained was transformed into the XL-1 Blue strain of *E. coli* (Bullock W O, et al. (1987). *Biotechniques*; 5:376-8) as described by Sambrook et al. (Sambrook J, et al. *Molecular cloning: A laboratory manual.* New York, USA: Cold Spring Harbor Laboratory Press; 1989), and the plasmids from colonies grown in selective medium were screened, purified and sequenced to obtain a plasmid whose sequence corresponded to the expected sequence. Said plasmid was denominated pET-DIII DENV1 (SEQ ID No. 18), and is represented diagrammatically in FIG. 6.

The construction of recombinant plasmids to express the 79 previously selected Ala mutants of DIII1PRS was performed as described above for pET-DIII DENV1, but synthesizing in each case a different double-stranded DNA molecule in which the codon corresponding to the residue to be mutated was replaced by a GCG triplet, corresponding to an alanine codon. The codon that was replaced in each variant, together with the amino acid for which it coded, is shown in Table 5.

TABLE 5

Residue replaced by alanine and corresponding codon, replaced by GCG in each variant of the library of DIIIE1PRS mutants.

| Variant | Residue replaced by Ala (SEQ ID No. 15) | Codon | Position in SEQ ID No. 16 | Variant | Residue replaced by Ala (SEQ ID NO: 15) | Codon | Position in SEQ ID No. 16 |
|---|---|---|---|---|---|---|---|
| D290 | D2 | GAT | 7-9 | K343 | K55 | AAA | 166-168 |
| K291 | K3 | AAA | 10-12 | G344 | G56 | GGA | 169-171 |
| L292 | L4 | CTG | 13-15 | V345 | V57 | GTG | 172-174 |
| T293 | T5 | ACT | 16-18 | T346 | T58 | ACC | 175-177 |
| L294 | L6 | TTA | 19-21 | Q347 | Q59 | CAG | 178-180 |
| K295 | K7 | AAA | 22-24 | N348 | N60 | AAT | 181-183 |
| G296 | G8 | GGG | 25-27 | R350 | R62 | AGA | 187-189 |
| M297 | M9 | ATG | 28-30 | L351 | L63 | TTG | 190-192 |
| S298 | S10 | AGC | 31-33 | I352 | I64 | ATA | 193-195 |
| Y299 | Y11 | TAT | 34-36 | T353 | T65 | ACA | 196-198 |
| V300 | V12 | GTG | 37-39 | N355 | N67 | AAT | 202-204 |
| M301 | M13 | ATG | 40-42 | I357 | I69 | ATA | 208-210 |
| T303 | T15 | ACA | 46-48 | T359 | T71 | ACT | 214-216 |
| G304 | G16 | GGC | 49-51 | D360 | D72 | GAC | 217-219 |
| S305 | S17 | TCA | 52-54 | K361 | K73 | AAA | 220-222 |
| K307 | K19 | AAG | 58-60 | E362 | E74 | GAA | 223-225 |
| L308 | L20 | CTA | 61-63 | K363 | K75 | AAA | 226-228 |
| E309 | E21 | GAG | 64-66 | P364 | P76 | CCA | 229-231 |
| K310 | K22 | AAG | 67-69 | V365 | V77 | GTC | 232-234 |
| E311 | E23 | GAA | 70-72 | N366 | N78 | AAC | 235-237 |
| V312 | V24 | GTG | 73-75 | E368 | E80 | GAG | 241-243 |
| E314 | E26 | GAG | 79-81 | E370 | E82 | GAA | 247-249 |
| T315 | T27 | ACC | 82-84 | P372 | P84 | CCT | 253-255 |
| Q316 | Q28 | CAG | 85-87 | F373 | F85 | TTT | 256-258 |
| H317 | H29 | CAT | 88-90 | G374 | G86 | GGT | 259-261 |
| L321 | L33 | CTA | 100-102 | E375 | E87 | GAG | 262-264 |
| Q323 | Q35 | CAG | 106-108 | V379 | V91 | GTG | 274-276 |
| K325 | K37 | AAA | 112-114 | G383 | G95 | GGT | 286-288 |

TABLE 5-continued

Residue replaced by alanine and corresponding codon, replaced by GCG in each variant of the library of DIIIE1PRS mutants.

| Variant | Residue replaced by Ala (SEQ ID No. 15) | Codon | Position in SEQ ID No. 16 | Variant | Residue replaced by Ala (SEQ ID NO: 15) | Codon | Position in SEQ ID No. 16 |
|---|---|---|---|---|---|---|---|
| E327 | E39 | GAA | 118-120 | E384 | E96 | GAA | 289-291 |
| T329 | T41 | ACA | 124-126 | K385 | K97 | AAA | 292-294 |
| D330 | D42 | GAT | 127-129 | L387 | L99 | TTG | 298-300 |
| P332 | P44 | CCA | 133-135 | K388 | K100 | AAA | 301-303 |
| K334 | K46 | AAG | 139-141 | L389 | L101 | CTA | 304-306 |
| P336 | P48 | CCC | 145-147 | S390 | S102 | AGC | 307-309 |
| S338 | S50 | TCG | 151-153 | W391 | W103 | TGG | 310-312 |
| Q340 | Q52 | CAA | 157-159 | F392 | F104 | TTC | 313-315 |
| E342 | E54 | GAG | 163-165 | K394 | K106 | AAA | 319-321 |

Transformation of the Plasmids of the Library of DIIIE1PRS Mutants into E. Coli and Cryopreservation of the Obtained Clones In order to obtain clones of E. coli cells containing the plasmids for expressing in this host the selected DIIIE1 PRS variants, transformation-competent cells of the E. coli strain BL21(DE3) (Studier, F. W. & Moffatt, B. A. (1986) J. Mol. Biol. 189(1), 113-130) were prepared and divided into aliquots, each of which was separately transformed with 20 ng of one of the plasmids of the mutant library, using methods known to those skilled in the art (Sambrook, J., et al. Molecular cloning: A laboratory manual. 1989. New York, USA, Cold Spring Harbor Laboratory Press). The transformed aliquots were plated separately onto LB-agar plates containing ampicillin at 100 μg/mL. After incubation for 12 hours at 37° C. to enable bacterial growth, one well-isolated colony from each plate was inoculated into separate test tubes containing 5 mL of LB broth each, supplemented with ampicillin at 100 μg/mL, and incubated at 37° C. under agitation (200 rpm) until the appearance of visible turbidity. The cultures were then centrifuged aseptically at 3000×g for 20 min. at 25° C., each resuspended into 250 μL of fresh LB broth+250 μL 40% (v/v) glycerol, and in turn split into 100 μL aliquots that were stored at −70° C.

Purification of Mutant DIIIE1PRS Variants

After preparing a library of cryopreserved E. coli clones expressing each of the variants of the DIIIE1PRS mutant library, a small-scale process was used to purify said DIIIE1 PRS variants. Briefly, for each variant, a single cryopreserved aliquot of the E. coli clone containing the corresponding plasmid was used to inoculate 50 mL of ZYM50502 medium (Studier, F. W. (2005). Protein Expr. Purif. 41(1), 207-234) supplemented with ampicillin at 100 μg/mL in a 1 L Erlenmeyer flask, which was then incubated for 12 hours at 37° C., 300 r.p.m. Afterwards, the culture was centrifuged at 3000×g, 25° C. for 20 min, the supernatant was discarded, and the resulting biomass was lysed by resuspension into 19 mL of AG buffer (PBX 1X, NaCl 0.3 mol/L, imidazole 20 mM) containing 6 M guanidinium hydrochloride (GuHCl), eliminating the viscosity of the homogenate by brief sonication for 30 with an appropriate probe. After clarifying the homogenate by centrifugation at 3000×g, 25° C. for 45 min, the supernatant was incubated for 1 h at 25° C. in a slow rotary shaker with 0.3 mL of $Ni^{2+}$-nitrilotriacetic acid-agarose resin (Ni-NTA agarose, Qiagen, Germany) and the resulting slurry was gravity-packed into an empty NAP-10 column (GE Healthcare, USA) and washed consecutively with AG buffer containing decreasing concentrations of GuHCl (6 M to 1.2) and, finally, with buffer A (PBS 1X, NaCl 0.3 M, imidazole 20 mM). Then, the protein was eluted with 0.9 mL of buffer E (PBS 1X, NaCl 0.3 M, imidazole 300 mM), and the eluate was subjected immediately to buffer exchange into PBS 1X by gel filtration on Sephadex G25 using pre-packed PD-10 columns (Amersham, UK). Total protein concentration of the resulting preparation was determined by the bicinchoninic acid (BCA) method (Smith, P. K. (1985). Anal. Biochem. 150(1), 76-85), and purity was assessed by SDS-PAGE under reducing conditions (Laemmli, U. K. (1970). Nature 227(259), 680-685), to ensure that no degradation products were present. The library of purified DIIIE1 PRS variants was stored at −20° C. until used.

Competition Assays

Figure 7:
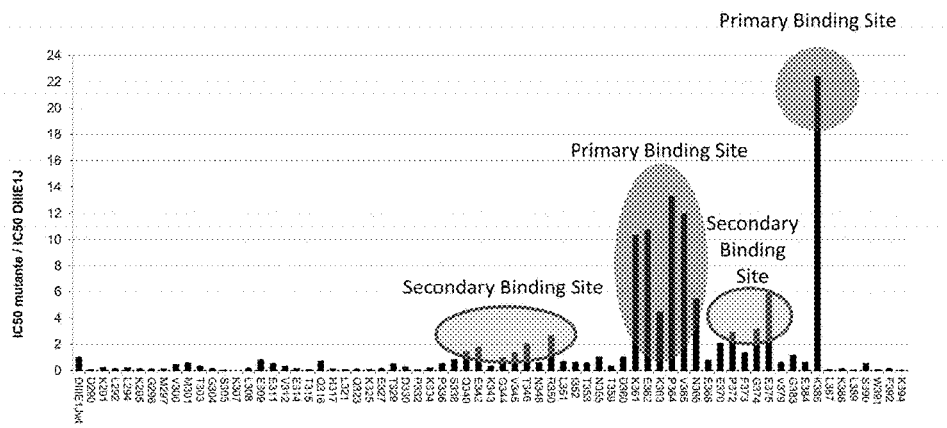
FIG. 7. Mapping of DIIIE residues essential for its interaction with protein α2M. The ordinate axis shows the ratio between the IC50 values for each alanine replacement mutation (corresponding to each residue in the abscissa) and the IC50 value for recombinant DIIIE (DIIIE1PRS). The ellipsoids shaded in dark tones mark the residues of the primary interaction site. The ellipsoids shaded in light tones define the secondary interaction site.
Figure 8:
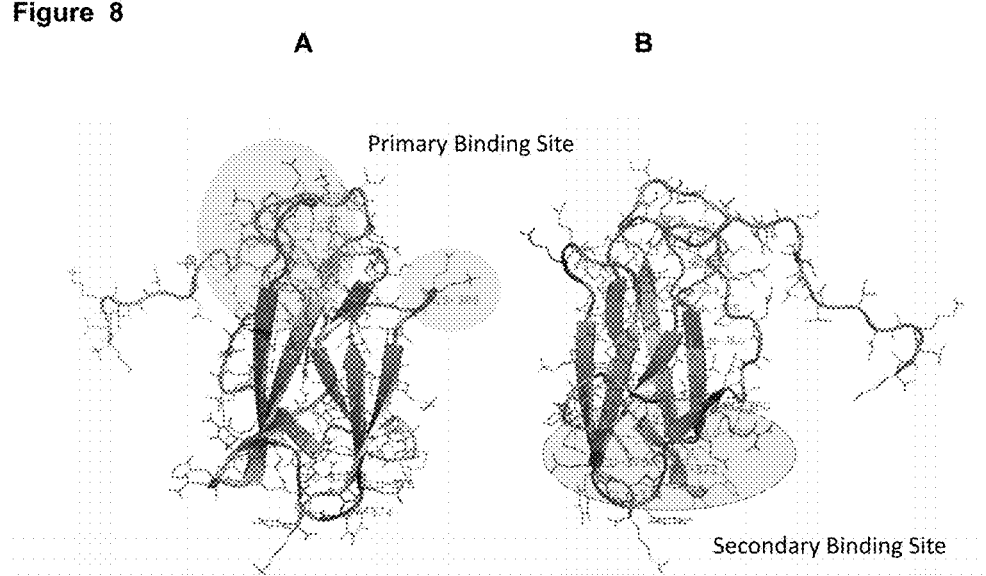
FIG. 8. Location within the tridimensional structure of DIIIE of the sites engaged during its interaction with protein α2M*. Two views of the structure of DENV1 DIII are shown, including a detailed stick representation and a representation of secondary structure where arrows and cylinders stand for beta sheets and loops, respectively. The relevant residues are labeled. They cluster into two sites, represented by shaded ellipsoids: a primary site (A) and a secondary site (B). The tridimensional structure was rendered using PyMOL (*The PyMOL Molecular Graphics System*, Version 1.2r3pre, Schrödinger, L L C.)
Figure 9:
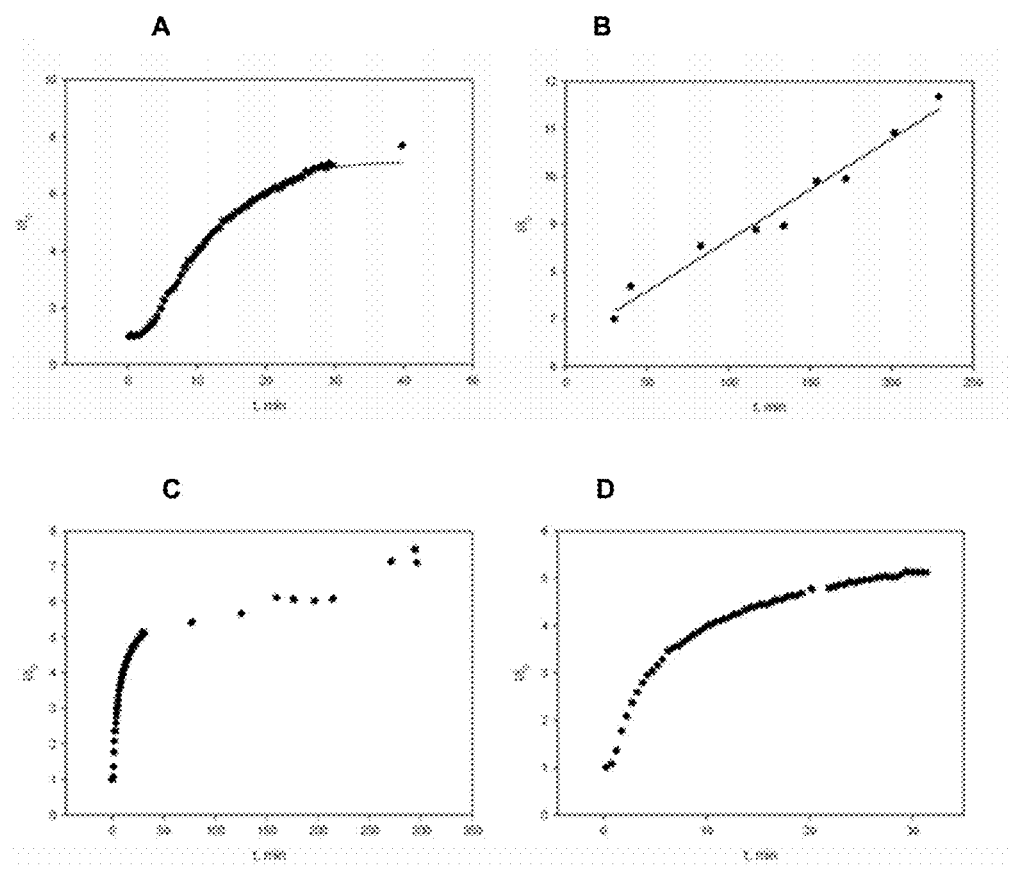
FIG. 9. Aggregation kinetics for peptide PHB4 in phosphate-buffered saline (PBS). A-B): Aggregation kinetics for peptide PHB4 at 10 μM, in PBS. The ordinate axis corresponds to the intensity of dispersed light, relative to intensity of the dispersed light at time 0 (the moment in which the peptide is dissolved into PBS). A: Aggregation profile for time 0 to 300 min. B: First 30 min of the aggregation process. C-D): Aggregation kinetics of peptide PHB4 at 5 μM, in PBS. C: Early aggregation, time 0-40 min. D: Late aggregation, time 30-230 min.
Figure 10:
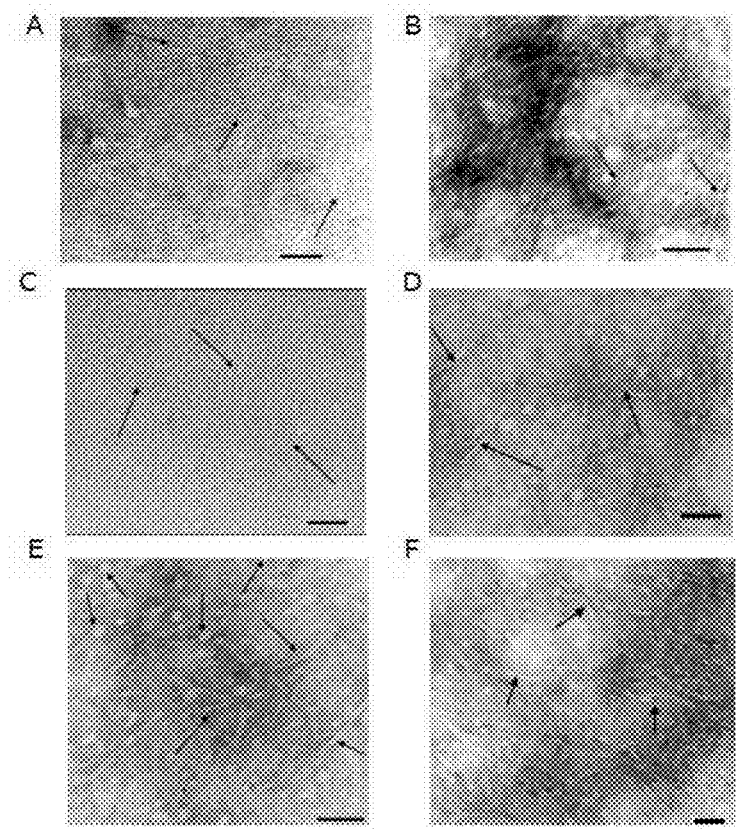
FIG. 10. Study of the morphology of aggregates of peptide PHB4 by Transmission Electron Microscopy (TEM) at a peptide concentration of 2 mg/mL, in water and PBS. The experimental conditions were: Peptide studied immediately after dissolution into water (A) or PBS (B); peptide studied after dissolution and heating for 1 hour at 50° C. in either water (C) or PBS (D); and peptide studied after dissolution in water (E) or PBS (F), followed by heating for 1 hour at 50° C. and then incubation at room temperature for 2 hours. The bars in A, B, E and F have a length of 100 nm, and the bars in C-D have a length of 200 nm.

The ability of each DIIIE1 PRS alanine mutant to inhibit the interaction of recombinant DIIIE with α2M* was analyzed using a competition ELISA format. The plates were coated with purified α2M* and incubated with biotinylated DIIIE1 PRS (DIIIE1PRSbiot) in the presence of varying concentrations of each DIIIE1 PRS alanine mutant, then detecting α2M*-bound DIIIE1PRSbiot with a streptavidin-peroxidase conjugate. Optical density vs. concentration readings were fitted to a dose-response curve, used to calculate the $IC_{50}$ of each mutant as well as that of wild-type recombinant DIIIE1 PRS.

As observed in FIG. 7, the replacement by alanine of either one of five residues (Lys361, Glu262, Pro264, Val365 and Lys385) of domain III results in every case in an increase of $IC_{50}$ (decrease of the affinity of the interaction) of over one order of magnitude. Taking a 2-fold increase in $IC_{50}$ as a threshold, mutations to alanine of a total of 13 residues affect the interaction. The residues in this group of 13, in addition to the five residues mentioned above, are Glu342, Thr34, Arg350, Lys363, Asn366, Pro372, Gly374 and Glu375.

These results imply that binding of DIIIE to α2M* involves two independent surface patches in DIIIE (FIGS. 7 and 8): one located on its upper surface (where the N-terminus is found) and another on its lower surface (the one close facing the C-terminus). The top patch contains the residues contributing the most to the interaction, including the group of five whose replacement by alanine results in an over 10-fold decrease in affinity. Hence, this patch can be considered a primary site for the interaction between DIIIE and α2M*. Its essential residues are a contiguous linear segment of Lys361-Asn366 and residue Lys385.

The second patch mentioned above, located to the lower surface of DIIIE (FIGS. 7 and 8) is formed by residues Glu342, Thr346, Arg350, Pro372, Gly374 and Glu375. Replacing either of these residues by alanine produces a smaller decrease in affinity than similar replacements on residues of the top patch; therefore, this bottom patch can be considered a secondary interaction site.

The results obtained in this experiment addressed at mapping the sites on the surface of DIIIE involved on its interaction with α2M* demonstrate the soundness of the principles followed for designing the beta hairpin peptides of the present invention. For instance, care was taken to include lysine residues that constituted structural/functional mimics of Lys385 of DIIIE, and it turns out that this is the residue individually contributing the most to the interaction (its mutation to alanine reduces the affinity of the interaction by over 22-fold). The peptide residues mimicking this residue are: Lys8 in PHB2 and d-Lys8 in PHB5, Lys9 in PHB1, PHB6 and PHB7, Lys10 in PHB4 and Lys11 in PHB3, PHB8 and PHB9. In another example, four of the beta hairpin peptides that most potently inhibit the interaction of DIIIE with α2M* (PHB4, PHB5, PHB8 and PHB9, FIG. 5, Example 3) have a residue that structurally/functionally mimics Glu375 of DIIIE, which is the most important residue of the secondary binding site determined in this Example. The residues in the beta hairpin peptides that mimic Glu375 are Glu3 in PHB3, PHB4, PHB8 and PHB9, and Glu16 in PHB5 and PHB6. In other words, the beta hairpin peptides disclosed in the present invention that most potently inhibit the binding of DIIIE to α2M* are those containing, at the same time, the two most important residues of the primary and secondary interaction sites described in this Example.

Example 5

Formation of Supramolecular Structures

Aggregation Kinetics of Peptide PHB4

Light scattering was used to monitor the aggregation of peptide PHB4. The measurements were performed on a Shimadzu™ RF-5301PC (Shimadzu, Japan) spectrofluorimeter, acquiring data with the software provided by the instrument manufacturer. The wavelengths of the incident light beam (excitation) and the detector (emission) were set to 320 nm, using excitation and emission apertures of 5 nm. The scattering of light due to the peptide was calculated by subtracting, from the intensity of the light dispersed by the peptide, the intensity of the light dispersed by a solution without peptide (blank). Variations on light scattering due to the dissolution of the peptide in PBS were studied by acquiring data in time course mode, with a measurement frequency of 1 or 2 per second. The solutions of PHB4 in PBS were prepared by mixing one part of a solution of the peptide in water with one part of a PBS 2X solution.

The data acquired in this experiment revealed that once dissolved into PBS, and after a latency period shorter than 2 min, the intensity of the light dispersed by the peptide increases rapidly during the first 30-40 min and then continues to slowly increase at a linear rate up to 300 min, when the measurement finished. FIG. 9 depicts the behavior of the ratio of the dispersed light relative to the dispersed light at time zero $$\left(\frac{I}{I_0}\right)$$

for peptide concentrations of 5 and 10 μM. The profiles for both concentrations are similar, although the $$\left(\frac{I}{I_0}\right)$$

maximum at 5 μM is larger (11 vs. 7) than that at 10 μM, suggesting that the aggregation that takes place at smaller peptide concentrations leads to the formation of aggregates of a larger average size compared to the original average size. The charts were prepared with SigmaPlot 10.0 (Systat Software Inc., USA).

Analysis by Transmission Electron Microscopy of the Morphology of the Supramolecular Structures formed by Peptide PHB4

In order to analyze the morphology of the aggregates formed by peptide PHB4, peptide solutions were subjected to different experimental treatments where conditions such as temperature, incubation time and the presence of electrolytes were manipulated to facilitate aggregation (FIG. 10). For this particular study, two peptide solutions (2 mg/mL, 0.73 mM) were prepared, one in water and another in PBS. A sample was then taken from each, directly fixed on the grids and observed under the microscope (T0 samples). The remainder was incubated for 1 hour at 50° C. and then samples were taken and fixed immediately (T1 samples). The remainder was then incubated for an additional 2 hours at room temperature, and then fixed (T2 samples).

As observed in FIG. 10A, when dissolved in water the peptide forms particulates with a diameter of 5-20 nm at room temperature. Together with the particulates, the 50° C. treatment induces the appearance of protofibril/fibril-type filamentous structures with a size of 5-10 nm (FIG. 10E). There is a latency period for the formation of fibrils in water, as they are detected in the T2 sample only after the thermal treatment. Fibril formation is favored at higher ionic strengths (PBS), since longer (5-20 nm) filamentous structures are formed immediately after dissolving the peptide in PBS (FIG. 10B), which continue increasing in number after heating the sample for 1 hour at 50° C. (FIGS. 10D and 10F). These results demonstrate that higher temperature and ionic strength favor the aggregation of peptide PHB4.

Also, the study clearly indicates that peptide PHB4 forms supramolecular aggregates whose morphology depends on exact medium composition and temperature. The dimensions of the observed fibrillary structures are consistent with those of amyloid-type structures, which typically grow as elongated fibers through the formation of extended beta sheets.

The outcome of protein aggregation processes depends on the exact balance between repulsion and attraction among protein molecules (Juárez, J., et al. (2009) *Biophysical Journal* 96[6], 2353-2370). It is known that adding electrolytes to protein solutions often increases the rate of formation of fibrils, due to the shielding of electrostatic repulsions between protein molecules by said electrolytes, which thus tips the balance towards attractive intermolecular interactions and, hence, the formation of aggregates (Juárez, J., et al. (2009) *Biophysical Journal* 96[6], 2353-2370; Sagis, L. M., et al. (2004). *Langmuir* 20, 924-927). The kinetics of the process of intermolecular interaction is also favored by temperature, which has long been known to play a fundamental role on the induction of protein aggregation.

Example 6

Figure 11:
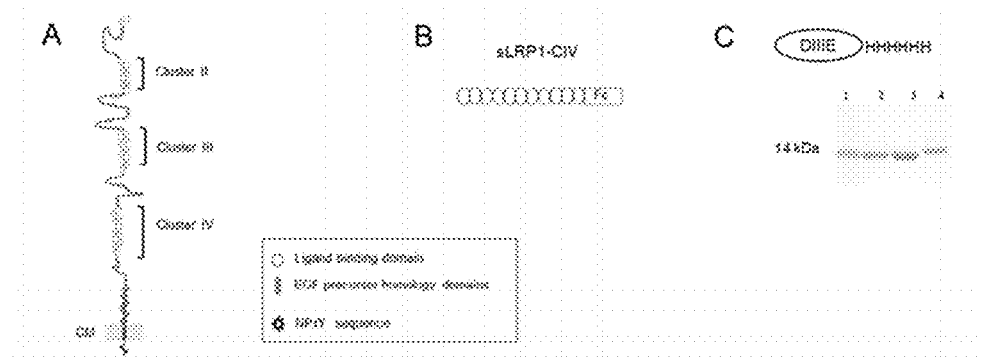
FIG. 11. Proteins used in the assays for direct interaction of DIIIE with the LRP1 receptor. A) Schematic representation of the domain architecture of LRP1. CM: cytoplasmic membrane. The regions corresponding to the ligand binding clusters are indicated. B) Schematic representation of the chimeric sLRP1-CIV protein. Fc: immunoglobulin constant region. C) Schematic representation of recombinant DIIIE1-4 proteins. D) Analysis by denaturing electrophoresis (SDS-PAGE) of the final DIIIE preparations: 1. DIIIE1 (specifically, DIIIE1J), 2. DIIIE2, 3. DIIIE3 and 4. DIIIE4. The position corresponding to the 14 kDa marker in the molecular weight ladder used in the experiment is indicated.
Figure 12:
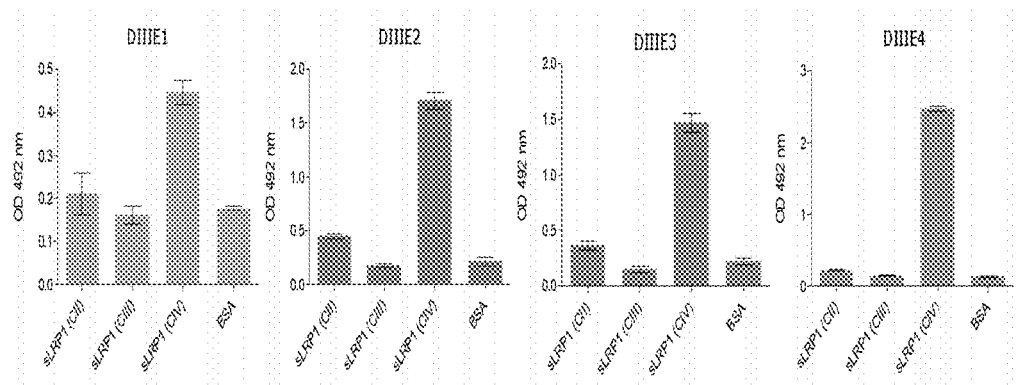
FIG. 12. Interaction of DENV DIIIE with the ligand binding clusters of LRP1 in an ELISA assay. The protein used to coat the wells of the plates is indicated at the top of each chart. Binding of sLPR1-CII-IV proteins was detected using a polyclonal anti-Fc of human IgG conjugated to horseradish peroxidase.

Study of the Interaction of Beta Hairpin Peptides with a Fragment of the LRP1 Receptor It is known that DENV infection can be blocked by molecules that interfere with the interaction between DENV virions and the cell receptor known as LRP1 (Huerta H. et al, WO 2007/124698). LRP1 is an integral membrane protein (FIG. 11A) formed by an approximately 500 kDa α chain associated non-covalently to an 85 kDa β chain (Anna P. Lillis, et al. (2008) *Physiol Rev* 88: 887-918). The extracellular region of this receptor is formed by the entire α and part of the β chain, which contains a transmembrane segment and two NPxY motifs for interacting with intracellular proteins involved in receptor signaling and endocytosis. LRP1 is a constitutive endocytic receptor that is able to internalize over 30 different ligands, and has been shown to be involved in a number of important processes including the metabolism of lipids, hemostasis, the activation of lysosomal enzymes and neurotransmission.

It is the α chain of LRP1 that interacts with extracellular LRP1 ligands. This chain exhibits the typical domain architecture of members of the family of low density lipoprotein receptors, to which LRP1 belongs. Specifically, the α chain of LRP1 contains four clusters containing 2 (cluster I), 8 (cluster II), 10 (cluster III) and 11 (cluster IV) ligand binding sites structurally related to the Cys-rich regions of proteins of the complement cascade. After each ligand binding site cluster there is an Epidermal Growth Factor (EGF)-like domain, formed by Cys-rich regions and YWTD domains.

Figure 13:
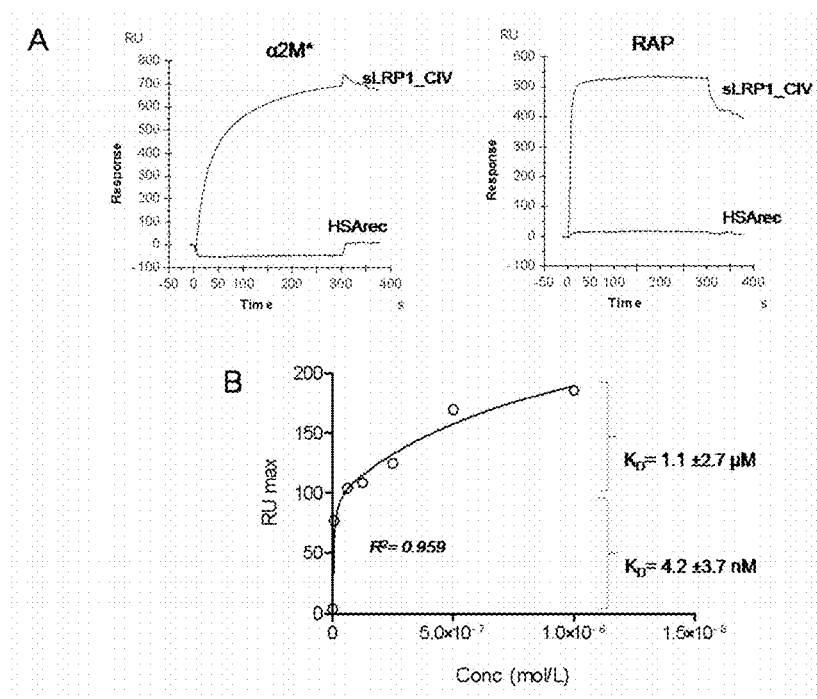
FIG. 13. Characterization of the sLRP1-CIV binding surface for a Biacore assay. A) Sensorgrams obtained from the application of α2M* and the Receptor-Associated Protein (RAP), both at 100 nM. The signals from both channels are shown: Fc1, with immobilized sLRP1-CIV and Fc2, with immobilized recombinant HSA. B) Determination of the affinity of the interaction of RAP with sLRP1 from maximal Resonance Units (RU) against concentration data. The continuous line represents a fit to a two interaction sites model, performed using GraphPad Prism v5.03. The measurements were performed on a Biacore X unit.

In order to determine whether the ligand binding domains of LRP1 interact with DIIIE from DENV, recombinant DIIIE proteins were prepared from residues 289-399 of protein E from DENV1 strain Jamaica/CV1636/1977 (DIIIE1J); residues 289-399 of protein E from DENV2 strain Jamaica 1409 (DIIIE2); residues 287-397 of protein E from DENV3 strain H-87 (DIIIE3) and residues 289-399 of protein E from DENV4, strain Dominica 814669 (DIIIE4), fused to a C-terminal hexahistidine tag (SEQ ID No. 19-22), as shown in FIG. 11C. The proteins DIIIE1J and DIIIE2-DIIIE4 were obtained by heterologous expression in *E. coli* and purified by immobilized metal affinity chromatography (IMAC), obtaining preparations with a purity of over 90%, as evidenced by SDS-PAGE analysis (FIG. 11D).

Also, the experiment used three recombinant proteins containing clusters II, III or IV from LRP1, denominated sLRP1-CII (SEQ ID No. 23), sLRP1-CIII (SEQ ID No. 24) and sLRP1-CIV (SEQ ID No. 25), respectively, fused to the constant region of a human IgG1 molecule (R&D Systems, USA) (FIG. 11B).

The evaluation of DIII/LRP1 interactions was performed with an ELISA assay, in which 96-well plates were coated with proteins DIIIE1J or DIIIE2-DIIIE4 at 10 μg/ml, then blocked with Bovine Serum Albumin (BSA) and incubated for 1 hour at 37° C. with either sLRP1 CII, sLRP1 CIII or sLRP1 CIV at 10 μg/m1 in 20 mM HEPES pH 7.5/150 mM NaCl/1 mM $CaCl_2$/0.05% Tween 20. After washing, the plates were then incubated for 1 hour at 37° C. with a 1:1000 dilution of an anti-human IgG-peroxidase conjugate and developed with o-phenylenediamine/$H_2O_2$. The obtained data revealed a similar pattern of interactions for DIIIE from all four serotypes, where sLRP1-CIV exhibited the strongest binding followed by sLRP1-CII while sLRP1-CIII showed no detectable binding to any DIIIE molecule (FIG. 12).

The interaction of the beta hairpin peptides with soluble fragments of the LRP1 receptor was studied by Surface Plasmon Resonance (SPR), using a Biacore X unit. In this technique, one of the interaction partners to be studied is immobilized on the surface of a chip, and the other interaction partner is dissolved in a solution that runs through the measurement cell on top of the interaction surface, under conditions of controlled flow. The association and dissociation of interacting partners is measured in resonance units (RU) and plotted, as a function of time, on charts known as 'sensorgrams'. SPR, therefore, enables the experimenter to obtain detailed information about the interaction without having to label either interaction partner.

In this example, one channel of a CM5 chip (GE Healthcare, USA) was used to immobilize protein sLRP1-CIV on its surface at high density (see Table 6) and recombinant Human Serum Albumin (rHSA, Sigma-Aldrich, USA) was immobilized on the other channel. Based on the RU density achieved for each molecule, and assuming that there are 11 potential interaction sites for each sLRP1-CIV molecule and one potential interaction site for each HSA molecule, the surfaces at both channels would thus exhibit a similar density of binding sites per surface area unit (pmol/$mm^2$).

TABLE 6

Summary of the characteristics of the binding surfaces in the CM5 chip used to evaluate interactions with sLRP1-CIV

| Channel | Ligand | Molecular weight (kDa) | Immobilized RU | Binding sites (pmol/ $mm^2$) | Protein conc. at surface of the chip (mol/L) |
|---|---|---|---|---|---|
| Fc1 | sLRP1_CIV | 77 | 1,665 | 0.2 | $2.2 \times 10^{-4}$ |
| Fc2 | rHSA | 67 | 10,108 | 0.2-0.1 | $1.5 \times 10^{-3}$ |

The reactivity of the immobilized protein was evaluated using two known LRP1 ligands; namely, α2M and the protein known as Receptor-Associated Protein (RAP). It has been previously demonstrated that both molecules interact with cluster IV of the LRP1 receptor (Jaap G. Neels, et al. (1999). *Journal of Biological Chemistry,* 274, 44: 31305-31311). FIG. 13 shows the results of this verification. As can be observed, loading either α2M or RAP increases the detected signal (RU) on the sLRP1-CIV channel, but fails to produce an increase in signal strength on the rHSA channel. This result demonstrates that the immobilized sLRP1-CIV is capable of establishing a specific interaction with both ligands.

Although it was decided to immobilize sLRP1-CIV at high density because these conditions make easier the detection of any potential interactions with compounds whose molecular weight is lower than that of average proteins (such as the peptides this experiment is intended to study), it must be stressed that in high-density surfaces, mass transfer limitations and the possibility of multivalent binding make difficult the accurate determination of kinetic constants. Therefore, and in order to characterize in greater detail the sLRP1-CIV binding surface, different RAP dilutions (0.6-20 µM) were loaded, and RU were registered under conditions of interaction equilibria (250 sec, see FIG. 13B). The behavior exhibited by the resulting maximum RU vs. concentration curve fits well that of a double site model where there is a high-affinity interaction with a Kd of 4.2 nM and a low-affinity interaction with a Kd of 1.1 µM. These data are consistent with other results obtained in different studies analyzing the binding of RAP to LRP1, which indicate that RAP establishes a multi-point interaction with clusters II and IV of LRP1 with an affinity in the 6-18 nM, and that loss of multivalency in this interaction leads to affinity constants in the micromolar range. Hence, in this experiment the presence of an interaction whose affinity sits at the micromolar range might be explained by the high density of immobilized sLRP1-CIV at the surface of the chip, which facilitates the loss of multivalent interactions at high RAP concentrations. The data also indicate that immobilized sLRP1-CIV faithfully reproduces the previously reported characteristics of the LRP1-RAP interaction.

The binding of beta hairpin peptides to sLRP1-CIV was studied by loading 20 µM dilutions in running buffer of the different peptide variants onto the sLRP1-CIV chip characterized above. The high strength of the resulting signals is consistent with the binding of aggregated, rather than monomeric forms of the peptides. Therefore, the observed variations between different peptides may reflect either differences in the affinity of unitary peptide interactions or differences in aggregation numbers and/or geometries that lead to variations in the number of peptide units able to simultaneously engage immobilized sLRP1-CIV molecules in a multivalent manner. In the case of peptides of the HDIII3CL family (peptides 10-14 in Table 1), variant HDIII3CL2 exhibits the strongest binding. There is also detectable specific binding in the case of variants HDIII3CLW and HDIII3CLK, although the strength of the interaction is much lower, suggesting that the replacement of residues Trp17 and Lys14 has a deleterious effect on binding to sLRP1-CIV. There is an at most marginal interaction in the case of variant HDIII3CLC, indicating that the replacement of residues C1 and C18 (in other words, the elimination of the disulfide bridge) affects dramatically the strength of the interaction of the peptide with sLRP1-CIV. This result is consistent with previous data on the potency of the antiviral activity exhibited by the peptides, since HDIII3CLC, HDIII3CLW and HDIII3CLK, whose binding to sLRP1-CIV is decreased relative to HDIII3CL, did not exhibit in vitro antiviral activity against DENV2 in Vero cells (see Table 2). On the other hand, the stronger binding to sLRP1-CIV exhibited by HDIII3CL2 does not translate into a more potent antiviral activity compared to HDIII3CL (see Table 2), indicating that receptor binding per se is necessary but not sufficient for antiviral activity. One possible explanation for this finding is that there is a fraction of HDIII3CL2 that binds to sites in sLRP1-CIV that do not play a relevant role in the virus-receptor interaction, and/or that it is binding with very low affinity; a reasonable supposition taking into account the multi-domain architecture of receptor LRP1 and its clusters. The difference between peptides HDIII3CL2 and HDIII3CL is that the former has an additional C-terminal lysine and has, therefore, a stronger cationic character, which may facilitate additional electrostatic interactions with the negatively charged LRP1 receptor. In addition, it must be pointed out that Lys21 does not form part of the hairpin, which is the topological region that mimics the functional patch in DIIIE described previously (Huerta V. et al, WO 2007/124698) and in this invention.

Figure 14:
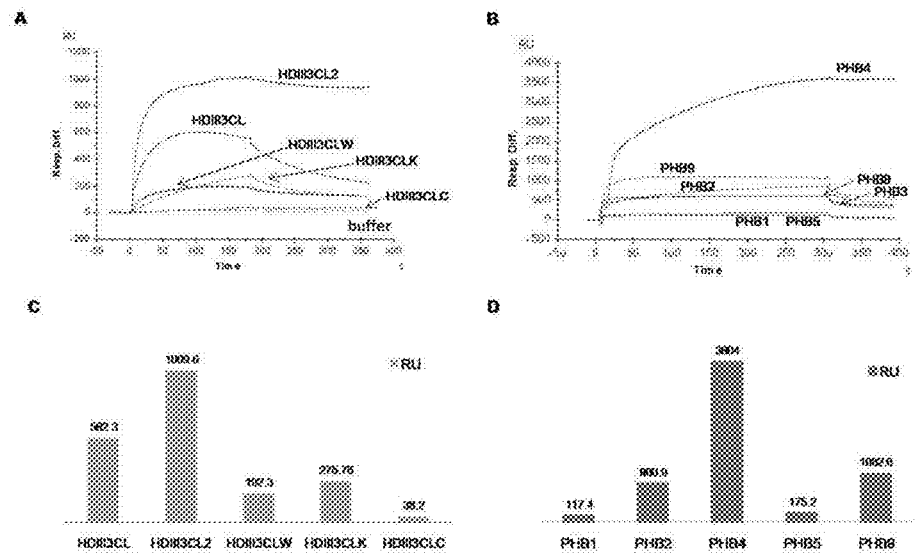
FIG. 14. Biacore assay for the interaction of beta hairpin peptides with sLRP1-CIV. A and B) Sensorgrams obtained from the application of the peptides at 20 μM; C) RU observed at 160 s, and (D) RU at 270 s.

The same procedure was followed to evaluate the interaction of the beta hairpin peptides PHB1, PHB2, PHB3, PHB4, PHB5, PHB8 and PHB9 with the sLRP1-CIV surface. As shown in FIGS. 14B and 14D, peptide PHB4, which in previous assays was the most potent antiviral peptide of this series, also exhibited the strongest binding by SPR to sLRP1-CIV. Peptides PHB2, PHB4 and PHB9 also exhibited maximum binding above that of peptide HDIII3CL (FIGS. 14A and 14C), in correspondence with their in vitro antiviral activity. A comparison of the maximum binding of peptides of the same size and beta turn type (PHB1-2, PHB3-4 and PHB8-9) shows that peptides PHB2, PHB4 and PHB9 are better binders than their counterparts (PHB1, PHB3 and PHB8), paralleling their behavior in antiviral activity assays (see Example 2).

Example 7

Correlation Between the Antiviral Activity of Beta Hairpin Peptides and their Binding to Receptor LRP1 and Protein α2M*

Figure 15:
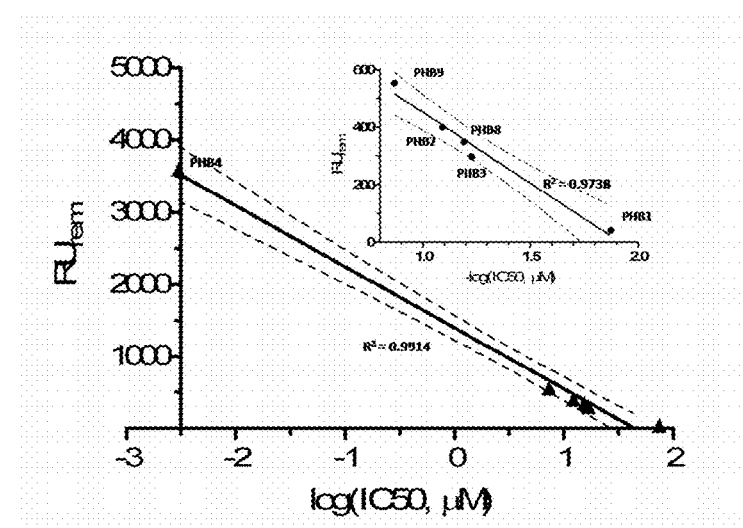
FIG. 15. Relationship between binding to protein LRP1 (sLRP1-CIV fragment) and the in vitro antiviral activity of beta hairpin peptides. Linear regression was used to fit in vitro potency data [log(IC50,uM)] for antiviral activity against DENV2 in Vero cells and the magnitude of Biacore signals at t=400 s ($RU_{rem}$) for peptides of the PHB series with the same topology as peptide HDIII3CL (native topology). The 95% confidence band is shown with dashed lines. The inset depicts a similar analysis but excluding peptide PHB4.

Receptor LRP1 has been previously proposed as the putative endocytic receptor for DENV, and a 'bridging' or 'carrier' role has been ascribed to protein α2M* (an LRP1 ligand) in the process of virus entry into the cells (Huerta V. et al, WO 2007/124698). The previous example (Example 6) demonstrated that the beta hairpin peptides disclosed in the present invention can bind a fragment of receptor LRP1. The present example, in turn, examines whether the antiviral activity observed in Example 2 correlates quantitatively with the capacity of these peptides to bind receptor LRP1. As can be observed in FIG. 15, the logarithm of the $IC_{50}$ values ($-pIC50$) of the antiviral activity of the peptides in Vero cells exhibits a linear dependence on the value of the Biacore signals observed with run lengths of 400 s (RUrem). In this case, only PHB peptides sharing the same topology, according to Table 1, are shown. Not only is the potency of the antiviral activity of peptide PHB4 much higher than the rest, but peptide PHB4 outperforms considerably the others in terms of LRP1 binding. The linearity of the relationship observed above remains constant even if the PHB4 data are excluded (inset in FIG. 15), as the linear regression coefficient ($R^2$) is 0.99 with the PHB4 data and 0.97 without them. Analyzing the inset data, a prediction can be made that, should the linear dependence be maintained for PHB4, the Biacore binding values would correspond to an antiviral potency in the nanomolar range, which is consistent with the experimentally determined potency in Example 2.

The pIC50 data for the antiviral activity of peptides with a common topology exhibits a statistically significant correlation with RUrem values (r(Pearson)=−0.9957 and P<0.0001). If the peptide PHB4 data are excluded, the values of Pearson's correlation coefficient remain similar (r(Pearson)=−0.9868, P=0.0018). The analyses of correlation, linear regression and the charts were prepared with Prism v5.03 (GraphPad Software Inc., USA).

These results are consistent with an antiviral action mechanism whereby PHB peptides disturb the interaction between virions and the LRP1 receptor, leading to the inhibition of productive virus entry into the cells.

Figure 16:
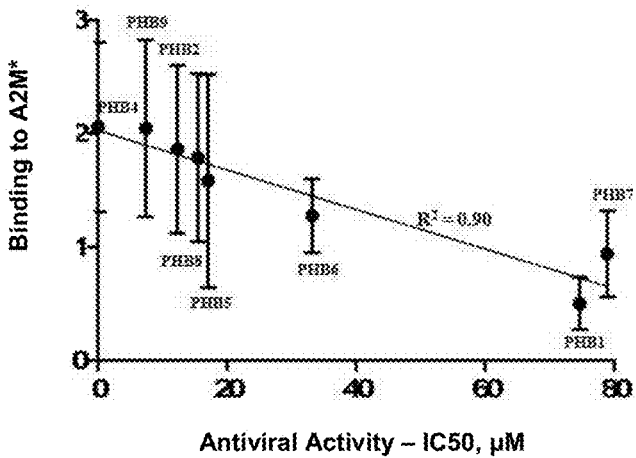
FIG. 16. Relationship between binding to protein α2M* and the in vitro antiviral activity of beta hairpin peptides. Linear regression was used to fit data for the inhibition of binding of DIIIE to protein α2M* and IC50 values for the inhibition of the infection of Vero cells by DENV2. Percentage inhibition of the binding to α2M* is expressed relative to the inhibition percentage determined for recombinant DIIIE1J at concentrations equimolar to those used for the peptides. The values shown correspond to means and standard deviations, determined at submicromolar and nanomolar peptide concentrations (50, 100, 200 and 400 nM).

A similar analysis was carried out regarding the ability of PHB peptides to inhibit the binding of DIIIE to protein α2M* in the submicromolar/nanomolar range. As shown in Example 3, at that concentration range the peptides inhibited partially the binding of biotinylated DIIIE1J (DIIIE1Jbiot) to α2M*, with peptides PHB2, PHB4, PHB5, PHB8 and PHB9 exhibiting better (1.5- to 3-fold) inhibition percentages than DIIIE1J alone. In this case, the inhibitory capacity of the peptides (relative to the capacity of recombinant DIIIE1J to inhibit DIIIE1Jbiot binding to α2M*) also correlates with their antiviral activity against DENV2 in Vero cells, as shown in FIG. 16. Spearman's correlation coefficient between the $IC_{50}$ values and the α2M* inhibition percentage (relative to the inhibition percentage of recombinant DIIIE1J) is Rs=−0.9762, P=0.0004; a result that suggests that the beta hairpin peptides disclosed in the present invention may interfere with the role played by protein α2M* during entry of the virus to the cells.

Example 8

Effect of Agents that Affect Aggregation on the Antiviral Activity of Peptide PHB4

The antiviral activity of peptide PHB4 was evaluated after treatments facilitating its aggregation or in the presence of different agents that modulate aggregation, with the purpose of examining their effect on the inhibitory activity of this peptide for the infection of Huh7.5 cells with DENV2 strain S16803. Huh7.5, a human hepatoma-derived cell line, was selected not only because it is permissive for DENV2, but because of its relevance as an experimental system from the viewpoint of DENV pathogenesis (Lin Y L, et al. (2000) *J Med Virol.;* 60(4):425-31).

Based on the results shown in Example 5, which evidence that changes in ionic strength result in changes to the size and morphology of peptide aggregates, an experiment was designed in which, starting from a concentrated solution of PHB4 in water, the peptide was dissolved either in (i) MEM medium or (ii) PBS (containing respectively 6.8 g/L and 8.0 g/L of NaCl, and with pH adjusted to 7.4) and subjected to the different conditions to be evaluated.

Antiviral activity was evaluated in virus yield assays, in which 80-90% confluent Huh7.5 monolayers were washed twice with non-supplemented DMEM and then infected at a m.o.i of 0.01 for 2 h at 37° C. and 5% $CO_2$ in the presence of the different peptide preparations, after which the viral inoculum was removed by washing with non-supplemented DMEM, and the cells were grown in DMEM supplemented with 2% FBS. Cell supernatants were collected at 24 h p.i., and virus yields were determined by titrating the supernatant in a plaque formation assay (Morens D. M., et al. (1985). *N. J. Clin. Microbiology;* 22: 250-254).

It is well known that temperature influences significantly the aggregation, or self-assemblage of peptides into supramolecular structures (Sabaté R, et al. (2012). *Biomacromolecules;* 13(2):474-83). Therefore, a first series of assays was set up in which, starting from a 20 μM solution of the peptide in water, dilutions were prepared in MEM spanning the 10-0.01 μM concentration range, which were then incubated in parallel at 10° C. and 37° C. for 2 hours and then used in a viral inhibition assay. Non-incubated peptide dilutions (that is, prepared right before the viral inhibition assay) were used as controls.

Figure 17:
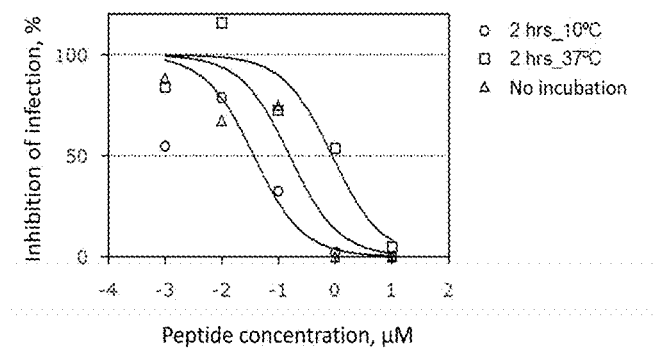
FIG. 17. Influence of incubation temperature on the antiviral activity of peptide PHB4. Antiviral activity was evaluated by titrating 24 h post-infection (p.i.) supernatants from Vero cells infected with DENV2 strain 16803, using a plaque formation assay on Vero cells. IC50 were estimated using GraphPad Prism v5.03. The continuous line represents a non-linear fit to a $\log_{10}$ (concentration) vs response curve.

The results show that the non-incubated peptide, dissolved in MEM medium, inhibited viral infection in a dose-dependent manner, with an $IC_{50}$ of 0.16 μM and an $IC_{100}$ of 10 μM (FIG. 17, Table 7). However, pre-incubating the peptide in MEM at 10° C. produced a sharp increase in potency, as $IC_{50}$ dropped to 0.037 μM, while incubating it at 37° C. produced the opposite effect, as its $IC_{50}$ increased to 0.89 μM. The results indicate that temperature plays a decisive role in the process of peptide aggregation, as in this preliminary experiment it produced variations in potency as large as 24-fold.

TABLE 7

IC50 for peptide PHB4 incubated at 10° C. or 37° C.

| Additive | Treatment | | |
|---|---|---|---|
| | No incubation | 2 hrs-10° C. | 2 hrs-37° C. |
| — | 0.16 (0.83*) | 0.037 (0.60) | 0.89 (0.87) |

$IC_{50}$ for each experimental condition was determined from non-linear fits of the data, performed using Prism v5.03.
*The number in parentheses is the value of the regression coefficient for the fit ($R^2$).

Figure 18:
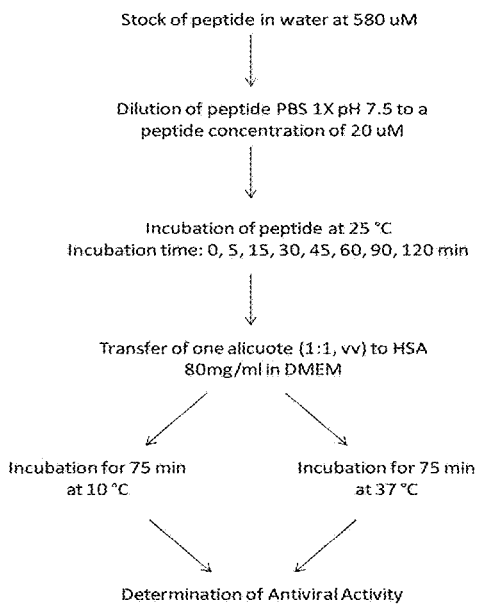
FIG. 18. Scheme depicting the experimental design used to evaluate the influence of aggregation time on the antiviral activity of peptide PHB4.

A second experiment was designed to determine the influence of aggregation time on the antiviral potency of peptide PHB4 (FIG. 18). In this experiment, the peptide was incubated in PBS for different intervals, and then diluted in one volume of 80 mg/mL HSA in DMEM with the purpose of stopping the aggregation process (HSA is a potent aggregation modulator that has been shown to inhibit both the initial nucleation and the growth of amyloid β peptide fibrils, see Reyes A., et al. (2009) *Journal of Biological Engineering,* 3:5) before evaluating the antiviral activity of the resulting mixture. This incubation with HSA was performed in parallel at either 10° C. or 37° C. (FIG. 18), and further dilutions of these peptide samples for evaluating their antiviral activity were performed in 40 mg/mL HSA solutions in DMEM.

Figures 19, 20:
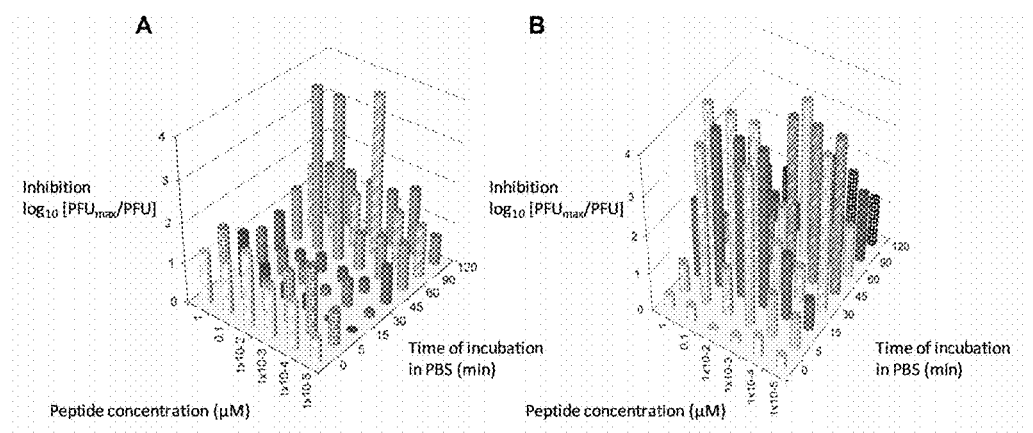
FIG. 19. Influence of incubation time and temperature on the antiviral activity of peptide PHB4. Antiviral activity was evaluated by titrating 24 h p.i. supernatants from Vero cells infected with DENV2 strain 16803, using a plaque formation assay on Vero cells. The viral titer in untreated controls (no peptide treatment) was 4 $\log_{10}$. A. Incubation at 10° C.; B. Incubation at 37° C.
FIG. 20. Experimental design used to evaluate the influence of the initial concentration of peptide PHB4 during the aggregation process on the potency of its antiviral activity.

As shown in FIG. 19, under the conditions of the assay the antiviral activity values of the peptide yielded a bell-shaped dose-response curve indicating the existence of an optimum range of peptide concentrations for its inhibitory activity. This type of response is commonly seen in the activity of many different biological systems, and although there is not a single mechanism of action underlying this behavior, a common element in all instances is the existence of multivalent interactions between the molecules in case.

The results evidence that the inhibitory activity of the peptide is sensitive to the length of the incubation period in PBS for the formation of aggregates of higher potency, where potency is understood, in this case, as the lowest peptide concentration that decreases by 50% the viral yield of the infection control for the assay. On the other hand, the incubation with HSA at 10° C. leads to the formation of lower potency variants, compared to the results obtained by incubation at 37° C. This confirms that there probably is an interaction between the peptide, or still-growing aggregates thereof, with HSA, wherein the course of the aggregation process is changed, leading to the formation of high-potency variants such as those obtained by incubation for 45-60 min. in PBS and then incubation with HSA at 37° C., that can produce total inhibition of the infection by DENV in this assay format at peptide concentrations as low as 1 nM-10 pM.

The starting concentration of the peptide is another parameter that may influence the kinetics and final results of the aggregation process in a significant manner. In order to dissect how this parameter influences the antiviral activity of peptide PHB4, an assay was set up (represented diagrammatically in FIG. 20) in which solutions of the peptide in water at concentrations ranging from 100 μM to 2 μM were diluted with one volume of MEM 2X and incubated for 2 h at 25° C., after which dilutions in non-supplemented DMEM medium were prepared and assayed for antiviral activity.

Figure 21:
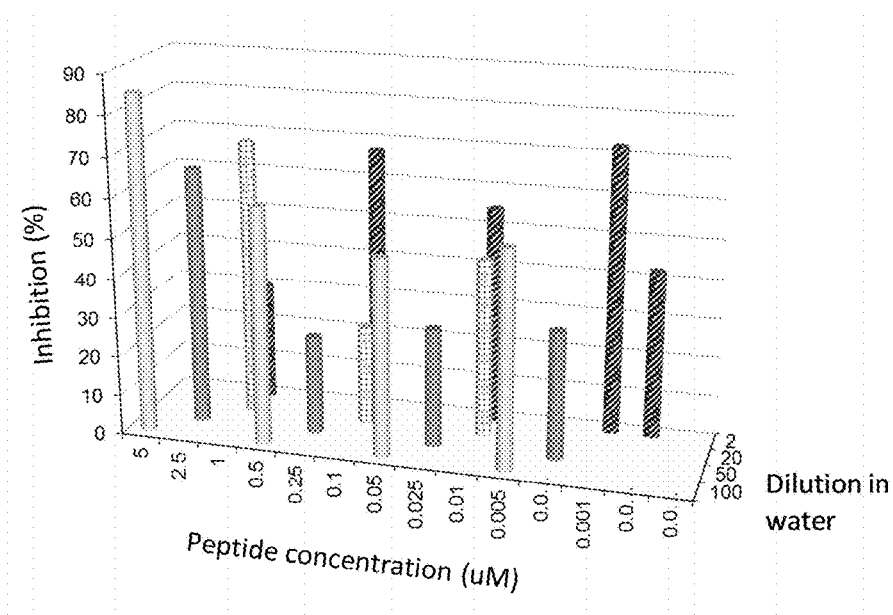
FIG. 21. Influence of the initial concentration of the peptide in water on its antiviral activity. Antiviral activity was evaluated by titrating 24 h p.i. supernatants from Vero cells infected with DENV2 strain 16803, using a plaque formation assay on Vero cells.
Figure 22:
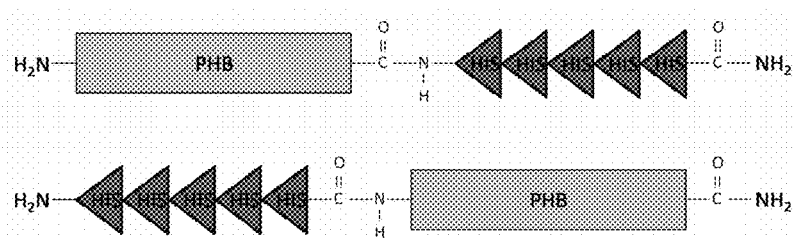
FIG. 22. Design of the fusion of PHB to a C-terminal (top) or N-terminal (bottom) histidine tag.
Figure 23:
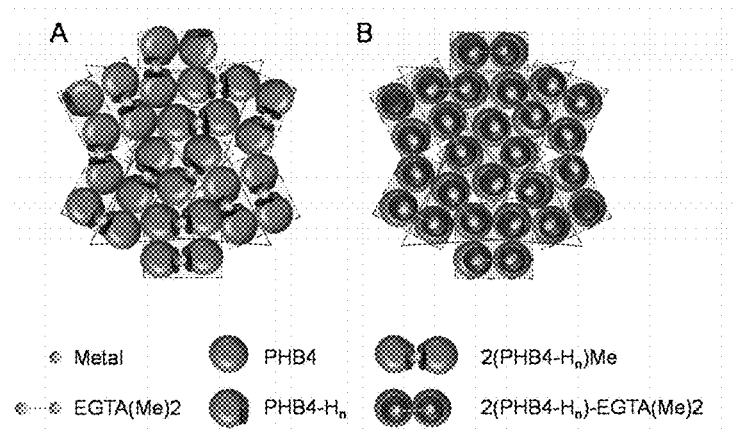
FIG. 23. Scheme representing histidine-tagged peptide aggregates/nanoparticles stabilized by cross-linking with metal ions and EGTA(Me2) spacers.

The results demonstrate that there is a relationship between antiviral activity and the initial concentration of peptide PHB4 in water before its addition to a solution of higher ionic strength to trigger the process of aggregate growth (FIG. 21). In addition, the data also evidence a change in the dose-response behavior, confirming an evolution towards aggregate structures that are different, depending on the initial conditions of the dissolution of peptide in water. The most potent forms show again a bell-shaped dose-response curve, and are obtained for a condition where the peptide was found in the highest initial dilution in water evaluated in this assay.

In all, the results evidence that peptide PHB4 can assemble into aggregated forms with an antiviral potency in the nanomolar/subnanomolar range, depending on aggregation conditions. It should be stressed that the antiviral activity assay used in these experiments is one of the most stringent tests for this purpose, as the molecule under evaluation is present only during the initial stage of the infection and is later removed during subsequent washes of the cell monolayer. Therefore, that fact that antiviral activity was detectable with this experimental set up is consistent with a mechanism of action for peptide PHB4 whereby it inhibits one of the early stages of viral entry into the cell; namely binding to the cell surface, internalization or membrane fusion.

Example 9

Protection in an Animal Model of Viral Infection

An experiment was set up to evaluate the in vivo antiviral activity of peptide PHB4 and compare it to that of peptide HDIII3CL. For this purpose, groups of 12 adult Balb/c mice (20 g average body weight) were anesthetized by ether inhalation and inoculated intracranially with 20 μL of viral preparations containing 10 times the median lethal dose of this model and the peptide to be evaluated. The animals recovered quickly and already appeared alert five minutes after the treatment, and were monitored afterwards for 21 days. The data were evaluated using the Kaplan-Meier logarithmic rank test.

Table 8 contains the results of the experiments performed with the four DENV serotypes. At the assayed dose, peptide PHB4 affords total protection to the mice, and is therefore more potent than peptide HDIII3CL. In the case of the DENV2 strain, the experiment was repeated thrice.

TABLE 8

Summary of the results of the in vivo protection assays

| | | Protection (%) | | | |
|---|---|---|---|---|---|
| Peptide | Dose | DENV1 | DENV2 | DENV3[a] | DENV4 |
| PHB4 | 30 μg | 100*** | 100*** | 100*** | 100*** |
| HDIII3CL | 30 μg | 50* | 42** | ND | 17*** |

Statistical significance: *P < 0.005; P < 0.01, *P < 0.05. ND, not determined

[a]The lethal dose for the DENV3 strain used in this assay could not be determined. Therefore, morbidity was evaluated instead, monitoring the mice for the appearance of the following symptoms: ruffled fur, limb paralysis, and hunched posture, and mice showing these signs were euthanized. ruffled fur, hunched posture, prostration, and hind limbs paralysis; and for their duration in days.

Example 10

Fusion of Peptide PHB4 to Polyhistidine Tags for Assembly into Metal-based Nanoparticles We have previously pointed out that the beta hairpin peptides disclosed by the present invention may be produced, using chemical synthesis or recombinant DNA technology, alone or fused to other protein/peptides. Also, it was demonstrated in Example 5 that the beta hairpin peptides disclosed by the present invention may aggregate and adopt different quaternary structures, depending on starting peptide concentration, solvent type and experimental conditions such as temperature, pH, ionic strength, sonication, presence of additives, non-covalent binding to proteins such as HSA, etc. The formation of these supramolecular structures greatly increases the antiviral activity of the beta hairpin peptide (See Example 8), probably due to the fact that the avidity of the interactions of peptide-based nanoparticles with their putative receptor is much higher due to multivalent binding (simultaneous interaction of several monomers in the same nanoparticle with several ligand binding domains in the receptor, or with more than one receptor on the cell surface). In addition, the formation of nanoparticles may contribute positively to the pharmacokinetic properties of the peptide by increasing its serum half life, conferring resistance to serum proteases, etc.

The nanoparticles that the beta hairpin peptides disclosed by the present invention have been shown to form may be further stabilized by fusing said peptides to 'acceptor' (A) groups that can bind non-covalently to 'spacer' (E) molecules or atoms, with a stoichiometry of two or more 'A' groups for each 'E' group. Such a design would enable the association of two or more PHB peptides with a single 'E' spacer. In one embodiment of the present invention, we have thus appended, via chemical synthesis, a tag consisting of five histidine residues to peptide PHB4 (FIG. 22). Polyhistidine tags can function as 'A' groups for polyvalent metal ions, such as Zn(II), Cu(II), Cu(II), Cs, etc. In this case, atoms of the imidazole group that constitutes the side chain of the histidine residue establish coordinate bonds to the metal ion with a stoichiometry of up to four imidazole groups per metal ion. At certain concentrations, therefore, polyhistidine-bound metal ions may act as E groups and promote peptide dimerization.

FIG. 23 depicts diagrammatically how metal ions can be used to link together, both directly and indirectly, different peptides bearing available imidazole groups, by means of coordination to auxiliary chelator groups such as the tetraanionic compounds EGTA (ethylene glycol-bis(2-aminoethylether)-N,N,N',N'-tetraacetic acid) and EDTA (2-({2-[Bis(carboxymethyl)amino]ethyl}(carboxymethyl)amino) acetic acid). In these cases the metal ions form $EGTA(Me)_2$ and $EDTA(Me)_2$ complexes with a stoichiometry of two metal atoms per molecule of diaminetetracarboxylic acid, wherein said metal ions can still form coordinate bonds with additional imidazole groups, thereby acting as 'E' groups that can stabilize the crosslinking of peptides and their aggregates (FIG. 23).

FIG. 22 depicts two of the fusion molecules disclosed by the present invention; one in which the poly-histidine tag is joined to peptide PHB4 via a C-terminal amide bond (PHB4H5) and another in which the tag is appended N-terminally to the peptide in a similar fashion (H5PHB4). Both fusion peptides were synthesized and purified following the procedures previously described in Example 1, and used to prepare 200 μM solutions of each peptide in 10 mM MES pH 6.8-7.5 buffer containing either 2 mM $ZnCl_2$ (which provides the metal ion) or 2 mM of an $EGTA(Zn_2)$ complex, previously obtained by adding $ZnCl_2$ at a final concentration of 8 mM to a solution of 4 mM EGTA.

These peptide preparations (PHB4H5 and H5PHB4, either alone or in complexes with either Zn or $EGTA(Zn_2)$) were then assayed for antiviral activity against DENV2

(strain M2C) in Vero cells. Briefly, the cells were incubated for 1 h at 37° C. in the presence of the peptide preparations, and then the viral inoculum was added at a m.o.i. of 0.001. Two hours later, a layer of high-density medium was added and the plates were incubated for 3 days at 37° C., 5% $CO_2$. Cells incubated only with solutions of $ZnCl_2$ and EGTA ($Zn_2$) at the corresponding concentrations before viral challenge were used as negative controls. The viral plaques were detected using an immunofoci technique with a monoclonal antibody specific for the viral envelope, and inhibition percentages were calculated with the following expression:

$$I=100-100 \times NP_{peptide}/NP_{Negative\ control}$$

Where I stands for the inhibition percentage and NP for the number of viral plaques, averaged across replicates.

Figure 24:
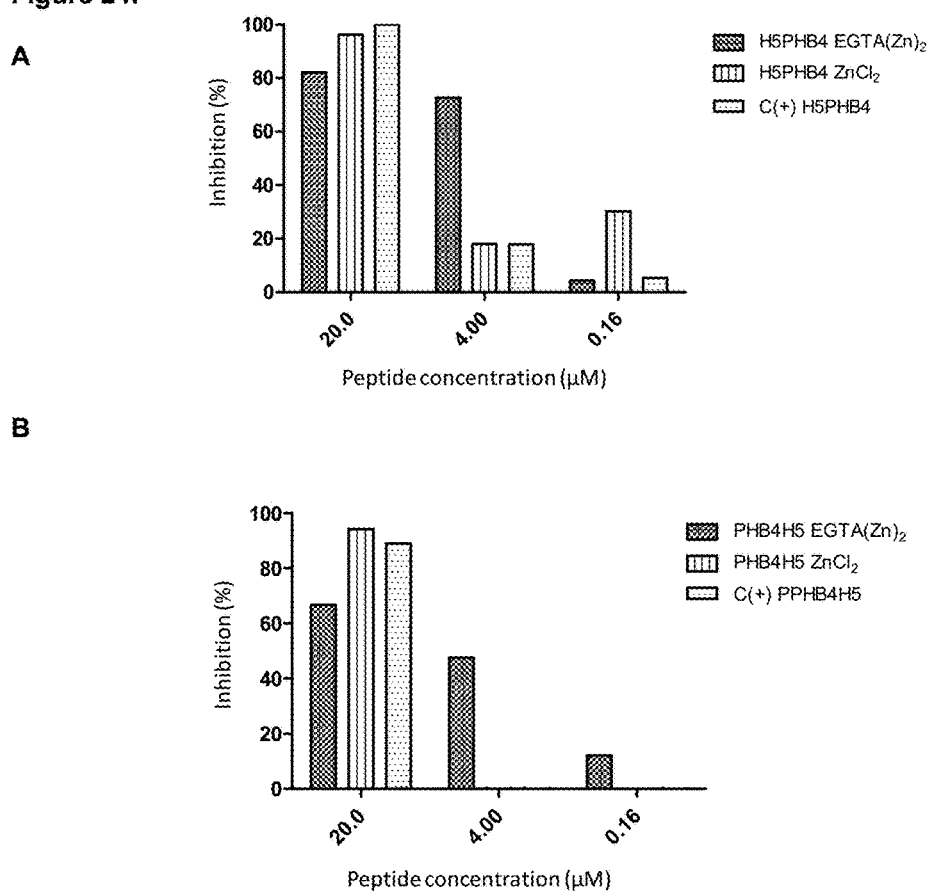
FIG. 24. Antiviral activity of peptides H5PHB4 and PHB4H5, alone or in complex with Zn and EGTA(Zn2).

As can be observed in FIG. 24, although the fusion peptides (alone, without metal additives) are highly inhibitory at a concentration of 20 μM (inhibition percentages close to 100%), the antiviral activity disappears at peptide concentrations of either 4 or 0.16 μM. At these concentrations, however, the complexes of the peptides with the EGTA(Zn2) spacer still exhibit antiviral activity in the range of 50-70% inhibition percentages. Peptide H5PHB4 exhibits an inhibition percentage of 33% at 0.16 μM. These results demonstrate that the fusions of peptide PHB4 to poly-histidine tags exhibit more potent antiviral activity when complexed to spacer agents, particularly to the EGTA($Zn_2$) spacer.

The invention claimed is:

1. A beta hairpin peptide comprising an amino acid sequence selected from the group consisting of SEQ ID NOs: 1 to 9 or an analogue sequence thereof, wherein said analogue sequence:
   (i) exhibits at least 70% sequence identity to SEQ ID NO: 1 or SEQ ID NO: 2 and has a sequence comprising:
   position 1: Cys, Lys, Asp, or Glu;
   position 2: Val, Ile, Trp, Phe, Tyr or Met;
   position 3: Tyr or Asn;
   position 4: Trp, Val, Phe or Glu;
   position 5: Thr, Val or Ile;
   position 6: Arg, Ile, Val, Glu or Leu;
   position 7: d-Pro;
   position 8: Asp, Lys or Asn;
   position 9: Trp, Lys, Met, Thr or Gln;
   position 10: Lys;
   position 11: Val, Met, His or Leu;
   position 12: Asn, Asp, Ser or His;
   position 13: Trp;
   position 14: if position 1 is a Cys, position 14 is a Cys; if position 1 is a Glu or Asp, position 14 is a Lys, if position 1 is a Lys, position 14 is a Glu or Asp; and, as C-terminal extension, at positions 15-16: Lys-Lys dipeptide, or at positions 15-17: Lys-Lys-Lys tripeptide; or
   (ii) exhibits at least 70% sequence identity to SEQ ID NO: 3 or SEQ ID NO: 4 and has a sequence comprising:
   position 1: Cys, Lys, Asp, or Glu;
   position 2: Ile, Val, Trp, Phe, Tyr or Met;
   position 3: Glu or Asp;
   position 4: Val, Ile, Trp, Phe, Tyr or Met;
   position 5: Tyr or Asn;
   position 6: Trp, Val, Phe, Glu;
   position 7: Thr, Val or Ile;
   position 8: Arg, Ile, Val, Glu or Leu;
   position 9: d-Pro;
   position 10: Asp, Lys or Asn;
   position 11: Trp, Lys, Met, Thr or Gln;
   position 12: Lys;
   position 13: Val, Met, His or Leu;
   position 14: Asn, Asp, Ser or His;
   position 15: Trp;
   position 16: Phe or Tyr;
   position 17: Ile, Val, Trp, Phe, Tyr or Met;
   position 18: if position 1 is a Cys, position 18 is a Cys; if position 1 is a Glu or Asp, position 18 is a Lys, if position 1 is a Lys, position 18 is a Glu or Asp; and as C-terminal extension, at positions 19-20: Lys-Lys dipeptide, or at positions 19-21: Lys-Lys-Lys tripeptide; or
   (iii) exhibits at least 70% sequence identity to SEQ ID NO: 7 and has a sequence comprising:
   position 1: Cys, Lys, Asp, or Glu;
   position 2: Val, Ile, Trp, Phe, Tyr, Met;
   position 3: Tyr or Asn;

position 4: Val, Ile, Phe, Tyr or Leu;
position 5: Thr, Val or Ile;
position 6: Ile, Val, Tyr, His or Lys;
position 7: Asn or Asp;
position 8: Gly;
position 9: Lys, His, Arg, Val, 5 Tyr, Glu or Met;
position 10: Lys;
position 11: Tyr, Val, Gln, Trp or Phe;
position 12: Asn, Asp, Ser or His;
position 13: Trp;
position 14: if position 1 is a Cys, position 14 is a Cys; if position 1 is a Glu or Asp, position 14 is a Lys, if position 1 is a Lys, position 14 is a Glu or Asp; and,as C-terminal extension, at positions 15-16: Lys-Lys dipeptide, or at positions 15-17: Lys-Lys-Lys tripeptide; or (iv) exhibits at least 70% sequence identity to SEQ ID NO: 8 or SEQ ID NO: 9 and has a sequence comprising:
position 1: Cys, Lys, Asp, or Glu;
position 2: Ile, Val, Trp, Phe, Tyr or Met;
position 3: Glu or Asp;
position 4: Val, Ile, Trp, Phe, Tyr, Met;
position 5: Tyr or Asn;
position 6: Val, Ile, Phe, Tyr or Leu;
position 7: Thr, Val or Ile;
position 8: Ile, Val, Tyr, His or Lys;
position 9: Asn or Asp;
position 10: Gly;
position 11: Lys, His, Arg, Val, Tyr, Glu or Met;
position 12: Lys;
position 13: Tyr, Val, Gln, Trp or Phe;
position 14: Asn, Asp, Ser or His;
position 15: Trp;
position 16: Phe or Tyr;
position 17: Ile, Val, Trp, 5 Phe, Tyr or Met;
position 18: if position 1 is a Cys, position 18 is a Cys; if position 1 is a Glu or Asp, position 18 is a Lys, if position 1 is a Lys, position 18 is a Glu or Asp; and, as C-terminal extension, at positions 19-20: Lys-Lys dipeptide, or at positions 19-21: Lys-Lys-Lys tripeptide; or (v) exhibits at least 70% sequence identity to SEQ ID NO: 5 or SEQ ID NO: 6 and has a sequence comprising
position 1: Phe or Tyr;
position 2: Trp;
position 3: Asn, Asp, Ser or His;
position 4: Trp;
position 5: Lys;
position 6: Trp;
position 7: Glu, Val, Arg, Ile or Asp;
position 8: d-Pro or d-Lys;
position 9: Asn, Asp or Lys;
position 10: Lys, Met, Trp, Gln or Thr;
position 11: Trp;
position 12: Thr, Val or Ile;
position 13: Trp;
position 14: Tyr or Asn;
position 15: Ile, Val, Trp, Phe, Tyr or Met;
position 16: Glu or Asp; and, as C-terminal extension, at positions 17-20: Gly Gly-Lys-Lys tetrapeptide, or at positions 17-21: Gly-Gly-Lys-Lys-Lys pentapeptide.

2. A pharmaceutical composition comprising one or more peptides from claim 1 and at least one pharmaceutically acceptable excipient.

3. A pharmaceutical composition according to claim 2, wherein said composition contains human serum albumin.

4. A pharmaceutical composition according to claim 2, wherein the peptides of said composition are forming supramolecular aggregates.

5. A method of inhibiting binding to the protein alfa 2 macroglobulin (α2M), or the protein LRP1, comprising contacting the protein with at least one of the peptides of claim 1.

6. A method of inhibiting or attenuating Dengue virus (DENV) infection in a patient in need thereof, comprising administering to said patient one or more of the peptides of claim 1, or a pharmaceutical composition comprising at least one of the peptides of claim 1.

* * * * *

SEQUENCE LISTING

```
<160> NUMBER OF SEQ ID NOS: 25

<210> SEQ ID NO 1
<211> LENGTH: 17
<212> TYPE: PRT
<213> ORGANISM: Artificial Sequence
<220> FEATURE:
<221> NAME/KEY: MOD_RES
<222> LOCATION: (7)
<223> OTHER INFORMATION: stereoisomer D-Proline
<220> FEATURE:
<221> NAME/KEY: MOD_RES
<222> LOCATION: (17)
<223> OTHER INFORMATION: AMIDATION at C-terminus
<220> FEATURE:
<223> OTHER INFORMATION: Description of Artificial Sequence: Beta
      hairpin peptide, rational design
<220> FEATURE:
<221> NAME/KEY: DISULFID
<222> LOCATION: (1)..(14)

<400> SEQUENCE: 1

Cys Val Asn Trp Thr Glu Pro Asp Lys Lys Val Asn Trp Cys Lys Lys
  1               5                  10                  15

Lys

<210> SEQ ID NO 2
<211> LENGTH: 17
<212> TYPE: PRT
<213> ORGANISM: Artificial Sequence
<220> FEATURE:
<221> NAME/KEY: DISULFID
<222> LOCATION: (1)..(14)
<220> FEATURE:
<221> NAME/KEY: MOD_RES
<222> LOCATION: (7)
<223> OTHER INFORMATION: stereoisomer D-Proline
<220> FEATURE:
<221> NAME/KEY: MOD_RES
<222> LOCATION: (17)
<223> OTHER INFORMATION: AMIDATION at C-terminus
<220> FEATURE:
<223> OTHER INFORMATION: Description of Artificial Sequence: Beta
      hairpin peptide, rational design

<400> SEQUENCE: 2

Cys Val Tyr Trp Thr Arg Pro Lys Trp Lys Val Asn Trp Cys Lys Lys
  1               5                  10                  15

Lys

<210> SEQ ID NO 3
<211> LENGTH: 21
<212> TYPE: PRT
```

```
<213> ORGANISM: Artificial Sequence
<220> FEATURE:
<221> NAME/KEY: DISULFID
<222> LOCATION: (1)..(18)
<220> FEATURE:
<221> NAME/KEY: MOD_RES
<222> LOCATION: (9)
<223> OTHER INFORMATION: stereoisomer D-Proline
<220> FEATURE:
<221> NAME/KEY: MOD_RES
<222> LOCATION: (21)
<223> OTHER INFORMATION: AMIDATION at C-terminus
<220> FEATURE:
<223> OTHER INFORMATION: Description of Artificial Sequence: Beta
      hairpin peptide, rational design

<400> SEQUENCE: 3

Cys Ile Glu Val Asn Trp Thr Glu Pro Asp Lys Lys Val Asn Trp Phe
 1               5                  10                  15

Ile Cys Lys Lys Lys
            20

<210> SEQ ID NO 4
<211> LENGTH: 21
<212> TYPE: PRT
<213> ORGANISM: Artificial Sequence
<220> FEATURE:
<221> NAME/KEY: DISULFID
<222> LOCATION: (1)..(18)
<220> FEATURE:
<221> NAME/KEY: MOD_RES
<222> LOCATION: (9)
<223> OTHER INFORMATION: stereoisomer D-Proline
<220> FEATURE:
<221> NAME/KEY: MOD_RES
<222> LOCATION: (21)
<223> OTHER INFORMATION: AMIDATION at C-terminus
<220> FEATURE:
<223> OTHER INFORMATION: Description of Artificial Sequence: Beta
      hairpin peptide, rational design

<400> SEQUENCE: 4

Cys Ile Glu Val Tyr Trp Thr Arg Pro Lys Trp Lys Val Asn Trp Phe
 1               5                  10                  15

Ile Cys Lys Lys Lys
            20

<210> SEQ ID NO 5
<211> LENGTH: 21
<212> TYPE: PRT
<213> ORGANISM: Artificial Sequence
<220> FEATURE:
<221> NAME/KEY: MOD_RES
<222> LOCATION: (8)
<223> OTHER INFORMATION: stereoisomer D-Lys
<220> FEATURE:
<221> NAME/KEY: MOD_RES
<222> LOCATION: (21)
<223> OTHER INFORMATION: AMIDATION at C-terminus
<220> FEATURE:
<223> OTHER INFORMATION: Description of Artificial Sequence: Beta
      hairpin peptide, rational design

<400> SEQUENCE: 5

Phe Trp Asn Trp Lys Trp Glu Lys Asn Lys Trp Thr Trp Asn Val Glu
 1               5                  10                  15

Gly Gly Lys Lys Lys
            20

<210> SEQ ID NO 6
```

```
<211> LENGTH: 21
<212> TYPE: PRT
<213> ORGANISM: Artificial Sequence
<220> FEATURE:
<221> NAME/KEY: MOD_RES
<222> LOCATION: (8)
<223> OTHER INFORMATION: stereoisomer D-Lys
<220> FEATURE:
<221> NAME/KEY: MOD_RES
<222> LOCATION: (21)
<223> OTHER INFORMATION: AMIDATION at C-terminus
<220> FEATURE:
<223> OTHER INFORMATION: Description of Artificial Sequence: Beta
      hairpin peptide, rational design

<400> SEQUENCE: 6

Phe Trp Asn Trp Lys Trp Glu Pro Asn Lys Trp Thr Trp Asn Val Glu
 1               5                  10                  15

Gly Gly Lys Lys Lys
            20

<210> SEQ ID NO 7
<211> LENGTH: 17
<212> TYPE: PRT
<213> ORGANISM: Artificial Sequence
<220> FEATURE:
<221> NAME/KEY: DISULFID
<222> LOCATION: (1)..(14)
<220> FEATURE:
<221> NAME/KEY: MOD_RES
<222> LOCATION: (17)
<223> OTHER INFORMATION: AMIDATION at C-terminus
<220> FEATURE:
<223> OTHER INFORMATION: Description of Artificial Sequence: Beta
      hairpin peptide, rational design

<400> SEQUENCE: 7

Cys Val Asn Val Thr Ile Asn Gly Lys Lys Tyr Asn Trp Cys Lys Lys
 1               5                  10                  15

Lys

<210> SEQ ID NO 8
<211> LENGTH: 21
<212> TYPE: PRT
<213> ORGANISM: Artificial Sequence
<220> FEATURE:
<221> NAME/KEY: DISULFID
<222> LOCATION: (1)..(18)
<220> FEATURE:
<221> NAME/KEY: MOD_RES
<222> LOCATION: (21)
<223> OTHER INFORMATION: AMIDATION at C-terminus
<220> FEATURE:
<223> OTHER INFORMATION: Description of Artificial Sequence: Beta
      hairpin peptide, rational design

<400> SEQUENCE: 8

Cys Ile Glu Val Asn Val Thr Ile Asn Gly Lys Lys Tyr Asn Trp Phe
 1               5                  10                  15

Ile Cys Lys Lys Lys
            20

<210> SEQ ID NO 9
<211> LENGTH: 21
<212> TYPE: PRT
<213> ORGANISM: Artificial Sequence
<220> FEATURE:
<221> NAME/KEY: DISULFID
<222> LOCATION: (1)..(18)
<220> FEATURE:
```

```
<221> NAME/KEY: MOD_RES
<222> LOCATION: (21)
<223> OTHER INFORMATION: AMIDATION at C-terminus
<220> FEATURE:
<223> OTHER INFORMATION: Description of Artificial Sequence: Beta
      hairpin peptide, rational design

<400> SEQUENCE: 9

Cys Ile Glu Val Tyr Val Thr Ile Asn Gly Lys Lys Tyr Asn Trp Phe
 1               5                  10                  15

Ile Cys Lys Lys Lys
            20

<210> SEQ ID NO 10
<211> LENGTH: 20
<212> TYPE: PRT
<213> ORGANISM: Artificial Sequence
<220> FEATURE:
<221> NAME/KEY: DISULFID
<222> LOCATION: (1)..(18)
<220> FEATURE:
<221> NAME/KEY: MOD_RES
<222> LOCATION: (20)
<223> OTHER INFORMATION: AMIDATION at C-terminus
<220> FEATURE:
<223> OTHER INFORMATION: Description of Artificial Sequence: Beta
      hairpin peptide, rational design

<400> SEQUENCE: 10

Cys Ser Asn Ile Val Ile Gly Ile Gly Asp Lys Ala Leu Lys Ile Asn
 1               5                  10                  15

Trp Cys Lys Lys
            20

<210> SEQ ID NO 11
<211> LENGTH: 21
<212> TYPE: PRT
<213> ORGANISM: Artificial Sequence
<220> FEATURE:
<221> NAME/KEY: DISULFID
<222> LOCATION: (1)..(18)
<220> FEATURE:
<221> NAME/KEY: MOD_RES
<222> LOCATION: (21)
<223> OTHER INFORMATION: AMIDATION at C-terminus
<220> FEATURE:
<223> OTHER INFORMATION: Description of Artificial Sequence: Beta
      hairpin peptide, rational design

<400> SEQUENCE: 11

Cys Ser Asn Ile Val Ile Gly Ile Gly Asp Lys Ala Leu Lys Ile Asn
 1               5                  10                  15

Trp Cys Lys Lys Lys
            20

<210> SEQ ID NO 12
<211> LENGTH: 21
<212> TYPE: PRT
<213> ORGANISM: Artificial Sequence
<220> FEATURE:
<221> NAME/KEY: DISULFID
<222> LOCATION: (1)..(18)
<220> FEATURE:
<221> NAME/KEY: MOD_RES
<222> LOCATION: (21)
<223> OTHER INFORMATION: AMIDATION at C-terminus
<220> FEATURE:
<223> OTHER INFORMATION: Description of Artificial Sequence: Beta
      hairpin peptide, rational design
```

-continued

```
<400> SEQUENCE: 12

Cys Ser Asn Ile Val Ile Gly Ile Gly Asp Lys Ala Leu Lys Ile Asn
 1               5                  10                  15

Ala Cys Lys Lys Lys
            20

<210> SEQ ID NO 13
<211> LENGTH: 21
<212> TYPE: PRT
<213> ORGANISM: Artificial Sequence
<220> FEATURE:
<221> NAME/KEY: DISULFID
<222> LOCATION: (1)..(18)
<220> FEATURE:
<221> NAME/KEY: MOD_RES
<222> LOCATION: (21)
<223> OTHER INFORMATION: AMIDATION at C-terminus
<220> FEATURE:
<223> OTHER INFORMATION: Description of Artificial Sequence: Beta
      hairpin peptide, rational design

<400> SEQUENCE: 13

Cys Ser Asn Ile Val Ile Gly Ile Gly Asp Lys Ala Leu Ala Ile Asn
 1               5                  10                  15

Trp Cys Lys Lys Lys
            20

<210> SEQ ID NO 14
<211> LENGTH: 21
<212> TYPE: PRT
<213> ORGANISM: Artificial Sequence
<220> FEATURE:
<221> NAME/KEY: MOD_RES
<222> LOCATION: (21)
<223> OTHER INFORMATION: AMIDATION at C-terminus
<220> FEATURE:
<223> OTHER INFORMATION: Description of Artificial Sequence: Beta
      hairpin peptide, rational design

<400> SEQUENCE: 14

Ser Ser Asn Ile Val Ile Gly Ile Gly Asp Lys Ala Leu Lys Ile Asn
 1               5                  10                  15

Trp Ser Lys Lys Lys
            20

<210> SEQ ID NO 15
<211> LENGTH: 106
<212> TYPE: PRT
<213> ORGANISM: Dengue virus type 1
<220> FEATURE:
<221> NAME/KEY: DISULFID
<222> LOCATION: (14)..(45)

<400> SEQUENCE: 15

Met Asp Lys Leu Thr Leu Lys Gly Met Ser Tyr Val Met Cys Thr Gly
 1               5                  10                  15

Ser Phe Lys Leu Glu Lys Glu Val Ala Glu Thr Gln His Gly Thr Val
            20                  25                  30

Leu Val Gln Val Lys Tyr Glu Gly Thr Asp Ala Pro Cys Lys Ile Pro
        35                  40                  45

Phe Ser Thr Gln Asp Glu Lys Gly Val Thr Gln Asn Gly Arg Leu Ile
    50                  55                  60

Thr Ala Asn Pro Ile Val Thr Asp Lys Glu Lys Pro Val Asn Ile Glu
65                  70                  75                  80
```

```
Thr Glu Pro Pro Phe Gly Glu Ser Tyr Ile Val Val Gly Ala Gly Glu
                85                  90                  95

Lys Ala Leu Lys Leu Ser Trp Phe Lys Lys
            100                 105

<210> SEQ ID NO 16
<211> LENGTH: 342
<212> TYPE: DNA
<213> ORGANISM: Dengue virus type 1
<220> FEATURE:
<221> NAME/KEY: CDS
<222> LOCATION: (1)
<223> OTHER INFORMATION: fragment Nde I/Xho I coding for rDIII DENV1
<220> FEATURE:
<223> OTHER INFORMATION: DNA, lineal, double-stranded

<400> SEQUENCE: 16
catatggata aactgacttt aaaagggatg agctatgtga tgtgcacagg ctcatttaag      60
ctagagaagg aagtggctga gacccagcat ggaactgttc tagtgcaggt taaatacgaa     120
ggaacagatg cgccatgcaa gatcccctt tcgacccaag atgagaaagg agtgacccag      180
aatgggagat tgataacagc caatcccata gttactgaca agaaaaaacc agtcaacatt    240
gagacagaac cacctttggg tgagagctac atcgtggtag gggcaggtga aaaagctttg    300
aaactaagct ggttcaagaa aggaagcagc atagggctcg ag                       342

<210> SEQ ID NO 17
<211> LENGTH: 119
<212> TYPE: PRT
<213> ORGANISM: Artificial Sequence
<220> FEATURE:
<221> NAME/KEY: SITE
<222> LOCATION: (114)..(119)
<223> OTHER INFORMATION: histidine-tag
<220> FEATURE:
<223> OTHER INFORMATION: Description of Artificial Sequence: rDIII
      DENV1, recombinant domain III from DENV1

<400> SEQUENCE: 17

Met Asp Lys Leu Thr Leu Lys Gly Met Ser Tyr Val Met Cys Thr Gly
 1               5                  10                  15

Ser Phe Lys Leu Glu Lys Glu Val Ala Glu Thr Gln His Gly Thr Val
                20                  25                  30

Leu Val Gln Val Lys Tyr Glu Gly Thr Asp Ala Pro Cys Lys Ile Pro
            35                  40                  45

Phe Ser Thr Gln Asp Glu Lys Gly Val Thr Gln Asn Gly Arg Leu Ile
        50                  55                  60

Thr Ala Asn Pro Ile Val Thr Asp Lys Glu Lys Pro Val Asn Ile Glu
 65                  70                  75                  80

Thr Glu Pro Pro Phe Gly Glu Ser Tyr Ile Val Val Gly Ala Gly Glu
                85                  90                  95

Lys Ala Leu Lys Leu Ser Trp Phe Lys Lys Gly Ser Ser Ile Gly Val
            100                 105                 110

Asp His His His His His His
            115

<210> SEQ ID NO 18
<211> LENGTH: 5700
<212> TYPE: DNA
<213> ORGANISM: Artificial Sequence
<220> FEATURE:
<223> OTHER INFORMATION: DNA, double stranded, circular
<220> FEATURE:
```

<223> OTHER INFORMATION: Description of Artificial Sequence: plasmid
      pET-DIII DEN1 coding for rDIII DENV1

<400> SEQUENCE: 18

```
catatggata aactgacttt aaaagggatg agctatgtga tgtgcacagg ctcatttaag     60
ctagagaagg aagtggctga gacccagcat ggaactgttc tagtgcaggt taaatacgaa    120
ggaacagatg cgccatgcaa gatcccettt tcgacccaag atgagaaagg agtgacccag    180
aatgggagat tgataacagc caatcccata gttactgaca aagaaaaacc agtcaacatt    240
gagacagaac caccttttgg tgagagctac atcgtggtag gggcaggtga aaaagctttg    300
aaactaagct ggttcaagaa aggaagcagc atagggctcg agcaccacca ccaccaccac    360
tgagatccgg ctgctaacaa agcccgaaag gaagctgagt tggctgctgc caccgctgag    420
caataactag cataacccct tggggcctct aaacgggtct tgaggggttt tttgctgaaa    480
ggaggaacta tatccggatt ggcgaatggg acgcgccctg tagcggcgca ttaagcgcgg    540
cgggtgtggt ggttacgcgc agcgtgaccg ctacacttgc cagcgcccta gcgcccgctc    600
ctttcgcttt cttcccttcc tttctcgcca cgttcgccgg ctttccccgt caagctctaa    660
atcgggggct ccctttaggg ttccgattta gtgctttacg gcacctcgac cccaaaaaac    720
ttgattaggg tgatggttca cgtagtgggc catcgccctg atagacggtt tttcgccctt    780
tgacgttgga gtccacgttc tttaatagtg gactcttgtt ccaaactgga acaacactca    840
accctatctc ggtctattct tttgatttat aagggatttt gccgatttcg gcctattggt    900
taaaaaatga gctgatttaa caaaaattta acgcgaattt taacaaaata ttaacgttta    960
caatttcagg tggcactttt cggggaaatg tgcgcggaac ccctatttgt ttatttttct   1020
aaatacattc aaatatgtat ccgctcatga gacaataacc ctgataaatg cttcaataat   1080
attgaaaaag gaagagtatg agtattcaac atttccgtgt cgcccttatt cccttttttg   1140
cggcattttg ccttcctgtt tttgctcacc cagaaacgct ggtgaaagta aaagatgctg   1200
aagatcagtt gggtgcacga gtgggttaca tcgaactgga tctcaacagc ggtaagatcc   1260
ttgagagttt tcgccccgaa gaacgttttc caatgatgag cacttttaaa gttctgctat   1320
gtggcgcggt attatcccgt attgacgccg ggcaagagca actcggtcgc cgcatacact   1380
attctcagaa tgacttggtt gagtactcac cagtcacaga aaagcatctt acggatggca   1440
tgacagtaag agaattatgc agtgctgcca taaccatgag tgataacact gcggccaact   1500
tacttctgac aacgatcgga ggaccgaagg agctaaccgc ttttttgcac aacatggggg   1560
atcatgtaac tcgccttgat cgttgggaac cggagctgaa tgaagccata ccaaacgacg   1620
agcgtgacac cacgatgcct gcagcaatgg caacaacgtt gcgcaaacta ttaactggcg   1680
aactacttac tctagcttcc cggcaacaat taatagactg gatggaggcg gataaagttg   1740
caggaccact tctgcgctcg gcccttccgg ctggctggtt tattgctgat aaatctggag   1800
ccggtgagcg tgggtctcgc ggtatcattg cagcactggg gccagatggt aagccctccc   1860
gtatcgtagt tatctacacg acggggagtc aggcaactat ggatgaacga aatagacaga   1920
tcgctgagat aggtgcctca ctgattaagc attggtaact gtcagaccaa gtttactcat   1980
atatacttta gattgattta aaacttcatt tttaatttaa aaggatctag gtgaagatcc   2040
tttttgataa tctcatgacc aaaatccctt aacgtgagtt ttcgttccac tgagcgtcag   2100
accccgtaga aaagatcaaa ggatcttctt gagatccttt ttttctgcgc gtaatctgct   2160
gcttgcaaac aaaaaaacca ccgctaccag cggtggtttg tttgccggat caagagctac   2220
```

```
caactctttt tccgaaggta actggcttca gcagagcgca gataccaaat actgtccttc    2280
tagtgtagcc gtagttaggc caccacttca agaactctgt agcaccgcct acatacctcg    2340
ctctgctaat cctgttacca gtggctgctg ccagtggcga taagtcgtgt cttaccgggt    2400
tggactcaag acgatagtta ccggataagg cgcagcggtc gggctgaacg ggggttcgt     2460
gcacacagcc cagcttggag cgaacgacct acaccgaact gagataccta cagcgtgagc    2520
tatgagaaag cgccacgctt cccgaaggga gaaaggcgga caggtatccg gtaagcggca    2580
gggtcggaac aggagagcgc acgagggagc ttccagggggg aaacgcctgg tatctttata   2640
gtcctgtcgg gtttcgccac ctctgacttg agcgtcgatt tttgtgatgc tcgtcagggg    2700
ggcggagcct atggaaaaac gccagcaacg cggcctttt acggttcctg gccttttgct     2760
ggccttttgc tcacatgttc tttcctgcgt tatcccctga ttctgtggat aaccgtatta    2820
ccgcctttga gtgagctgat accgctcgcc gcagccgaac gaccgagcgc agcgagtcag    2880
tgagcgagga gcggaagag cgcctgatgc ggtattttct ccttacgcat ctgtgcggta     2940
tttcacaccg catatatggt gcactctcag tacaatctgc tctgatgccg catagttaag    3000
ccagtataca ctccgctatc gctacgtgac tgggtcatgg ctgcgccccg acacccgcca    3060
acacccgctg acgcgccctg acgggcttgt ctgctcccgg catccgctta cagacaagct    3120
gtgaccgtct ccgggagctg catgtgtcag aggttttcac cgtcatcacc gaaacgcgcg    3180
aggcagctgc ggtaaagctc atcagcgtgg tcgtgaagcg attcacagat gtctgcctgt    3240
tcatccgcgt ccagctcgtt gagtttctcc agaagcgtta atgtctggct tctgataaag    3300
cgggccatgt taagggcggt ttttcctgt ttggtcactg atgcctccgt gtaaggggga    3360
tttctgttca tgggggtaat gataccgatg aaacgagaga ggatgctcac gatacgggtt    3420
actgatgatg aacatgcccg gttactgaa cgttgtgagg gtaaacaact ggcggtatgg     3480
atgcggcggg accagagaaa aatcactcag ggtcaatgcc agcgcttcgt taatacagat    3540
gtaggtgttc cacagggtag ccagcagcat cctgcgatgc agatccggaa cataatggtg    3600
cagggcgctg acttccgcgt ttccagactt tacgaaacac ggaaaccgaa gaccattcat    3660
gttgttgctc aggtcgcaga cgttttgcag cagcagtcgc ttcacgttcg ctcgcgtatc    3720
ggtgattcat tctgctaacc agtaaggcaa ccccgccagc ctagccgggt cctcaacgac    3780
aggagcacga tcatgcgcac ccgtggggcc gccatgccgg cgataatggc ctgcttctcg    3840
ccgaaacgtt tggtggcggg accagtgacg aaggcttgag cgagggcgtg caagattccg    3900
aataccgcaa gcgacaggcc gatcatcgtc gcgctccagc gaaagcggtc ctcgccgaaa    3960
atgacccaga gcgctgccgg cacctgtcct acgagttgca tgataaagaa gacagtcata    4020
agtgcggcga cgatagtcat gccccgcgcc caccggaagg agctgactgg gttgaaggct    4080
ctcaagggca tcggtcgaga tcccggtgcc taatgagtga gctaacttac attaattgcg    4140
ttgcgctcac tgcccgcttt ccagtcggga aacctgtcgt gccagctgca ttaatgaatc    4200
ggccaacgcg cggggagagg cggtttgcgt attgggcgcc agggtggttt ttcttttcac    4260
cagtgagacg ggcaacagct gattgccctt caccgcctgg ccctgagaga gttgcagcaa    4320
gcggtccacg ctggtttgcc ccagcaggcg aaaatcctgt ttgatggtgg ttaacggcgg    4380
gatataacat gagctgtctt cggtatcgtc gtatcccact accgagatat ccgcaccaac    4440
gcgcagcccg gactcggtaa tggcgcgcat tgcgcccagc gccatctgat cgttggcaac    4500
cagcatcgca gtgggaacga tgccctcatt cagcatttgc atggtttgtt gaaaaccgga    4560
catggcactc cagtcgcctt cccgttccgc tatcggctga atttgattgc gagtgagata    4620
```

-continued

```
tttatgccag ccagccagac gcagacgcgc cgagacagaa cttaatgggc ccgctaacag    4680
cgcgatttgc tggtgaccca atgcgaccag atgctccacg cccagtcgcg taccgtcttc    4740
atgggagaaa ataatactgt tgatgggtgt ctggtcagag acatcaagaa ataacgccgg    4800
aacattagtg caggcagctt ccacagcaat ggcatcctgg tcatccagcg atagttaat    4860 gatcagccca ctgacgcgtt gcgcgagaag attgtgcacc gccgctttac aggcttcgac    4920
gccgcttcgt tctaccatcg acaccaccac gctggcaccc agttgatcgg cgcgagattt    4980
aatcgccgcg acaatttgcg acggcgcgtg cagggccaga ctggaggtgg caacgccaat    5040
cagcaacgac tgtttgcccg ccagttgttg tgccacgcgg ttgggaatgt aattcagctc    5100
cgccatcgcc gcttccactt ttttcccgcgt tttcgcagaa acgtggctgg cctggttcac    5160
cacgcgggaa acggtctgat aagagacacc ggcatactct gcgacatcgt ataacgttac    5220
tggtttcaca ttcaccaccc tgaattgact ctcttccggg cgctatcatg ccataccgcg    5280
aaaggttttg cgccattcga tggtgtccgg atctcgacg ctctccctta tgcgactcct    5340
gcattaggaa gcagcccagt agtaggttga ggccgttgag caccgccgcc gcaaggaatg    5400
gtgcatgcaa ggagatggcg cccaacagtc ccccggccac ggggcctgcc accataccca    5460
cgccgaaaca agcgctcatg agcccgaagt ggcgagcccg atcttcccca tcggtgatgt    5520
cggcgatata ggcgccagca accgcacctg tggcgccggt gatgccggcc acgatgcgtc    5580
cggcgtagag gatcgagatc tcgatcccgc gaaattaata cgactcacta tagggggaatt    5640 gtgagcggat aacaattccc ctctagaaat aattttgttt aactttaaga aggagatata    5700
```

<210> SEQ ID NO 19
<211> LENGTH: 119
<212> TYPE: PRT
<213> ORGANISM: Artificial Sequence
<220> FEATURE:
<221> NAME/KEY: SIMILAR
<222> LOCATION: (114)..(119)
<223> OTHER INFORMATION: histidine-tag
<220> FEATURE:
<223> OTHER INFORMATION: Description of Artificial Sequence: recombinant
      protein containing domain III of the envelope
      protein from virus Dengue type 1
<300> PUBLICATION INFORMATION:

<400> SEQUENCE: 19

```
Met Asp Lys Leu Gln Leu Lys Gly Met Ser Tyr Ser Met Cys Thr Gly
  1               5                  10                  15

Lys Phe Lys Ile Val Lys Glu Ile Ala Glu Thr Gln His Gly Thr Ile
             20                  25                  30

Val Ile Arg Val Gln Tyr Glu Gly Asp Gly Ser Pro Cys Lys Ile Pro
         35                  40                  45

Phe Glu Ile Met Asp Leu Glu Lys Arg His Val Leu Gly Arg Leu Ile
     50                  55                  60

Thr Val Asn Pro Ile Val Thr Glu Lys Asp Ser Pro Val Asn Ile Glu
 65                  70                  75                  80

Ala Glu Pro Pro Phe Gly Asp Ser Tyr Ile Ile Ile Gly Val Glu Pro
                 85                  90                  95

Gly Gln Leu Lys Leu Asn Trp Phe Lys Lys Gly Ser Ser Ile Gly Leu
            100                 105                 110

Glu His His His His His His
        115
```

-continued

```
<210> SEQ ID NO 20
<211> LENGTH: 119
<212> TYPE: PRT
<213> ORGANISM: Artificial Sequence
<220> FEATURE:
<221> NAME/KEY: SITE
<222> LOCATION: (114)..(119)
<223> OTHER INFORMATION: histidine-tag
<220> FEATURE:
<223> OTHER INFORMATION: Description of Artificial Sequence: recombinant
      protein containing domain III of the envelope
      protein from virus Dengue type 2

<400> SEQUENCE: 20

Met Asp Lys Leu Thr Leu Lys Gly Met Ser Tyr Val Met Cys Thr Gly
  1               5                  10                  15

Ser Phe Lys Leu Glu Lys Glu Val Ala Glu Thr Gln His Gly Thr Val
             20                  25                  30

Leu Val Gln Val Lys Tyr Glu Gly Thr Asp Ala Pro Cys Lys Ile Pro
         35                  40                  45

Phe Ser Thr Gln Asp Glu Lys Gly Val Thr Gln Asn Gly Arg Leu Ile
     50                  55                  60

Thr Ala Asn Pro Ile Val Thr Asp Lys Glu Lys Pro Val Asn Ile Glu
 65                  70                  75                  80

Thr Glu Pro Pro Phe Gly Glu Ser Tyr Ile Val Val Gly Ala Gly Glu
                 85                  90                  95

Lys Ala Leu Lys Leu Ser Trp Phe Lys Lys Gly Ser Ser Ile Gly Leu
            100                 105                 110

Glu His His His His His His
        115

<210> SEQ ID NO 21
<211> LENGTH: 119
<212> TYPE: PRT
<213> ORGANISM: Artificial Sequence
<220> FEATURE:
<221> NAME/KEY: SITE
<222> LOCATION: (114)..(119)
<223> OTHER INFORMATION: histidine-tag
<220> FEATURE:
<223> OTHER INFORMATION: Description of Artificial Sequence: recombinant
      protein containing domain III of the envelope
      protein from virus Dengue type 3

<400> SEQUENCE: 21

Met Asp Lys Leu Glu Leu Lys Gly Met Ser Tyr Ala Met Cys Thr Asn
  1               5                  10                  15

Thr Phe Val Leu Lys Lys Glu Val Ser Glu Thr Gln His Gly Thr Ile
             20                  25                  30

Leu Ile Lys Val Glu Tyr Lys Gly Glu Asp Val Pro Cys Lys Ile Pro
         35                  40                  45

Phe Ser Thr Glu Asp Gly Gln Gly Lys Ala His Asn Gly Arg Leu Ile
     50                  55                  60

Thr Ala Asn Pro Val Val Thr Lys Lys Glu Glu Pro Val Asn Ile Glu
 65                  70                  75                  80

Ala Glu Pro Pro Phe Gly Glu Ser Asn Ile Val Ile Gly Ile Gly Asp
                 85                  90                  95

Asn Ala Leu Lys Ile Asn Trp Tyr Lys Lys Gly Ser Ser Ile Gly Leu
            100                 105                 110

Glu His His His His His His
        115
```

```
<210> SEQ ID NO 22
<211> LENGTH: 119
<212> TYPE: PRT
<213> ORGANISM: Artificial Sequence
<220> FEATURE:
<221> NAME/KEY: SITE
<222> LOCATION: (114)..(119)
<223> OTHER INFORMATION: histidine-tag
<220> FEATURE:
<223> OTHER INFORMATION: Description of Artificial Sequence: recombinant
      protein containing domain III of the envelope
      protein from virus Dengue type 4

<400> SEQUENCE: 22

Met Glu Lys Leu Arg Ile Lys Gly Met Ser Tyr Thr Met Cys Ser Gly
 1               5                  10                  15

Lys Phe Ser Ile Asp Lys Glu Met Ala Glu Thr Gln His Gly Thr Thr
            20                  25                  30

Val Val Lys Val Lys Tyr Glu Gly Ala Gly Ala Pro Cys Lys Val Pro
        35                  40                  45

Ile Glu Ile Arg Asp Val Asn Lys Glu Lys Val Val Gly Arg Ile Ile
    50                  55                  60

Ser Ser Thr Pro Leu Ala Glu Asn Thr Asn Ser Val Thr Asn Ile Glu
65                  70                  75                  80

Leu Glu Pro Pro Phe Gly Asp Ser Tyr Ile Val Ile Gly Val Gly Asn
                85                  90                  95

Ser Ala Leu Thr Leu His Trp Phe Arg Lys Gly Ser Ser Ile Gly Leu
            100                 105                 110

Glu His His His His His His
        115

<210> SEQ ID NO 23
<211> LENGTH: 617
<212> TYPE: PRT
<213> ORGANISM: Homo sapiens
<220> FEATURE:
<223> OTHER INFORMATION: cluster II of human LRP1

<400> SEQUENCE: 23

Arg Pro Pro Ile Phe Glu Ile Arg Met Tyr Asp Ala Gln Gln Gln Gln
 1               5                  10                  15

Val Gly Thr Asn Lys Cys Arg Val Asn Asn Gly Gly Cys Ser Ser Leu
            20                  25                  30

Cys Leu Ala Thr Pro Gly Ser Arg Gln Cys Ala Cys Ala Glu Asp Gln
        35                  40                  45

Val Leu Asp Ala Asp Gly Val Thr Cys Leu Ala Asn Pro Ser Tyr Val
    50                  55                  60

Pro Pro Pro Gln Cys Gln Pro Gly Glu Phe Ala Cys Ala Asn Ser Arg
65                  70                  75                  80

Cys Ile Gln Glu Arg Trp Lys Cys Asp Gly Asp Asn Asp Cys Leu Asp
                85                  90                  95

Asn Ser Asp Glu Ala Pro Ala Leu Cys His Gln His Thr Cys Pro Ser
            100                 105                 110

Asp Arg Phe Lys Cys Glu Asn Asn Arg Cys Ile Pro Asn Arg Trp Leu
        115                 120                 125

Cys Asp Gly Asp Asn Asp Cys Gly Asn Ser Glu Asp Glu Ser Asn Ala
    130                 135                 140

Thr Cys Ser Ala Arg Thr Cys Pro Pro Asn Gln Phe Ser Cys Ala Ser
145                 150                 155                 160
```

-continued

Gly Arg Cys Ile Pro Ile Ser Trp Thr Cys Asp Leu Asp Asp Cys
            165                 170                 175

Gly Asp Arg Ser Asp Glu Ser Ala Ser Cys Ala Tyr Pro Thr Cys Phe
        180                 185                 190

Pro Leu Thr Gln Phe Thr Cys Asn Asn Gly Arg Cys Ile Asn Ile Asn
            195                 200                 205

Trp Arg Cys Asp Asn Asp Asn Asp Cys Gly Asp Asn Ser Asp Glu Ala
210                 215                 220

Gly Cys Ser His Ser Cys Ser Ser Thr Gln Phe Lys Cys Asn Ser Gly
225                 230                 235                 240

Arg Cys Ile Pro Glu His Trp Thr Cys Asp Gly Asp Asn Asp Cys Gly
            245                 250                 255

Asp Tyr Ser Asp Glu Thr His Ala Asn Cys Thr Asn Gln Ala Thr Arg
        260                 265                 270

Pro Pro Gly Gly Cys His Thr Asp Glu Phe Gln Cys Arg Leu Asp Gly
            275                 280                 285

Leu Cys Ile Pro Leu Arg Trp Arg Cys Asp Gly Asp Thr Asp Cys Met
290                 295                 300

Asp Ser Ser Asp Glu Lys Ser Cys Glu Gly Val Thr His Val Cys Asp
305                 310                 315                 320

Pro Ser Val Lys Phe Gly Cys Lys Asp Ser Ala Arg Cys Ile Ser Lys
            325                 330                 335

Ala Trp Val Cys Asp Gly Asp Asn Asp Cys Glu Asp Asn Ser Asp Glu
            340                 345                 350

Glu Asn Cys Glu Ser Leu Ala Cys Arg Pro Pro Ser His Pro Cys Ala
        355                 360                 365

Asn Asn Thr Ser Val Cys Leu Pro Pro Asp Lys Leu Ile Glu Gly Arg
        370                 375                 380

Met Asp Pro Lys Ser Cys Asp Lys Thr His Thr Cys Pro Pro Cys Pro
385                 390                 395                 400

Ala Pro Glu Leu Leu Gly Gly Pro Ser Val Phe Leu Phe Pro Pro Lys
            405                 410                 415

Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
    450                 455                 460

Gln Tyr Asn Ser Thr Tyr Arg Val Val Ser Val Leu Thr Val Leu His
465                 470                 475                 480

Gln Asp Trp Leu Asn Gly Lys Glu Tyr Lys Cys Lys Val Ser Asn Lys
            485                 490                 495

Ala Leu Pro Ala Pro Ile Glu Lys Thr Ile Ser Lys Ala Lys Gly Gln
            500                 505                 510

Pro Arg Glu Pro Gln Val Tyr Thr Leu Pro Pro Ser Arg Asp Glu Leu
        515                 520                 525

Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
            565                 570                 575

-continued

Tyr Ser Lys Leu Thr Val Asp Lys Ser Arg Trp Gln Gln Gly Asn Val
              580                 585                 590

Phe Ser Cys Ser Val Met His Glu Ala Leu His Asn His Tyr Thr Gln
       595                 600                 605

Lys Ser Leu Ser Leu Ser Pro Gly Lys
    610                 615

<210> SEQ ID NO 24
<211> LENGTH: 656
<212> TYPE: PRT
<213> ORGANISM: Homo sapiens
<220> FEATURE:
<223> OTHER INFORMATION: cluster III of human LRP1

<400> SEQUENCE: 24

Ser Ser Cys Arg Ala Gln Asp Glu Phe Glu Cys Ala Asn Gly Glu Cys
 1               5                  10                  15

Ile Asn Phe Ser Leu Thr Cys Asp Gly Val Pro His Cys Lys Asp Lys
             20                  25                  30

Ser Asp Glu Lys Pro Ser Tyr Cys Asn Ser Arg Arg Cys Lys Lys Thr
         35                  40                  45

Phe Arg Gln Cys Ser Asn Gly Arg Cys Val Ser Asn Met Leu Trp Cys
     50                  55                  60

Asn Gly Ala Asp Asp Cys Gly Asp Gly Ser Asp Glu Ile Pro Cys Asn
 65                  70                  75                  80

Lys Thr Ala Cys Gly Val Gly Glu Phe Arg Cys Arg Asp Gly Thr Cys
                 85                  90                  95

Ile Gly Asn Ser Ser Arg Cys Asn Gln Phe Val Asp Cys Glu Asp Ala
            100                 105                 110

Ser Asp Glu Met Asn Cys Ser Ala Thr Asp Cys Ser Ser Tyr Phe Arg
        115                 120                 125

Leu Gly Val Lys Gly Val Leu Phe Gln Pro Cys Glu Arg Thr Ser Leu
    130                 135                 140

Cys Tyr Ala Pro Ser Trp Val Cys Asp Gly Ala Asn Asp Cys Gly Asp
145                 150                 155                 160

Tyr Ser Asp Glu Arg Asp Cys Pro Gly Val Lys Arg Pro Arg Cys Pro
                165                 170                 175

Leu Asn Tyr Phe Ala Cys Pro Ser Gly Arg Cys Ile Pro Ser Trp Thr
            180                 185                 190

Cys Asp Lys Glu Asp Asp Cys Glu His Gly Glu Asp Glu Thr His Cys
        195                 200                 205

Asn Lys Phe Cys Ser Glu Ala Gln Phe Glu Cys Gln Asn His Arg Cys
    210                 215                 220

Ile Ser Lys Gln Trp Leu Cys Asp Gly Ser Asp Asp Cys Gly Asp Gly
225                 230                 235                 240

Ser Asp Glu Ala Ala His Cys Glu Gly Lys Thr Cys Gly Pro Ser Ser
                245                 250                 255

Phe Ser Cys Pro Gly Thr His Val Cys Val Pro Glu Arg Trp Leu Cys
            260                 265                 270

Asp Gly Asp Lys Asp Cys Ala Asp Gly Ala Asp Glu Ser Ile Ala Ala
        275                 280                 285

Gly Cys Leu Tyr Asn Ser Thr Cys Asp Asp Arg Glu Phe Met Cys Gln
    290                 295                 300

Asn Arg Gln Cys Ile Pro Lys His Phe Val Cys Asp His Asp Arg Asp
305                 310                 315                 320

Cys Ala Asp Gly Ser Asp Glu Ser Pro Glu Cys Tyr Pro Thr Cys
                325                 330                 335

Gly Pro Ser Glu Phe Arg Cys Ala Asn Gly Arg Cys Leu Ser Ser Arg
            340                 345                 350

Gln Trp Glu Cys Asp Gly Glu Asn Asp Cys His Asp Gln Ser Asp Glu
        355                 360                 365

Ala Pro Lys Asn Pro His Cys Thr Ser Gln Glu His Lys Cys Asn Ala
    370                 375                 380

Ser Ser Gln Phe Leu Cys Ser Ser Gly Arg Cys Val Ala Glu Ala Leu
385                 390                 395                 400

Leu Cys Asn Gly Gln Asp Asp Cys Gly Asp Ser Ser Asp Glu Arg Gly
            405                 410                 415

Cys His Ile Ile Glu Gly Arg Met Asp Pro Lys Ser Cys Asp Lys Thr
        420                 425                 430

His Thr Cys Pro Pro Cys Pro Ala Pro Glu Leu Leu Gly Gly Pro Ser
    435                 440                 445

Val Phe Leu Phe Pro Pro Lys Pro Lys Asp Thr Leu Met Ile Ser Arg
    450                 455                 460

Thr Pro Glu Val Thr Cys Val Val Val Asp Val Ser His Glu Asp Pro
465                 470                 475                 480

Glu Val Lys Phe Asn Trp Tyr Val Asp Gly Val Glu Val His Asn Ala
            485                 490                 495

Lys Thr Lys Pro Arg Glu Glu Gln Tyr Asn Ser Thr Tyr Arg Val Val
        500                 505                 510

Ser Val Leu Thr Val Leu His Gln Asp Trp Leu Asn Gly Lys Glu Tyr
    515                 520                 525

Lys Cys Lys Val Ser Asn Lys Ala Leu Pro Ala Pro Ile Glu Lys Thr
530                 535                 540

Ile Ser Lys Ala Lys Gly Gln Pro Arg Glu Pro Gln Val Tyr Thr Leu
545                 550                 555                 560

Pro Pro Ser Arg Asp Glu Leu Thr Lys Asn Gln Val Ser Leu Thr Cys
            565                 570                 575

Leu Val Lys Gly Phe Tyr Pro Ser Asp Ile Ala Val Glu Trp Glu Ser
        580                 585                 590

Asn Gly Gln Pro Glu Asn Asn Tyr Lys Thr Thr Pro Pro Val Leu Asp
    595                 600                 605

Ser Asp Gly Ser Phe Phe Leu Tyr Ser Lys Leu Thr Val Asp Lys Ser
610                 615                 620

Arg Trp Gln Gln Gly Asn Val Phe Ser Cys Ser Val Met His Glu Ala
625                 630                 635                 640

Leu His Asn His Tyr Thr Gln Lys Ser Leu Ser Leu Ser Pro Gly Lys
            645                 650                 655

<210> SEQ ID NO 25
<211> LENGTH: 685
<212> TYPE: PRT
<213> ORGANISM: Homo sapiens
<220> FEATURE:
<223> OTHER INFORMATION: cluster IV of human LRP1

<400> SEQUENCE: 25

Ser Asn Cys Thr Ala Ser Gln Phe Val Cys Lys Asn Asp Lys Cys Ile
1               5                   10                  15

Pro Phe Trp Trp Lys Cys Asp Thr Glu Asp Asp Cys Gly Asp His Ser
            20                  25                  30

```
Asp Glu Pro Pro Asp Cys Pro Glu Phe Lys Cys Arg Pro Gly Gln Phe
            35                  40                  45
Gln Cys Ser Thr Gly Ile Cys Thr Asn Pro Ala Phe Ile Cys Asp Gly
     50                  55                  60
Asp Asn Asp Cys Gln Asp Asn Ser Asp Glu Ala Asn Cys Asp Ile His
 65                  70                  75                  80
Val Cys Leu Pro Ser Gln Phe Lys Cys Thr Asn Thr Asn Arg Cys Ile
                 85                  90                  95
Pro Gly Ile Phe Arg Cys Asn Gly Gln Asp Asn Cys Gly Asp Gly Glu
            100                 105                 110
Asp Glu Arg Asp Cys Pro Glu Val Thr Cys Ala Pro Asn Gln Phe Gln
            115                 120                 125
Cys Ser Ile Thr Lys Arg Cys Ile Pro Arg Val Trp Val Cys Asp Arg
    130                 135                 140
Asp Asn Asp Cys Val Asp Gly Ser Asp Glu Pro Ala Asn Cys Thr Gln
145                 150                 155                 160
Met Thr Cys Gly Val Asp Glu Phe Arg Cys Lys Asp Ser Gly Arg Cys
                165                 170                 175
Ile Pro Ala Arg Trp Lys Cys Asp Gly Glu Asp Asp Cys Gly Asp Gly
            180                 185                 190
Ser Asp Glu Pro Lys Glu Glu Cys Asp Glu Arg Thr Cys Glu Pro Tyr
    195                 200                 205
Gln Phe Arg Cys Lys Asn Asn Arg Cys Val Pro Gly Arg Trp Gln Cys
    210                 215                 220
Asp Tyr Asp Asn Asp Cys Gly Asp Asn Ser Asp Glu Glu Ser Cys Thr
225                 230                 235                 240
Pro Arg Pro Cys Ser Glu Ser Glu Phe Ser Cys Ala Asn Gly Arg Cys
                245                 250                 255
Ile Ala Gly Arg Trp Lys Cys Asp Gly Asp His Asp Cys Ala Asp Gly
            260                 265                 270
Ser Asp Glu Lys Asp Cys Thr Pro Arg Cys Asp Met Asp Gln Phe Gln
    275                 280                 285
Cys Lys Ser Gly His Cys Ile Pro Leu Arg Trp Arg Cys Asp Ala Asp
    290                 295                 300
Ala Asp Cys Met Asp Gly Ser Asp Glu Glu Ala Cys Gly Thr Gly Val
305                 310                 315                 320
Arg Thr Cys Pro Leu Asp Glu Phe Gln Cys Asn Asn Thr Leu Cys Lys
                325                 330                 335
Pro Leu Ala Trp Lys Cys Asp Gly Glu Asp Asp Cys Gly Asp Asn Ser
            340                 345                 350
Asp Glu Asn Pro Glu Glu Cys Ala Arg Phe Val Cys Pro Pro Asn Arg
            355                 360                 365
Pro Phe Arg Cys Lys Asn Asp Arg Val Cys Leu Trp Ile Gly Arg Gln
    370                 375                 380
Cys Asp Gly Thr Asp Asn Cys Gly Asp Gly Thr Asp Glu Glu Asp Cys
385                 390                 395                 400
Glu Pro Pro Thr Ala His Thr Thr His Cys Lys Asp Lys Lys Glu Phe
                405                 410                 415
Leu Cys Arg Asn Gln Arg Cys Leu Ser Ser Leu Arg Cys Asn Met
            420                 425                 430
Phe Asp Asp Cys Gly Asp Gly Ser Asp Glu Glu Asp Cys Ser Ile Asp
            435                 440                 445
Ile Glu Gly Arg Met Asp Pro Lys Ser Cys Asp Lys Thr His Thr Cys
```

-continued

```
            450                 455                 460
Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Asp Val Ser His Glu Asp Pro Glu Val Lys
            500                 505                 510

Phe Asn Trp Tyr Val Asp Gly Val Glu Val His Asn Ala Lys Thr Lys
            515                 520                 525

Pro Arg Glu Glu Gln Tyr Asn Ser Thr Tyr Arg Val Val Ser Val Leu
                530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
                580                 585                 590

Arg Asp Glu Leu Thr Lys Asn Gln Val Ser Leu Thr Cys Leu Val Lys
                595                 600                 605

Gly Phe Tyr Pro Ser Asp Ile Ala Val Glu Trp Glu Ser Asn Gly Gln
                610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
                660                 665                 670

His Tyr Thr Gln Lys Ser Leu Ser Leu Ser Pro Gly Lys
                675                 680                 685
```